United States Patent [19]
Wang et al.

[11] Patent Number: 6,100,076
[45] Date of Patent: Aug. 8, 2000

[54] O-FUCOSYLTRANSFERASE

[75] Inventors: Yang Wang, Milbrae; Michael W. Spellman, Belmont, both of Calif.

[73] Assignee: Genentech, Inc., South San Francisco, Calif.

[21] Appl. No.: 08/978,741

[22] Filed: Nov. 26, 1997

Related U.S. Application Data

[63] Continuation-in-part of application No. 08/792,498, Jan. 31, 1997, abandoned.

[51] Int. Cl.$^7$ .................................................. C12N 9/10
[52] U.S. Cl. ............................................... 435/193
[58] Field of Search ............................................ 435/193

[56] References Cited

U.S. PATENT DOCUMENTS 4,816,567  3/1989  Cabilly et al. ........................ 530/387

FOREIGN PATENT DOCUMENTS 307247     3/1989  European Pat. Off. .
WO 91/08291 6/1991  WIPO .

OTHER PUBLICATIONS

Appella et al., "The Receptor–binding Sequence of Urokinase" *Journal of Biological Chemistry* 262(10):4437–4440 (Apr. 5, 1987).

Astermark et al., "Structural Requirements for Ca$^{2+}$ Binding to the γ–Carboxyglutamic Acid and Epidermal Growth Factor–like Regions of Factor IX" *Journal of Biological Chemistry* 266(4):2430–2437 (Feb. 5, 1991).

Baron et al., "The Three–dimensional Structure of the First EGF–like Module of Human Factor IX: Comparison with EGF and TGF–α" *Protein Sci.* 1:81–90 (1992).

Beyer et al., "Purification to Homogeneity of the H Blood Group β–Galactoside αa—2 Fucosyltransferase from Porcine Submaxillary Gland" *Journal of Biological Chemistry* 255(11):5364–5372 (Jun. 10, 1980).

Bjoern et al., "Human Plasma and Recombinant Factor VII" *Journal of Biological Chemistry* 266(17):11051–11057 (Jun. 15, 1991).

Carpenter et al. "Epidermal Growth Factor" *Journal of Biological Chemistry* 265(14):7709–7712 (May 15, 1990).

Chothia, "Domain Association in Immunoglobulin Molecules: The Packing of Variable Domains" *J. Mol. Biol.* 186:651–663 (1985).

Cooke et al., "The Solution Structure of Human Epidermal Growth Factor" *Nature* 327:339–341 (May 28, 1987).

Davis et al., "Acid–dependent Ligand Dissociation and Recycling of LDL Receptor Mediated by Growth Factor Homology Region" *Nature* 326:760–765 (Apr. 23, 1987).

Doolittle, R., "Similar Amino Acid Sequences Revisited" *TIBS* 14:244–245 (Jul. 1989).

Engel, J. "EGF–like Domains in Extracellular Matrix Proteins: Localized Signals for Growth and Differentiation?" *FEBS Letters* 251(1–2):1–7 (Jul. 1989).

Gardell et al., "Isolation, Characterization, and cDNA Cloning of a Vampire Bat Salivary Plasminogen Activator" *Journal of Biological Chemistry* 264(30):17947–17952 (Oct. 25, 1989).

Hallgren et al., "A New Type of Carbohydrate–Protein Linkage in a Glycoprotein from Normal Human Urine" *Journal of Biological Chemistry* 250(14):5312–5314 (Jul. 25, 1975).

Harris et al., "O–Linked Fucose and Other Post–Translational Modifications Unique to EGF Modules" *Glycobiology* 3(3):219–224 (1993).

Harris et al., "O–Linked Fucose is Present in the First Epidermal Growth Factor Domain of Factor XII but Not Protein C" *Journal of Biological Chemistry* 267(8):5102–5107 (Mar. 15, 1992).

Harris et al., "Tissue Plasminogen Activator has an O–Linked Fucose Attached to Threonine–61 in the Epidermal Growth Factor Domain" *Biochemistry* 30:2311–2314 (1991).

Hess et al., "Identification of the Disulfide Bonds of Human Complement C1s" *Biochemistry* 30:2827–2833 (1991).

Huang et al., "Sequence–Specific $^1$H NMR Assignments, Secondary Structure, and Location of the Calcium Binding Site in the First Epidermal Growth Factor Like Domain of Blood Coagulation Factor IX" *Biochemistry* 30:7402–7409 (1991).

Johnson et al., "Purification and properties of the α3/4–L–fucosyltransferase released into the culture medium during the growth of the human A431 epidermoid carcinoma cell line" *Glycoconjugate Journal* 10:152–164 (Apr. 1993).

Jones et al., "Replacing the Complementarity–determining Regions in a Human Antibody with Those From a Mouse" *Nature* 321:522–525 (May 29, 1986).

Kabat, *Sequences of Proteins of Immunological Interest*, US Dept of Health and Human Services, NIH, Bethesda, MD (1991).

Kao et al., "Solution Structure of the EGF–1 Domain from Blood Conagulation Factor VII by NMR Spectroscopy: The Effect of O–Fucosylation" *FASEB Journal* (abstract only) 11(9):A1421 (Jul. 31, 1997).

Kentzer et al. "Carbohydrate Composition and Presence of a Fucose–Protein Linkage in Recombinant Human Pro–Urokinase" *Biochemical and Biophysical Research Communications* 171(1):401–406 (Aug. 31, 1990).

Klinger et al., "Characterization of Novel Amino Acid Fucosides" *Journal of Biological Chemistry* 256(15):7932–7935 (Aug. 10, 1981).

Kohda et al., "Polypeptide Chain Fold of Human Transforming Growth Factor α Analogous to Those of Mouse and Human Epidermal Growth Factors as Studied by Two–Dimensional $^1$H NMR" *Biochemistry* 28:953–958 (1989).

(List continued on next page.)

*Primary Examiner*—Bradley L. Sisson
*Assistant Examiner*—Enrique D. Longton
*Attorney, Agent, or Firm*—Craig G. Svoboda

[57] ABSTRACT

The present invention describes the identification, purification, recombinant production and characterization of novel O-fucosyltransferase enzymes.

6 Claims, 14 Drawing Sheets

OTHER PUBLICATIONS

Kohler et al., "Continuous Cultures of Fused Cells Secreting Antibody of Predefined Specificity" *Nature* 256:495–497 (Aug. 7, 1975).

Kornfeld, S., "Trafficking of Lysosomal Enzymes in Normal and Disease States" *J. Clin. Invest.* 77:1–6 (Jan. 1986).

Kurosawa et al., "A 10–kDa Cyanogen Bromide Fragment from the Epidermal Growth Factor Homology Domain of Rabbit Thrombomodulin Contains the Primary Thrombin Binding Site" *Journal of Biological Chemistry* 263(13):5993–5996 (May 5, 1988).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Munro et al., "A C–Terminal Signal Prevents Secretion of Luminal ER Proteins" *Cell* 48:899–907 (Mar. 13, 1987).

Nagase et al., "Prediction of the Coding Sequences of Unidentified Human Genes. V. The Coding Sequences of 40 New Genes (KIAA0161–KIAA0200) Deduced by Analysis of cDNA Clones from Human Cell Line KG–1" *DNA Research* 3(1):17–24 (1996).

Nishimura et al., "Human Factor IX has a Tetrasaccharide O–Glycosidically Linked to Serine 61 through the Fucose Residue" *Journal of Biological Chemistry* 267(25):17520–17525 (Sep. 5, 1992).

Novotny and Haber, "Structural invariants of antigen binding: comparison of immunoglobulin $V_L$–$V_H$ and $V_L$–$V_L$ domain dimers" *Proc. Natl. Acad. Sci. USA* 82(14):4592–4596 (Jul. 1985).

Paabo et al., "A Short Sequence in the COOH–Terminal Makes an Adenovirus Membrane Glycoprotein a Resident of the Endoplasmic Reticulum" *Cell* 50:311–317 (Jul. 17, 1987).

Patthy, L., "Intron–dependent Evolution: Preferred Types of Exons and Introns" *FEBS Letters* 214(1):1–7 (Apr. 1987).

Paulson et al., "Glycosyltransferases" *Journal of Biological Chemistry* 264(30):17615–17618 (Oct. 25, 1989).

Pelham, H., "Evidence That Luminal ER Proteins Are Sorted From Secreted Proteins in a Post–ER Compartment" *EMBO Journal* 7(4):913–918 (1988).

Presta, L., "Antibody Engineering" *Curr. Op. Struct. Biol.* 2:593–596 (1992).

Riechmann et al., "Reshaping Human Antibodies for Therapy" *Nature* 332:323–327 (Mar. 24, 1988).

Savage et al., "Epidermal Growth Factor: Location of Disulfide Bonds" *Journal of Biological Chemistry* 248(22):7669–7672 (Nov. 25, 1973).

Selander et al., "$^1$H NMR Assignment and Secondary Structure of the $Ca^{2+}$–Free Form of the Amino–Terminal Epidermal Growth Factor Like Domain in Coagulation Factor X" *Biochemistry* 29:8111–8118 (1990).

Sofer et al., "Designing an Optimal Chromatographic Purification Scheme for Proteins" *BioTechniques* 1(4):198–203 (Nov./Dec. 1983).

Sporeno et al., "Oncostatin M Binds Directly to gp130 and Behaves as Interleukin–6 Antagonist on a Cell Line Expressing gp130 but Lacking Functional Oncostatin M Receptors" *Journal of Biological Chemistry* 269(15):10991–10995 (Apr. 15, 1994).

Staudacher et al., "Functional purification and characterization of a GDP–fucose: β–N–acetylglucosamine (Fuc to Asn linked GlcNAc) α1,3–fucosyltransferase from mung beans" *Glycoconjugate Journal* 12:780–786 (Dec. 1995).

Stenflo, J., "Structure–Function Relationships of Epidermal Growth Factor Modules in Vitamin K–Dependent Clotting Factors" *Blood* 78(7):1637–1651 (Oct. 1, 1991).

Tappin et al., "A High–resolution $^1$H–NMR Study of Human Transforming Growth Factor β" *European Journal of Biochemistry* 179:629–637 (1989).

Ullner et al., "Three–Dimensional Structure of the Apo Form of the N–Terminal EGF–like Module of Blood Coagulation Factor X as Determined by NMR Spectroscopy and Simulated Folding" *Biochemistry* 31(26):5974–5983 (1992).

von Figura et al., "Lysosomal Enzymes and Their Receptors" *Ann. Rev. Biochem.* 55:167–193 (1986).

Voynow et al., "Purification and Characterization of GDP–L–fucose–N–acetyl β–D– glucosaminide α1→6Fucosyltransferase from Cultured Human Skin Fibroblasts" *Journal of Biological Chemistry* 266(32):21572–21577 (Nov. 15, 1991).

Wang et al., "Identification and Purification of a GDP–Fucose: Polypeptide Fucosyltransferase" *Glycobiology* (abstract only) 6(7):11.02 (Oct. 1996).

Wang et al., "Identification of a GDP–L–fucose: polypeptide fucosyltransferase and enzymatic addition of O–linked fucose of EGF domains" *Glycobiology* 6(8):837–842 (Dec. 1996).

Wang et al., "Purification and Molecular Cloning of a GDP–Fucose: Polypeptide Fucosyltransferase Specific for EGF Domain Glycosylation" *Glycobiology* (abstract only) 7(7):75 (Oct. 1997).

Wells et al., "Cassette Mutagenesis: an Efficient Method for Generation of Multiple Mutations at Defined Sites" *Gene* 34(2–3):315–323 (1985).

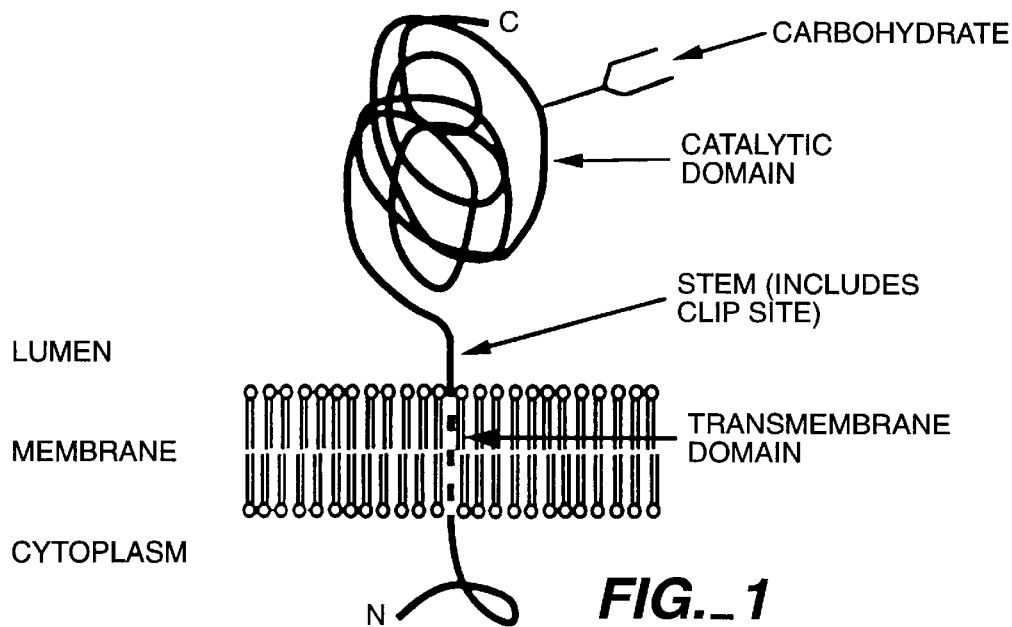
FIG._1
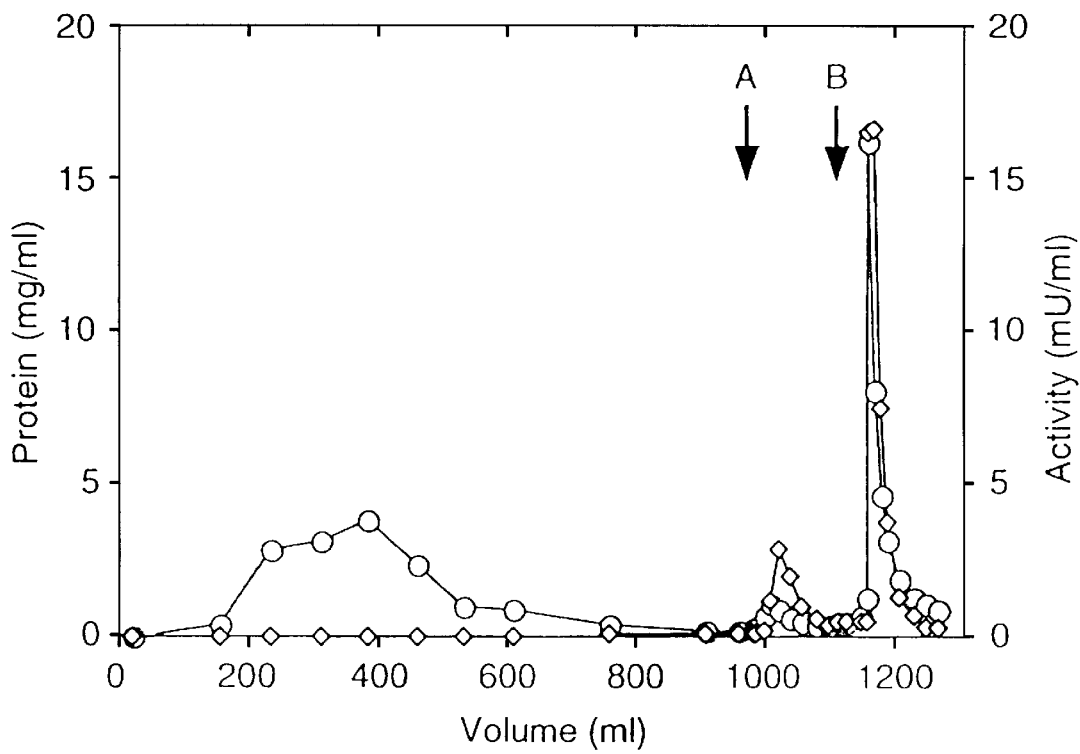
FIG._2

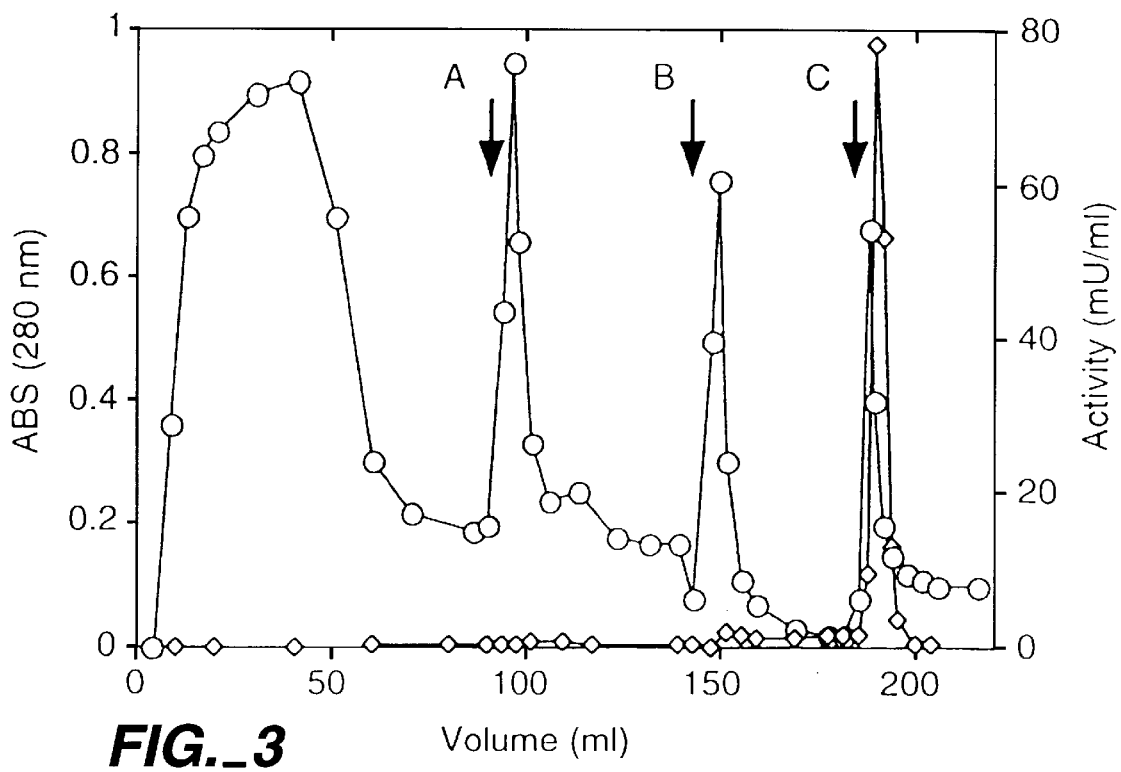
FIG._3
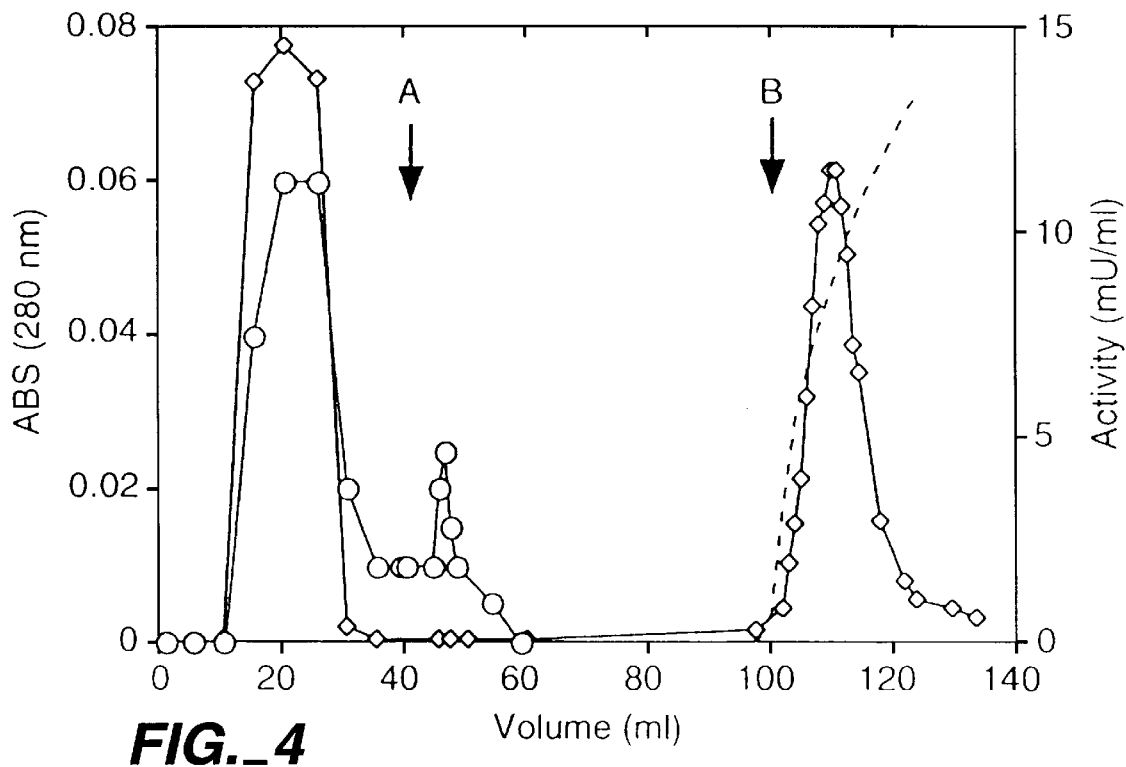
FIG._4

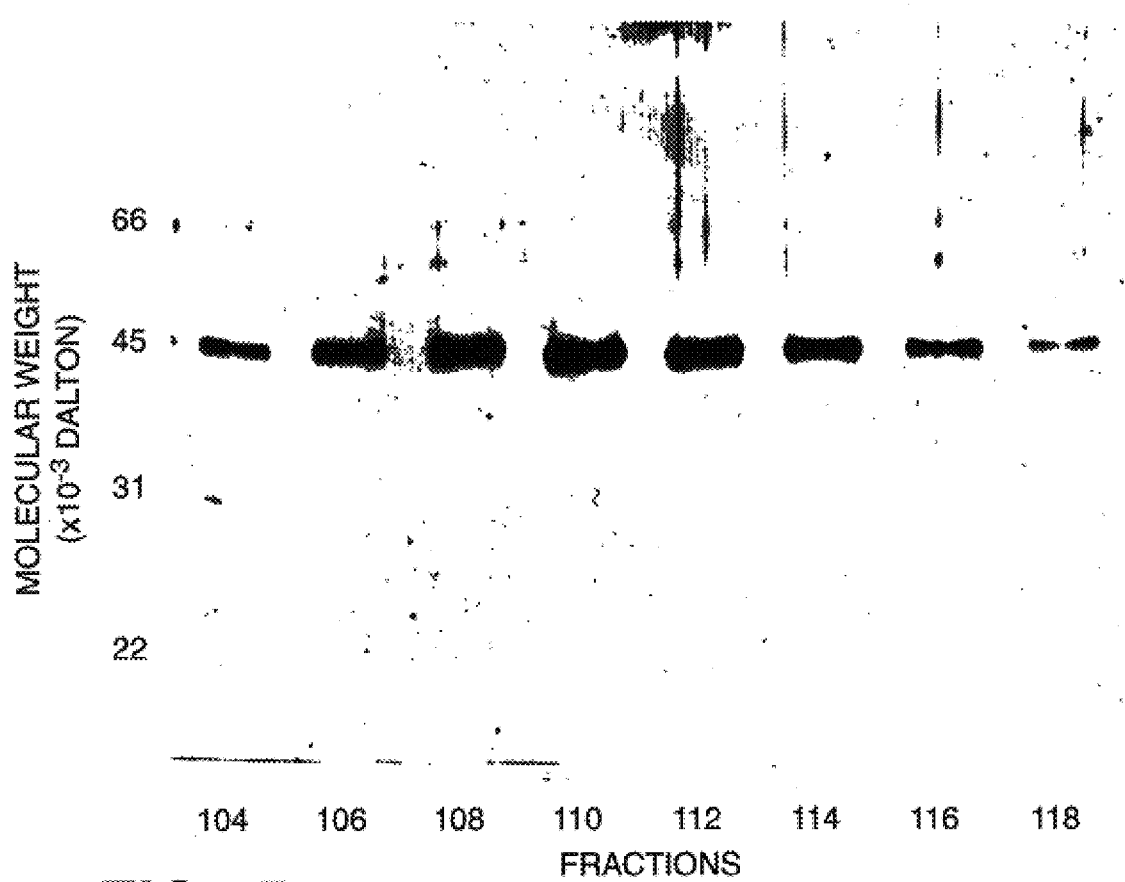
FIG._5
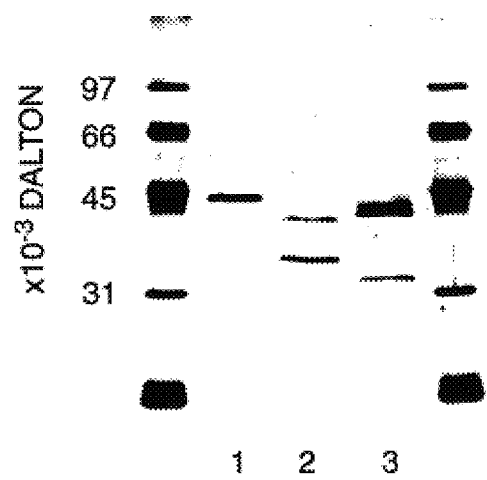
FIG._6

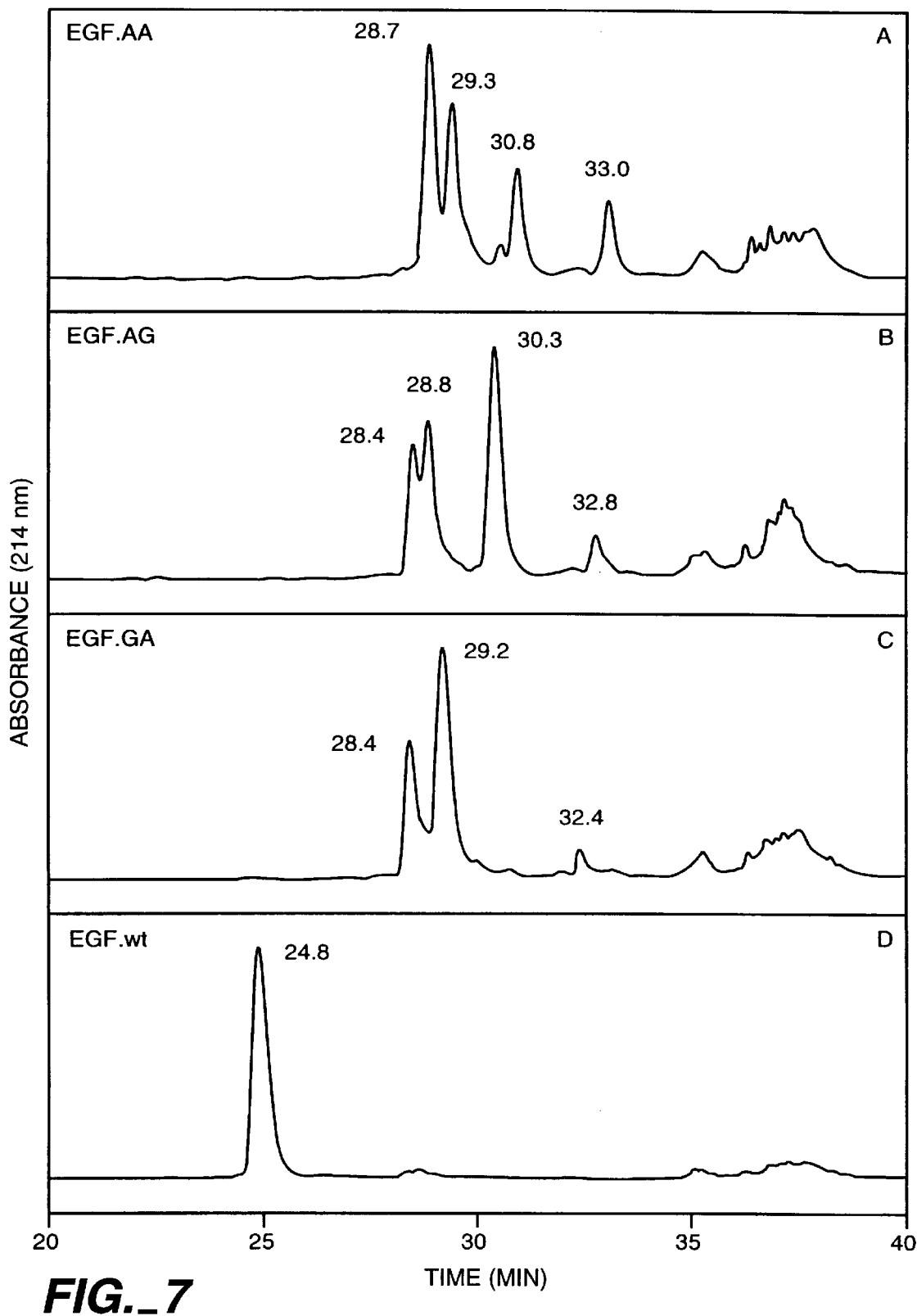
FIG._7

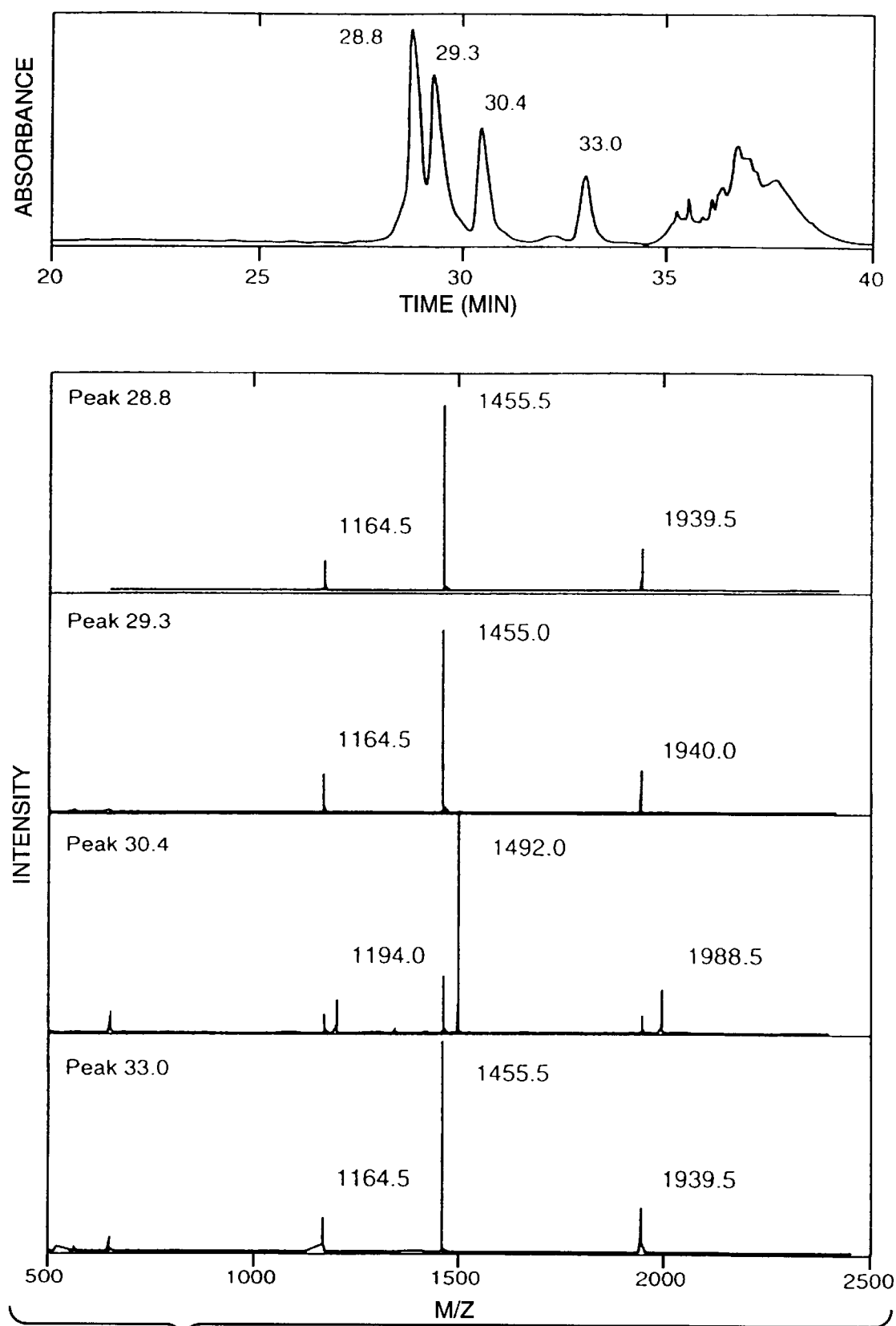
FIG._8

| | | |
|---|---|---|
| C. ELEGANS | 1 | MSNYRYSKLNEEEISLEDMPSSANQILTRQEQIIQEQDDELELVGNSVRT |
| C. ELEGANS | 51 | LRGMSSMIGDELDQQSTMLDDLGQEMEYSETRLDTAMKKMAKLTHLEDGM |
| CHO | 1 | — — — — — — — — — — — — — — — — — — — — — — — — — — — — — — — — — — — — — — — — — — — — — — RLA |
| C. ELEGANS | 101 | LLARRIVQSMQNDHGALSSPVFPRLCPSGLTTYVPYIVDFSSLTFHIFII |
| CHO | 4 | GSWDLAGTLLYXPXMGRFGNQADHFLGSLAFAKLXVRTLAVPPWIEYQHH |
| HUMAN | 1 | — — — — — — — — — — — — — NQADHFLGSLAFAKLLNRTLAVPPWIEYQHH |
| C. ELEGANS | 151 | IHIIIDFCSQSQSKGRFGNQVDQFLGVLAFAKALDRTLVLPNFIEFKHP |
| CHO | 54 | — — — — — — — — — — — — — — — — — — — — — — — — — — — — — — — — — — — — — — — — — — — — — — — — |
| HUMAN | 32 | KPPFTNLH — — — — — — — — — — — — — — — — — — — — — — — — — — — — — — — — — — — — — — — — — — — — |
| C. ELEGANS | 201 | ETKMIPFEFLFQVG — — KYFKLEPLQAYHRVISLEDFMEKLAPTHWPPEKRVAYC |
| HUMAN | 82 | FEVAAQRSPDKKTCPMKEGNPFGPFWDQFHVSFNKSELFTGIHSFSASYRE |
| C. ELEGANS | 247 | DKSAEPGCHSK — — — — EGNPFGPYWDQIDVSFVGDEYFGDIPGGFDLNQ |
| HUMAN | 132 | QWSQR — — — FSPKEHPVLALPGAPAQFPVLEEHRPLQKYMVWSDEMVKT |
| C. ELEGANS | 291 | MGSRKKWLEKFPSEEYPLAFSSAPAPFPSKGKVWSIQKYLRWSSRITEQ |
| HUMAN | 177 | GEAQIHAHLVRPYVGIHLRIGSDWKNACAMLKDGTAGSHFMASPQCVGYS |
| C. ELEGANS | 341 | AKKFISANLAKPFVAVHLRNDADWVRVCEHIDTTNRPLFASEQCLG — — |
| HUMAN | 227 | RSTAAPLTMTMCLPDLKEIQRAVKLWVRSLDAQSVYVATDSESYVPELQQ |
| C. ELEGANS | 388 | — — — — — — — — — — — — — — — — — — — — — — — EGHHLGTLTKEICSPSKQ |
| HUMAN | 277 | LFKGKVKVVSLKPEVAQVDLYILGQADHFIGNCVSSFTAFVKRERDLQGR |
| C. ELEGANS | 406 | QILEQIEAHRQEPDDMYTSLAIMGRADLFVGNCVSTFSHIVKRERDHAGQ |
| HUMAN | 327 | PSSFFGMDRPPKLRDEF — — |
| C. ELEGANS | 456 | SPRPSAFFGIRAVKRHIDL |

FIG._9

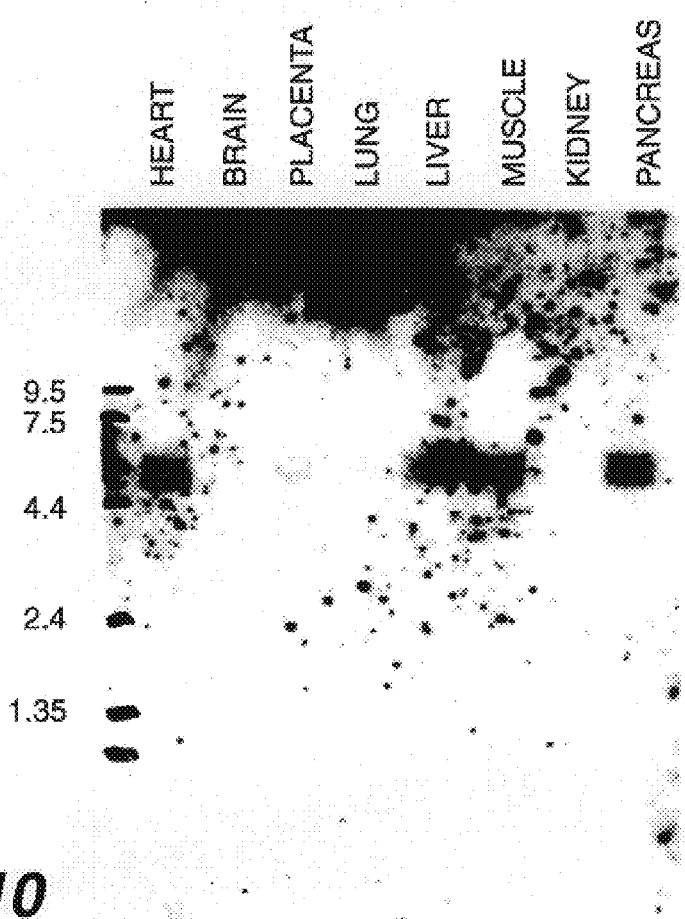
FIG._10
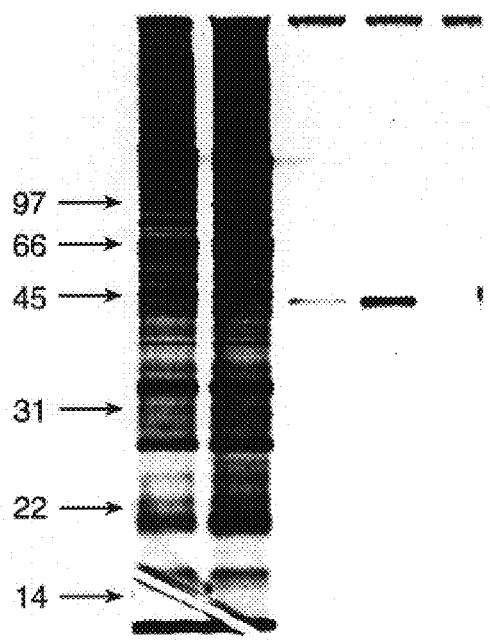
FIG._15

```
GAACCAGGCC GATCACTTCT TGGCTCTCT GGCATTTGCA AAGCTGCTAA ACCGTACCTT GGCTGTCCCT CCTTGGATTG AGTACCAGCA TCACAAGCCT
CTTGGTCCGG CTAGTGAAGA ACCGAGAGA CCGTAAACGT TTCGACGATT TGGCATGGAA CCGACAGGGA GGAACCTAAC TCATGGTCGT AGTGTTCGGA
CCTTTCACCA ACCTCCATGT GTCCTACCAG AAGTACTTCA AGCTGGAGCC CCTCCAGGCT TACCATCGGG TCATCAGCTT GGAGGATTTC ATGGAGAAGC
GGAAAGTGGT TGGAGGTACA CAGGATGGTC TTCATGAAGT TCGACCTCGG GGAGGTCCGA ATGGTAGCCC AGTAGTCGAA CCTCCTAAAG TACCTCTTCG
TGGCACCCAC CCACTGGCCC CCTGAGAAGC GGGTGGCATA CTGCTTTGAG GTGGCAGCCC AGCGAAGCCC AGATAAGAAG ACGTGCCCCA TGAAGGAAGG
ACCGTGGGTG GGTGACCGGG GGACTCTTCG CCCACCGTAT GACGAAACTC CACCGTCGGG TCGCTTCGG TCTATTCTTC TGCACGGGGT ACTTCCTTCC
AAACCCCTTT GGCCCATTCT GGGATCAGTT TCATGTGAGT TTCAACAAGT CGGAGCTTTT TACAGGCATT TCCTTCAGTG CTTCCTACAG AGAACAATGG
TTTGGGGAAA CCGGGTAAGA CCCTAGTCAA AGTACACTCA AAGTTGTTCA GCCTCGAAAA ATGTCCGTAA AGGAAGTCAC GAAGGATGTC TCTTGTTACC
AGCCAGAGAT TTTCTCCAAA GGAACATCCG GTGCTTGCCC CCCAGCCCAG TTCCCCGTCC TAGAGGAACA CAGGCCACTA CAGAAGTACA
TCGGTCTCTA AAAGAGGTTT CCTTGTAGGC CACGAACGGG GGGTCGGGTC AAGGGGCAGG ATCTCCTTGT GTCCGGTGAT GTCTTCATGT
TGGTATGGTC AGACGAAATG GTGAAGACGG GAGAGGCCCA GATTCATGCC CACCTTGTCC GGGCATTCAT GGGCCTATGT GCTCTGACTG
ACCATACCAG TCTGCTTTAC CACTTCTGCC CTCTCCGGGT CTAAGTACGG GTGGAACAGG CCCGTAAGTA GACGCGTAAC CGAGACTGAC
GAAGAACGCC TGTGCCATGC TGAAGGACGG GACTGCAGGC GACTGCAGGC GGGCTGTGAA TGGCCTCTCC ACCGGAGAGG GCTCTGGGTG
CTTCTTGCGG ACACGGTACG ACTTCCCTGC CTGACGTCCG AGCCGTGAAGT ACCGGAGAGG CGTCACACAC CCGATGTCCG CGTCGTGTCG
ACGATGACTA TGTGCCTGCC TGACCTGAAA GAGATCCAGA GGGCTGTGAA ATGCCCAGTC AGGTCGCTGG ATGCCCAGTC GGTCTACGTT GCTACTGATT
TGCTACTGAT ACACGGACGG ACTGGACTTC CTCTAGGTCT CCCGACACTT CAGAGACCAC TCCAGGTCAG TCCAGGTCAG TACGGGTCAG CGATGACTAA
CCGAGAGTTA TGTGCCTGAG CTCCAACAGC TCTTCAAAGG GAAGGTGAGC GTGGTGAGCC TGAAGCCTGA GGTGGCCCAG GTCGACCTGT ACATCCTCGG
GGCTCTCAAT ACACGGACTC GAGGTTGTCG AGAAGTTTCC CTTCCACTTC CACCACTGG ACTTCGGACT CCACCGGGTC CAGCTGGACA TGTAGGAGCC
CCAAGCCGAC CACTTTATTG GCAACTGTGT CTCCTCCTTC ACTGCCTTTG TGAAGCGGGA GCGGGACCTC CAGGGAGGC CGTCTTCTTT CTTCGGCATG
GGTTCGGCTG GTGAAATAAC CGTTGACACA GAGGAGGAAG TGACGAAAC ACTTCGCCCT CGCCCCTGGAG GTCCCCTCCG GCAGAAGAAA GAAGCCGTAC
```

FIG._11A

```
GACAGGCCCCC CTAAGCTGCG GGACGAGTTC TGATTCTGGC CGGAGCACCA GACCCTCTGA TCCTGGAGGG ACCAGAGTCT GAGCTGGTCC TTCCAGCCAG
CTGTCCGGGG GATTCGACGC CCTGCTCAAG ACTAAGACCG GCCTCGTGGT CTGGGAGACT AGGACCTCCC TGGTCTCAGA CTCGACCAGG AAGGTCGGTC
GCCTGGCAGC CAGAGGTGCT CCGGGATTGC AAACTCCTCT TCTCACCTGC CAAAGATGGA GAAGAGTGCC AGGGACCCCT CAAGGAGGAA GACGCTCCAT
CGGACCGTCG GTCTCCACGA GGCCCTAACG TTTGAGGAGA AGAGTGGACG GTTTCTACCT CTTCTCACGG TCCCTGGGGA GTTCCTCCCT CTGCGAGGTA
ATCCCAGGGC ATAGGACTTG CAGGTTCCTA GGAGCAGGAG CATCTCCCAT CGCACGTGCT TTCTGCTCTT CTGGGAATTT CTCACACTGG CAAAGCAGTC
TAGGGTCCCG TATCCTGAAC GTCCAAGGAT CCCTCGTCCT GTAGAGGGTA GCGTGCACGA AAGACGAGAA GACCCTTAAA GAGTGTGACC GTTTCGTCAG
CAGCCTCCGT CTTCTGGTCC ACTCTGCTCT GAGCAGCCTG GGATGCTGAA CTCTTCAGAG CTCTTCAGAG AGATTTTTTT ATAGAGAGAT TTCTATAAATT TTGATACAAG
GTCGGAGGCA GAAGACCAGG TGAGACGAGA CTCGTCCGAC CCTACGACTT GAGAAGTCTC TCTAAAAAAA TATCTCTCTA AAGATATTAA AACTATGTTC
GTCATGACTA TCCTAGAACT CTCTGTGGTT TTTGAAAATC ATTGAATTC
CAGTACTGAT AGGATCTTGA GAGACACCAA AAACTTTTAG TAACTTAAG
```

*FIG._11B*

```
  1  ATGCCCGCGG GCTCCTGGGA CCCGGCCGGT TACCTGCTCT ACTGCCCCTG CATGGGGCGC TTTGGAAACC AGGCCGATCA CTTCTTGGGC TCTCTGGCAT
  1   M  P  A  G  S  W  D  P  A  G  Y  L  L  Y  C  P  C  M  G  R  F  G  N  Q  A  D  H  F  L  G  S  L  A  F

101  TTGCAAAGCT GCTAAACCGT ACCTTGGCTG TCCCTCCCTG GATTGAGTAC CAGCATCACA AGCCTCCTTT CACCAACCTC CATGTGTCCT ACCAGAAGTA
 35   A  K  L  L  N  R  T  L  A  V  P  P  W  I  E  Y  Q  H  H  K  P  P  F  T  N  L  H  V  S  Y  Q  K  Y

201  CTTCAAGCTG GAGCCCCTCC AGGCTTACCA TCGGGTCATC AGCTTGGAGG ATTTCATGGA GAAGCTGGCA CCCACCCACT GGCCCCCTGA GAAGCGGGTG
 68   F  K  L  E  P  L  Q  A  Y  H  R  V  I  S  L  E  D  F  M  E  K  L  A  P  T  H  W  P  P  E  K  R  V

301  GCATACTGCT TTGAGGTGGC AGCCCAGCGA AGCCCAGATA AGAAGACGTG CCCCATGAAG GAAGAAACC CCTTGGCCC ATTCTGGGAT CAGTTTCATG
101   A  Y  C  F  E  V  A  A  Q  R  S  P  D  K  K  T  C  P  M  K  E  G  N  P  F  G  P  F  W  D  Q  F  H  V

401  TGAGTTTCAA CAAGTCGGAG CTTTTTACAG GCATTCCCTT CAGTGCTTCC TACAGAGAAC AATGGAGCCA GTACATGGTA TGGTCAGACG AAATGGTGAA GACGGGAGAG
135   S  F  N  K  S  E  L  F  T  G  I  S  F  S  A  S  Y  R  E  Q  W  S  Q  Y  M  V  W  S  D  E  M  V  K  T  G  E

501  TGCCCTGCCA GGAGCCCCAG CCCAGTTCCC CGTCCTAGAA GAACACAGGC CACTACAGAA TGGTCAGATGTA GACGGGACTG
168   A  L  P  G  A  P  A  Q  F  P  V  L  E  E  H  R  P  L  Q  K  Y  M  V  W  S  D  E  M  V  K  T  G  E

601  GCCCAGATTC ATGCCCACCT TGTCCGGCCC TATGTGGGCC TTCATCTGCG CATTGGCTCT GACTGGAAGA ACGCCTGTGC CATGCTGAAG GACGGGACTG
201   A  Q  I  H  A  H  L  V  R  P  Y  V  G  I  H  L  R  I  G  S  D  W  K  N  A  C  A  M  L  K  D  G  T  A

701  CAGGCTCGCA CTTCATGGCC TCTCCGCAGT GCAGCCGCAGC CAGTCGGTCT GGCTATGTGC CCCTCACGAT GACTATGTGC CTGCCTGACC TGAAGGAGAT
235   G  S  H  F  M  A  S  P  Q  C  S  R  S  T  A  A  P  L  T  M  T  M  C  L  P  D  L  K  E  I

801  CCAGAGGGCT GTGAAGCTCT GGGTGAGGTC GCTGGATGCC CAGTCGGTCT ACGTTGCTAC TGATTCCGAG AGTTATGTGC CTGAGCTCCA ACAGCTCTTC
268   Q  R  A  V  K  L  W  V  R  S  L  D  A  Q  S  V  Y  V  A  T  D  S  E  S  Y  V  P  E  L  Q  Q  L  F

901  AAAGGAAGG TGAAGGTGGT GAGCCTGAAG CCTGAGGTGG CCCAGGTCGA CCTGTACATC CTCGGCCAAG CCGACCACTT TATTGGCAAC TGTGTCTCCT
301   K  G  K  V  K  V  V  S  L  K  P  E  V  A  Q  V  D  L  Y  I  L  G  Q  A  D  H  F  I  G  N  C  V  S  S
```

*FIG._12A-1*

```
1001  CCTTCACTGC CTTTGTGAAG CGGGAGCGGG ACCTCCAGGG GAGGCCGTCT TCTTTCTTCG GCATGACAGG GCCCCCTAAG CTGCGGGACG AGTTCTGATT
335    F  T  A   F  V  K   R  E  R  D   L  Q  G   R  P  S   F  F  F  G   M  D  R    P  P  K   L  R  D  E    F  O
1101  CTGGCCGGAG CACCAGACCC TCTGATCCTG GAGGGACCAG AGTCTGAGCT GGTCCTTCCA GCCAGGCCTG GTGCTCCGGG ATTGCAAACT
1201  CCTCTTCTCA CCTGCCAAAG ATGGAGAAGA GTGCCAGGGA CCCCTCAAGG AGGGAGACGC TCCATATCCC AGGGCATAGG ACTTGCAGGT TCCTAGGAGC
1301  AGGAGCATCT CCCATCGCAC GTGCTTTCTG CTCTTCTCTG GG AATTTCCAC ACTGGCAAAG CAGTCCAGCC TCCGTCTTCT GGTCCACTCT GCTCTGAGCA
1401  GCCTGGGATG CTGAACTCTT CAGAGAGATT TTTATAGA GAGATTTCTA TAATTTGAT ACAAGGTCAT GACTATCCTA GAACTCTCTG TGGTTTTTGA
1501  AAATCATTGA ATTC
```

FIG._12A-2

```
Human  MPAGSWDPAGYLLYCPCMGRFGNQADHFLGSLAFAKLLNRTLAVPPWIEYQHHKPPFTNLH
       *****  ******  *  ************************  ****************
CHO    RLAGSWDLAGYLLYXPXMGRFGNQADHFLGSLAFAKLXVRTLAVPPWIEYQHHKPPFTNLH
              10         20         30         40         50         60
```

FIG._12B

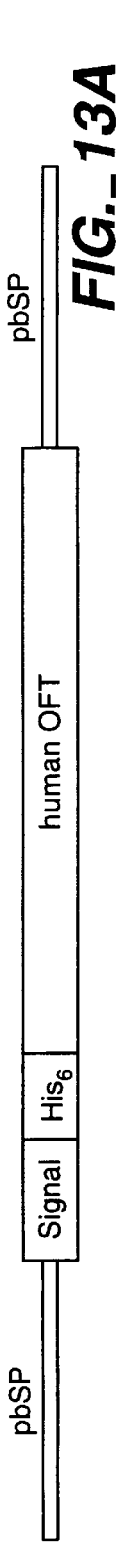

```
5001 ACGATGACTA TGTGCCTGCC TGACCTGAAG GAGATCCAGA GGGCTGTGAA GCTCTGGGTG AGGTCGCTGG ATGCCCAGTC GGTCTACGTT GCTACTGATT
 288  T  M  T   M  C  L  P   D  L  K   E  I  Q  R   A  V  K    L  W  V    R  S  L  D   A  Q  S   V  Y  V    A  T  D  S

5101 CCGAGAGTTA TGTGCCTGAG CTCCAACAGC TCTTCAAAGG GAAGGTGAAG GTGGTGAGCC TGAAGCCTGA GGTGGCCCAG GTCGACCTGT ACATCCTCGG
 322  E  S  Y   V  P  E   L  Q  Q  L   F  F  K  G   K  V  K    V  V  S  L   K  P  E    V  A  Q    V  D  L  Y   I  L  G

5201 CCAAGCCGAC CACTTTATTG GCAACTGTGT CTCCTCCTTC ACTGCCTTTG TGAAGCGGGA GCGGGACCTC CAGGGGAGGC CGTCTTCTTT CTTCGGCATG
 355  Q  A  D    H  F  I  G   N  C  V    S  S  F    T  A  F  V   K  R  E    R  D  L    Q  G  R  P    S  S  F    F  G  M

5301 GACAGGCCCC CTAAGCTGCG GGACGAGTTC TGATTCTGGC CGGAGCACCA GACCCTCTGA TCCTGGAGGG ACCAGAGTCT GAGCTGGTCC TTCCAGCCAG
 388  D  R  P  P   K  L  R    D  E  F   0
```

FIG._13B-2

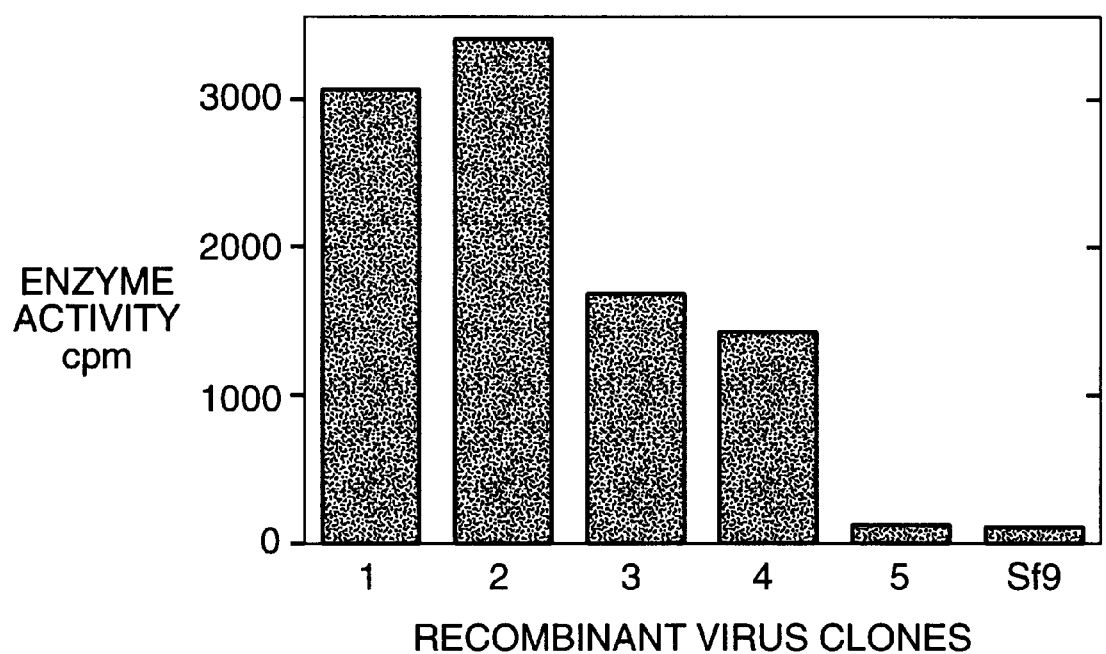
FIG._14

O-FUCOSYLTRANSFERASE

This application is a continuation-in-part of U.S. patent application Ser. No. 08/792,498, filed Jan. 31, 1997, now abandonded.

BACKGROUND

The present invention relates to the field of glycosyltransferases, or enzymes which transfer sugar residues from an activated donor substrate to an amino acid or growing carbohydrate group.

Glycosyltransferases that are involved in the biosynthesis of glycoprotein and glycolipid sugar chains are resident membrane proteins of the endoplasmic reticulum and the Golgi apparatus. They are responsible for catalysis of the addition of monosaccharide units either to an existing glycan chain or to a peptide or lipid acceptor initiating a chain. Donor monosaccharides are typically utilized in activated form, either as a nucleotide sugar, e.g. GDP-mannose or, less frequently, as a lipid-linked donor, e.g., dolichol-P-glucose (Dol-P-Glc). The majority of glycosyltransferases are lumenally oriented, i.e. with the catalytic domain within a membrane-bounded compartment. Examples of lumenally oriented enzymes are galactosyltransferases and sialyltransferases. Their structure is pictorially represented in FIG. 1. The enzymes are typically grouped into families based on the type of sugar they transfer (galactosyltransferases, sialyltransferases, etc.). Comparisons amongst known cDNA clones of glycosyltransferases (Paulson, J. C. & Colley, K. J., *J. Biol. Chem.* 264 (30), 17615–618 (1989), has revealed that there is very little sequence homology between the enzymes. However, as indicated by FIG. 1, all glycosyltransferases share some common structural features: a short $NH_2$-terminal cytoplasmic tail, a 16–20 amino acid signal-anchor domain, and an extended stem region which is followed by the large COOH-terminal catalytic domain. The signal anchor domains act as both uncleavable signal peptides and as membrane-spanning regions and orient the catalytic domains of these glycosyltrarisferases within the lumen of the Golgi apparatus.

The means by which cells regulate the expression of specific carbohydrate sequences is of great interest because of increasing evidence that cell surface carbohydrate groups mediate a variety of cellular interactions during development, differentiation, and oncogenic transformation. von Figura, K. & Hasilik, A., *Annu. Rev. Biochem.* 55, 167–193 (1986); Komfield, S., *J. Clin. Invest.* 77, 1–6 (1986); Munro, S. & Pelham, H.R.B., *Cell* 48, 899–907 (1987); Pelham, H. R. B., *EMBO J.* 7, 913–918 (1988); Paabo, S. et al., *Cell* 50, 311–317 (1987). It is estimated that at least one hundred (100) glycosyltransferases are required for the synthesis of known carbohydrate structures on glycoproteins and glycolipids, and most of these are involved in elaborating the highly diverse terminal sequences. Paulson, J. C. & Colley, K. J., *J. Biol. Chem.* 264 (30), 17615–618 (1989). Among those enzymes responsible for terminal elaborations, three (3) enzymes have been of particular interest: galactosyltransfereases, fucosyltransferases and sialyltransferases.

Fucosyltransferases transfer the sugar fucose from UDP in α1-2, α1-3, α1-4 and α1-6 linkages. Fucose was first identified as being present in glycosidic linkages to serine or threonine as compounds of the type Glcb1→3Fuca1→O-Ser/Thr and Fuca1→O-Ser/Thr in human urine and rat tissue. Hallgren, P. et al., *J. Biol. Chem.* 250, 5312–5314 (1975); Klinger, M. M. et al.,*J. Biol. Chem.* 256, 7932–7935 (1981). The identification of O-linked fucose attached to a specific protein was first made by Kentzer at al. who found a residue of fucose covalently linked to a peptide derived from the epidermal growth factor (EGF) domain of recombinant urokinase. Kentzer, E. J. et al., *Biochem. Biophys. Res. Commun.*, 171, 401–406 (1990). Similar glycosylation patterns have been found in tissue plasminogen activator (tPA) (Harris, R. J. & Spellman, M. W., *Biochemistry* 30, 2311–14 (1991)), human factor VII (Bjoern et al. 266, 11051–11057 (1991)), human factor XII, (Harris et al., *J. Biol. Chem.*, 267, 5102–5107 (1992)) and vampire bat plasminogen activator, Gardell et al, J. Biol. Chem. 264, 17947–52 (1989). The EGF domain of human factor IX has also been indicated to have O-fucosylation, but at the reducing end of the tetrasaccharide: NeuAca2→6Galb1→4GlcNAcb1→3Fuca1→O-Ser61. Nishimura et al., *J. Biol. Chem.*, 267, 17520–17525 (1992); Harris et al., *Glycobiology* 3, 219–224 (1993). However, in all cases in which it has been detected, O-linked fucose is present within the sequence Cys-Xaa-Xaa-Gly-Gly-Ser/Thr-Cys. Harris et al., *Glycobiology* 3, 219–224 (1993).

EGF is a potent 53 amino acid mitogen which has its activity mediated by binding to the EGF receptor. Carpenter, G and Cohen, C, *J. Biol. Chem.* 265, 7709–7712 (1990). Regions of EGF sequence homology have been found in an every-increasing number of coagulation, fibrinolytic, complement and receptor proteins. Panthy, L., *FEBS Lett.* 214, 1–7 (1987); Doolittle, R. F., *Trends Biochem. Sci.* 14, 244–245 (1989). The EGF modules of these multi-modular proteins are not believed to interact with the EGF receptor. Rather, different properties have been ascribed to such EGF modules, including ligand binding (Appella et al., *J. Biol. Chem.* 262, 4437–4440 (1987); Kurosawa et al., *J. Biol. Chem.* 263, 5993–5996 (1988), mitogenic activity (Engel, *FEBS Lett.* 251, 1–7 (1989) and receptor recycling (Davis et al., *Nature* 326, 760–765 (1987). The EGF modules of the vitamin K-dependent coagulation proteins are required for the proper folding of adjacent modules containing γ-carboxylglutamic acid residues (Astermark et al., *J. Biol. Chem.* 266, 2430–2437 (1991), while others may simply serve as spacers between different functionally active regions (Stenflo, J., *Blood* 78, 1637–1651 (1991).

EGF domains are characterized by the presence of six (6) conserved cysteine residues that are expected to form three (3) intrachain disulfide bonds in the 1-3, 2-4 and 5-6 pattern obtained for EGF. Savage et al., *J. Biol. Chem.* 248, 7669–7672 (1973). A similar disulfide-binding pattern has been confirmed for the EGF domain of human complement protein Cls, Hess et al., *Biochemistry* 30, 2827–2833 (1991). Three dimensional solution structures of synthetic comprising individual N-terminal EGF modules of human factors X and IX have been obtained by NMR spectroscopic studies (Selander et al., *Biochemistry* 29, 8111–8118 (1990); Huang et al., *Biochemistry* 30, 7402–7409 (1991); Baron et al., *Protein Sci.* 1, 81–90 (1992); Ullner et al., *Biochemistry* 31, 5974–5983 (1992). The derived structures are almost identical to those determined for EGF (Cooke et al, *Nature* 327, 339–341 (1987) and TGF-α (Kohda et al, *Biochemistry* 28, 953–958 (1989); Tappin et al., *Eur. J. Biochem.* 179, 629–637 (1989).

There is an intense interest in the synthesis of proteins which contain O-fucose in glycosidic linkages. This is especially true in proteins with EGF domains which are O-fucosylated. In order to properly and efficiently O-fucosylate these proteins, an enzyme specific to creating O-fucose linkages would be highly desirable. However, as previous attempts to isolate and purify O-fucosyltransferase have proved to be unsuccessful, there exists a great need for highly pure, homogeneous O-fucosyltransferase as well as an efficient detection assay.

SUMMARY

The present invention describes identification, recombinant production and the characterization of novel O-fucosyltransferase enzymes. More specifically, the present invention describes the isolation of cDNAs encoding various forms of O-fucosyltransferase and to the expression and characterization of O-fucosyltransferases.

In one aspect, the present invention relates to substantially pure O-fucosyltransferase, including an amino acid sequence substantially identical to the sequence shown in FIG. 12A [SEQ ID NO:2]. In the preferred embodiment, substantially pure O-fucosyltransferase is obtained from mammalian (eg, human, hamster) sources.

In another aspect, the present invention relates to a substantially pure O-fucosyltansferase which is capable of glycosylating the EGF domain of a peptide with an activated O-fucose moiety. In a more limited aspect, the present invention relates to a substantially pure O-fucosyltransferase which is capable of glycosylating the sequence -Cys-Xaa-Xaa-Xaa-Xaa-Ser/Thr-Cys-. In yet a more limited aspect, the sequence is -Cys-Xaa-Xaa-Gly-Gly-Ser/Thr-Cys-.

In a related aspect, the present invention relates to functional fragment or analog of O-fucosyltransferase including an amino acid sequence substantially identical to the sequence shown in FIG. 12B. [SEQ ID NO:9]. In a more limited aspect, this functional fragment or analog is capable of glycosylating the sequence -Cys-Xaa-Xaa-Xaa-Xaa-Ser/Thr-Cys-. In yet a more limited aspect, the sequence is Cys-Xaa-Xaa-Gly-Gly-Ser/Thr-Cys.

In another aspect, the invention relates to substantially pure DNA having a sequence substantially identical to the nucleotide shown in FIG. 12A [SEQ ID NO:1] wherein such DNA encodes a protein capable of glycosylating the EGF domain of a polypeptide. In a more limited aspect, this DNA is capable of glycosylating the sequence -Cys-Xaa-Xaa-Xaa-Xaa-Ser/Thr-Cys-. In yet a more limited aspect, the sequence is Cys-Xaa-Xaa-Gly-Gly-Ser/Thr-Cys.

In yet another aspect, the invention relates to antibodies which are capable of binding to O-fucosyltransferase, including the sequence of FIG. 12A [SEQ ID NO:1]. These antibodies may be polyclonal, monoclonal, humanized, bispecific or heterospecific.

In still another aspect, the invention relates to a method of placing an O-fucose onto an EGF domain of a polypeptide. In a more limited aspect the glycosylated sequence is -Cys-Xaa-Xaa-Xaa-Xaa-Ser/Thr-Cys-. In yet a more limited aspect, the sequence is Cys-Xaa-Xaa-Gly-Gly-Ser/Thr-Cys.

In still another aspect, the invention relates to a method or assay for detecting the presence of O-fucosyltransferase comprising the steps of:
 a) preparation of extract from a cell line expressing O-fucosyltransferase;
 b) first chromatography purification over an anion exchange resin and nucleotide binding resin;
 c) second chromatography purification over an acceptor substrate ligand associated with a metal chelating-agarose resin;
 d) third chromatography purification over a donor substrate analog ligand associated with agarose.

In still another aspect, the invention relates to inhibitors of O-fucosyltransferase and to a method of their use in the treatment of diseases mediated by proteins having their efficacy determined at least in part by the presence of O-linked fucose.

Other aspects of the invention will become apparent from the following detailed description and the claims.

BRIEF DESCRIPTION OF THE DRAWINGS

In FIGS. 2–4, one unit corresponds to 1 $\mu$mol of fucose transferred per minute.

FIG. 1 represents graphically the structure of glycosyltransferases, illustrating the catalytic domain, stem and transmembrane domain, in relation to the cytoplasm, membrane and lumen of the cell.

FIG. 2 represents a chromatograph over a DE-52/Affi-Gel blue combined column. Open circles represent protein concentration and open diamonds represent enzyme activity. At point A, the DE-52 column was detached and the Affi-Gel Blue column was washed with buffer containing 125 mM NaCl. Elution of the enzyme started at Point B, with buffer containing 1 M NaCl.

FIG. 3 represents a chromatograph over a column of affinity resin attached to the acceptor substrate, which here was Factor VII EGF-1-His$_6$-Ni$^{2+}$NTA-Agarose. Open diamonds represent enzyme activity and open circles represent protein concentrations as monitored at 280 nm. At Point A and B, the column was washed with buffers containing 0.5 M NaCl and 25 mM imidazole. The enzyme and Factor VII EGI domain were eluted together at Point C with 0.3 M imidazole.

FIG. 4 represents a chromatograph over a column of affinity resin attached to a donor substrate analog, which here was GDP-hexanolamine-agarose. Open circles represent protein concentration as monitored at 280 nm, and open diamonds represent enzyme activity. The dashed line indicates the 0–2 mm GDP gradient used for elution (monitored at 280 nm, scale not shown). After the sample was loaded, the column was washed with equilibration buffer and equilibration buffer containing 125 mM NaCl, which is represented as Point A. The elution of enzyme began at Point B.

FIG. 5 represents an SDS-PAGE gel of O-fucosyltransferase prepared by affinity chromatography. Each column shows the protein detected by silver stain in a fraction collected from the column represented in FIG. 4.

FIG. 6 represents the results of glycosidase digestion of O-fucosyltransferase. Reduced samples were electrophoresed on a 12% gel with SDS. Lane 1 is from the control reaction without glycosidases. Lane 2 is PNGase F digestion and Lane 3 is Endoglycosidase H digestion. The low molecular weight bands in Lane 2 and 3 are PNGase F and endoglycosidase H, respectively. The two outer lanes are molecular weight markers.

FIG. 7 represents a chromatograph of Factor IX EGF domain and its mutants by reverse phase HPLC. The recombinant mutants are as described in Table 2. Peaks labeled with retention times are recombinant proteins as verified by electrospray mass spectrometry. In one chromatogram all labeled peaks have the same molecular weight.

FIG. 8 represents an LC/MS of the reaction product of O-fucosyltransferase upon the mutant EGF.AA. The reverse phase HPLC chromatogram of the non-fucosylated form is shown in FIG. 7, panel A. The upper panel of FIG. 8 is the chromatogram of RP-HPLC of O-fucosylated EGF.AA. Major peaks were labeled with retention time and their corresponding mass spectra are shown in the lower panel. Major ions are labeled with their mass over charge value.

The calculated molecular weights are 5817 (peaks 28.8, 29.3 & 33.0) and 5964 (peak 30.4 only).

FIG. 9 is a comparison of the amino acid sequences between a partial sequence of the isolated CHO O-fucosyltransferase and known human and *C. elegans* sequences. The N terminal polypeptide sequence of CHO O-fucosyltransferase is shaded. Human sequence if a partial cDNA of unknown protein from a myeloblast cell. These sequences were generated from a partial cDNA of an unknown protein from a myeloblast cell line and a genomic *C. elegans* sequence, respectively.

FIG. 10 is a northern blot for O-fucosyltransferase. The probes were taken from human KIAA sequences as indicated in FIG. 11. The molecular weight markers are given in kilobases.

FIG. 11 is the DNA sequence of human KIAA0180 first EcoR1 fragment. The first EcoR1 fragment of the cDNA contains a partial coding sequence within a complete amino terminus. The region which matched with the CHO polypeptide sequence is shaded. The two oligonucleotides used to make the probes for the northern blot (FIG. 10) are over-scored and double-underlined. The nucleotides over-scored and single under-lined were used in the PCR amplification.

FIG. 12 is the DNA sequence of human heart O-fucosyltransferase. The upper panel (A) is a compiled sequence from positive cDNA clones. The region that matches with the isolated CHO sequence is shaded. The residue "A" at position 540 of the DNA sequence (indicated by double underline) is different from that of human KIAA0180 (G at position 475 of FIG. 11), however, the coded polypeptides are the same. The lower panel (B) is a comparison of O-fucosyltransferase amino terminal sequences isolated from human heart and CHO cells.

FIG. 13 represents the plasmid construct for expression of human O-fucosyltransferase. The upper panel (A) is a schematic drawing of the plasmid. The lower panel (B) is the sequence of the insert. The artificial signal polypeptide is shaded and the polyhistidine tag is double underlined. The human heart O-fucosyltransferase part is the same as described in FIG. 12.

FIG. 14 is a graphical comparison of the O-fucosyltransferase activity in 5 tested recombinant clones. The cultures were infected with five (5) purified recombinant clones and tested for enzyme activity according to the method of the invention. The cultures of uninfected cells (Sf9) were used as the control.

FIG. 15 is a 12% SDS-PAGE silver stained gel of recombinant human O-fucosyltransferase. Lane 1 contains infected culture medium. Lane 2 contains flow through fraction of $Ni^{2+}$—NTA column. Lane 3 is the result of 25 mM imidazole wash, while Lane 4 is 0.3 M imidazole elution. The molecular weight markers are in kilodalton.

SEQ ID NO:1 is the sequenced nucleotide sequence of human heart O-fucosyltransferase which was isolated in Example 1 and indicated in FIG. 12A.

SEQ ID NO:2 is the amino acid sequence of human heart O-fucosyltransferase isolated from Sf9 cells shown in FIG. 12A.

SEQ ID NO:3 is N-terminal amino acid sequence of CHO O-fucosyltransferase shown in FIG. 12B.

SEQ ID NO:4 is the nucleotide sequence starting from bp. 4101 to 5399 and represents the nucleotide sequence depicted in FIG. 13B. This sequence also comprises the DNA insert used in the cloning and expression of human heart O-fucosyltransferase.

SEQ ID NO:5 is the full length nucleotide sequence of the expression plasmid including SEQ ID NO:4.

SEQ ID NO:6 is the amino acid sequence representing the plasmid insertion shown in FIG. 13B.

SEQ ID NO:7 is the first EcoR1 nucleotide sequence of human KIAA0180 depicted in FIG. 11.

SEQ ID NO:8 is a computer generated amino acid sequence corresponding to genomic DNA from C. Elegans depicted in FIG. 9.

SEQ ID NO:9 is the first 61 N-terminal amino acid residues of human heart O-fucosyltransferase depicted in FIG. 12B.

SEQ ID NO:10 is the nucleotide sequence of the first probe used in the northern blot hybridization of Example 1.

SEQ ID NO:11 is the nucleotide sequence of the second probe used in the northern blot hybridization of Example 1.

SEQ ID NO:12 is the first PCR primer used in the amplification described in Example 1.

SEQ ID NO:13 is the second PCR primer used in the amplification described in Example 1.

SEQ ID NO:14 is the N-terminal amino acid sequence of the polypeptide expressed in Sf9 cells shown described in Example 1.

SEQ ID NO:15 is the expressed EGF factor domain derived primary sequence used in making the acceptor analog ligand described in Example 2.

SEQ ID NO:16 is the first 1100 nucleotides which correspond to the actively expressed human heart O-fucosyltransferase shown in FIG. 12A.

SEQ ID NO:17 is the published partial human sequence of unknown function from a myeloblast cell line.

DETAILED DESCRIPTION OF THE PREFERRED EMBODIMENTS

Definitions:

The terms used throughout this application are to be construed with the meaning typical to those of ordinary skill in the art. However, Applicants desire that the following terms be given the particular definition as described below.

The word "protein" or "polypeptide" are intended to be used interchangeably. They refer to chains of two (2) or more amino acids which are linked together with peptide or amide bonds, regardless of post-translational modification (e.g., glycosylation or phosphorylation). The term "enzyme" should also be construed interchangeably with O-fucosyltransferase.

The phrase "substantially pure" is meant to describe O-fucosyltransferase which has been separated from components which naturally accompanied the enzyme during its production. Such production could be either from natural sources (cell lines, tissues), recombinant sources, or even synthetic such as by stepwise chemical amino acid addition. Typically, the polypeptide is substantially pure when it is at least 60%, by weight, free from the proteins and other organic molecules with which it has been associated during synthesis. Preferably, the preparation is at least 75%, more preferably at least 90% and most preferably at least 99%, by weight, of O-fucosyltransferase. A substantially pure O-fucosyltransferase may be obtained by extraction from a natural source (e.g. CHO cell, human heart, liver, muscle, pancreas tissue or tissue derived cell line), by expression of a recombinant nucleic acid encoding an O-fucosyltransferase polypeptide, or chemically by synthesizing the protein. Purity can be measured by any appropriate method, e.g., column chromatography, polyacrylamide gel electrophoresis, or HPLC analysis.

The phrase "substantially identical" with respect to a polypeptide sequence shall be construed as a polypeptide exhibiting at least 70%, preferably 80%, more preferably 90%, and most preferably 95% sequence identity to the reference polypeptide sequence. The term with respect to a nucleic acid sequence shall be construed as a sequence of nucleotides exhibiting at least 85%, preferably 90%, more preferably 95%, and most preferably 97% sequence identity to the reference nucleic acid sequence. For polypeptides, the length of the comparison sequences will generally be at least 25 amino acids. For nucleic acids, the length will generally be at least 75 nucleotides.

The term "identity" or "homology" is construed to mean the percentage of amino acid residues in the candidate sequence that are identical with the residue of a corresponding sequence to which it is compared, after aligning the sequences and introducing gaps, if necessary to achieve the maximum percent homology for the entire sequence, and not considering any conservative substitutions as part of the sequence identity. Neither N- or C-terminal extensions nor insertions shall be construed as reducing identity or homology. Methods and computer programs for the alignment are well known in the art.

Sequence identity may be measured using sequence analysis software (e.g. Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

The phrase "EGF domain" or "Epidermal Growth Factor domain" shall mean a section, repeating region, motif or structural unit of a secreted polypeptide which is characterized by the presence of six (6) conserved cysteine residues that are expected to form at least three (3) intrachain disulfide bonds in a 1-3, 2-4, and 5-6 pattern.

The phrase "functional fragment or analog" of a native polypeptide is a compound having qualitative biological activity in common with a native polypeptide. Thus, a functional fragment or analog of an O-fucosyltransferase is a compound that has a qualitative biological activity in common with O-fucosyltransferase, i.e. can transfer an activated fucose moiety to an amino acid or growing carbohydrate chain. "Functional fragments" include, but are not limited to, peptide fragments of the native polypeptide from any animal species (including humans), and derivatives of native (human and non-human) polypeptides and their fragments, provided that they are able to effect a similar function as the full-length polypeptide. The term "analog" means an amino acid sequence and its glycosylation variants which are share functionality similar to the full-length active O-fucosyltransferase molecule.

The terms "amino acid" and "amino acids" refer to all naturally occurring L-α-amino acids. The amino acids are identified by either a single-letter or three-letter designations:

| Asp | D | aspartic acid | Ile | I | isoleucine |
|---|---|---|---|---|---|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |
| Xaa | X | unknown residue | | | |

The above amino acids can be classified according to the chemical composition and properties of their side chains. They are broadly classified into two groups, charged and uncharged. Each of these groups is divided into subgroups to classify the amino acids more accurately:

1. Charged:
   acidic residues: aspartic acid, glutamic acid basic residues: lysine, arginine, histidine
2. Uncharged:
   hydrophilic residues: serine, threonine, asparagine, glutamine
   aliphatic residues: glycine, alanine, valine, leucine
   non-polar residues: cysteine, methionine, proline
   aromatic residues: phenylalanine, tyrosine, tryptophan The term "amino acid variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxyl or α-amino functional group of the amino acid.

Deletional variants are those with one or more amino acids in the native amino acid sequence removed. Ordinarily, deletional variants will have one or two amino acids deleted in a particular region of the molecule.

The term "glycosylation variant" is used to refer to a glycoprotein having a glycosylation profile different from that of a native counterpart or to glycosylated variants of a polypeptide unglycosylated in its native form(s). Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, xylose or fucose to a hydroxyamino acid, most commonly serine or threonine, although 5-hydroxyproline or 5-hydroxylysine may also be involved in O-linked glycosylation.

The term "cell", "cell line" and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The "host cells" used in the present invention generally are prokaryotic or eukaryotic hosts. Such host cells are, for example, disclosed in U.S. Pat. No. 5,108,901, issued Apr. 28, 1992 arid in copending application Ser. No. 08/446,915 filed May 22, 1995 and its parent applications. Suitable prokaryotes include gram negative or gram positive organisms, for example *E. coli* or bacilli. A preferred cloning host is *E coli* 294 (ATCC 31,446) although other gram negative or gram positive prokaryotes such as *E. Coli* B, *E.Coli* x 1776 (ATCC 31,537), *E. coli* W3110 (ATCC 27,325). Pseudomonas species, or *Serratia Marcesans* are suitable. In addition to prokaryotes, eukaryotic microbes such as filamentous fungi and yeasts are suitable hosts for appropriate vectors of the invention. *Saccharomyces cerevisiae*, or common baker's yeast, is one of the most commonly used among lower eukaryotic host microorganisms. However, a number of other genera, species and strains are commonly available and useful herein, such as those disclosed in the above-cited patent and patent applications. A preferred yeast strain for the present invention is *Saccharomyces cerevisiae* HF7c (CLONTECH).

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plant and insect cells, *eg*, Luckow et al., *Bio/Technology* 6, 47–55 (1988); Miller et al., *Genetic Engineering*, Setlow et al., eds., vol. 8, pp. 277–279 (Plenam publishing 1986); and Mseda et al., *Nature* 315, 592–594 (1985). Interest had been greatest in vertebrate cells, and propagation of vertebrate cells in culture (tissue culture) is per se known. See *Tissue Culture*, Academic Press, Kruse and Patterson, eds. (1973). Examples of useful mammalian host cell lines are monkey kidney CV1 line transformed by SV40 (COS-7, ATCC CRL 1651); human embryonic kidney cell line (293 or 293 cells subcloned for growth in suspension cultures, Graham et al., *H. Gen. Virol.*, 36, 59 (1977); baby hamster kidney cells 9BHK, (ATCC CCL 10); Chinese hamster ovary cells/-DHFR (CHO, Urlaub and Chasin, *Proc. Natl. Acad. Sci. USA*, 77, 4216 (1980); mouse sertoli cells (TM4, Mather, *Giol. Reprod.* 23, 243–251 (1980); monkey kidney cells (CV1 ATCC CCL 70); African green monkey kidney dells (VERO-76, ATCC CRL-1587); human cervical carcinoma cells (HELA, ATCC CCL 2); canine kidney cells (MDCK, ATCC CCL 34); buffalo rat liver cells (Hep G2, HB 8065); mouse mammary tumor (MMT 060562, ATCC CCL51); TRI cells (Mather et al., *Annual N.Y. Acad. Sci*. 383, 44068 (1982); MRC 5 cells; FS4 cells; and a human hepatoma cell line (Hep G2). Preferred host cells are human embryonic kidney 293 and Chinese hamster ovary cells. Particularly preferred for the present invention is the insect cell line sf9 as well as other host suitable for baculovirus expression. Ausubel, Ch. 16.9–16.11.

"Transformation" means introducing DNA into an organism so that the DNA is replicable, either as an extrachromosomal element or by chromosomal integration.

"Operably linked" means that a gene and a regulatory sequence(s) are connected in such a way as to permit gene expression when the appropriate molecules (*eg*, transcriptional activator proteins) are bound to the regulatory sequence(s).

"Transfection" refers to the taking up of an expression vector by a host cell whether or not any coding sequences are in fact expressed.

The terms "transfected host cell" and "transformed" refer to the introduction of DNA into a cell. The cell is termed a "host cell" and it may be either prokaryotic or eukaryotic. Typical prokaryotic host cells include various strains of *E. Coli*. Typical eukaryotic host cells are mammalian, such as Chinese hamster ovary or cells of human origin. The introduced DNA sequence may be from the same species as the host cell or a different species from the host cell, or it may be a hybrid DNA sequence, containing some foreign and some homologous DNA.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector at present. However, the invention is intended to include such other forms of vectors which serve equivalent functions and which are, or become, known in the art. Preferred expression vectors for mammalian cell culture expression are based on pRK5 (EP 307,247, Rothe et al., Cell, supra), pSV16B (WO 91/08291) and pVL1392 (Pharmingen).

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothis et al., *J. Mol. Biol.* 186, 651–663 (1985); Novotny and Haber, *Proc. Natl. Acad. Sci. USA*, 82, 4592–4596 (1985).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A., Sequences of Proteins of Immunological Interest, National Institute of Health, Bethesda, Md. 1991). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragment, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in a tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

The light chains of antibodies (immunoglobulin) from any vertebrate species cam be assigned to one of two clearly distinct types, called kappa (κ) and lambda (λ), based on the amino acid sequences of their constant domains.

Depending on the amino acid sequences of the constant domain of their heavy chains, immunoglobulins can be assigned to different classes. There are five major classes of immunoglobulins: IgA, IgD, IgE, IgG and IgM, and several of these may be further divided into subclasses (iso-types), e.g IgG-I, IgG-2, IgG-3, and IgG-4; IgA-1 and IgA-2. The heavy chains constant domains that correspond to the different classes of immunoglobulins are called α, Δ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinant (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256, 495 (1975), or may be made by recombinant DNA methods (see eg, U.S. Pat. No. 4,816,567).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al, *Proc. Natl. Acad. Sci. USA*, 81, 6851–6855 (1984).

"Humanized" forms of non-human (eg. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al, *Nature* 321, 522–525 (1986); Reichmann et al., *Nature* 332, 323–329 (1988) and Presta, *Curr. Op. Struct. Biol.* 2, 593–596 (1992).

I. Identification and Purification of O-fucosyltransferase:

The native O-fucosyltransferase may, for example, be identified and purified from certain tissues which possess O-fucosyltransferase mRNA and which express it at a detectable level. Rat O-fucosyltransferase, for example, can be obtained from rat liver mRNA (see Sadler et al., *Methods Enzymol.* 83, 458–514 (1982) for procedure). Human O-fucosyltransferase, for example, can be prepared, according to the invention from heart, muscle, kidney and pancreas (See FIG. 10). Additionally, native O-fucosyltransferases can be identified and purified from tissues expressing their mRNAs based upon the presence of O-fucose in expressed proteins from that tissue source.

Cell lysate is prepared by any technique commonly employed in the art. For example, sonication in imidazole buffer aqueous NaCl, followed by centrifugation. The supernatant may then be applied to a series of affinity columns, depending upon the level of purity desired. Initially, we have found that a column of anion exchange followed by a nucleotide binding resin is effective. While any anion exchange resin commonly used in the art is suitable, DE-52 (Whatman) is preferred. Suitable nucleotide binding resins are readily apparent to those of skill in the art, however, preferred for use with the present invention are dye resins, such as Cibacron Blue 3GA. Particularly preferred is Affi-Gel Blue (BioRad). While some O-fucosyltransferase activity will be obtained after these initial purification steps, in order to obtain substantially higher activity, additional chromatography steps wherein affinity columns should be sequentially applied wherein acceptor substrate and donor substrate analogs to O-fucosyltransferase have been associated with an affinity resin. The donor substrate analog can be any which are commonly used in the purification of fucosyltransferases. For example, GDP-hexanolamine associated with Sepharose 4B or any other suitable agarose resin. Beyer et al., *J. Biol. Chem.* 255 (11), 5364–5372 (1980).

The acceptor ligand is prepared by first identifying a polypeptide domain containing an O-glycosylated fucose and then applying commonly employed cloning techniques to amplily, then purfying the expressed product. Particular techniques which can be used for recombinant expression are similar to those explained for the expression of O-fucosyltransferase, infra. A particularly useful ligand may be created from the first EGF domain of human factor VII. We have found that when a polyhistidine tag, which is typically located between the signal peptide and the expressed ligand, is instead placed at the C-terminus, the binding between the ligand and the affinity resin is enhanced.

The preferable affinity resins for use with the acceptor substrate ligand are metal chelating resins or IMAC (immobilized metal affinity chromatography) associated with agarose. The use of metal chelating resins permits attachment of the EGF ligand to the resin in a defined orientation, according to the position of polyhistidine sequence. As mentioned previously, we have found that ligand-resin binding was enhanced when the polyhistidine tag was inserted at the C-terminus, rather than the N-terminus of the cDNA insert. It is possible to elute the protein with the ligand together under very mild conditions, such as imidazole or EDTA. The coupling of the recombinant EGF to the metal affinity resin agarose is very simple and fast, and is preferably carried out by mixing the resin and ligand in Tris buffer. It is further possible to use the recombinant EGF without the initial purification on a nickel column. Examples of suitable metal affinity resins are IMAC resins such $Ni^{2+}$—NTA (<u>N</u>itro <u>T</u>riacetic <u>A</u>cid)(Qiagen), and metal ligand resins associated with iminodiacetic acid (Pharmacia).

II. Recombinant Production of O-fucosyltransferase

Preferably, the O-fucosyltransferase polypeptides of the present invention are prepared by standard recombinant methods by culturing cells transfected to express O-fucosyltransferase nucleic acid. A typical standard method is by transforming the cells with an expression vector and recovering the polypeptide from the cells.

However, it is envisioned that the O-fucosyltransferase polypeptides may be produced by homologous recombination, or by recombinant production methods utilizing control elements introduced into cells already containing DNA encoding an O-fucosyltransferase. For example, a powerful promoter/enhancer element, a suppressor, or an exogenous transcription modulatory element may be inserted in the genome of the intended host cell in proximity to an orientation sufficient to influence the transcription of DNA encoding the desired O-fucosyltransferase polypeptide. The control element does not encode the O-fucosyltransferase, rather the DNA is indigenous to the host cell genome. Next, cells can be screened for making the polypeptide of this invention, or for increased or decreased levels of expression, as desired. General techniques of recombinant DNA technology are, for example, disclosed in Sambrook et al., *Molecular Cloning: A laboratory Manual*, 2d Edition, (Cold Spring Harbor Press, Cold Spring Harbor, N.Y. (1989) and in Ausubel et al, *Current Protocols in Molecular Biology*, John Wiley and Sons, Inc., USA (1995).

Thus, the invention contemplates a method for producing an O-fucosyltransfera 3e comprising inserting into the genome of a cell containing nucleic acid encoding an O-fucosyltransferase polypeptide, a transcription modulatory element in sufficient proximity and orientation to the nucleic acid molecule to influence transcription thereof, with an optional further step of culturing the cell containing the transcription modulatory element and the nucleic acid molecule. The invention also contemplates a host cell containing the indigenous O-fucosyltransferase polypeptide nucleotide operably linked to exogenous control sequences recognized by the host cell.

A. Isolation of DNA encoding the O-fucosyltransferases

For the purposes of the present invention, DNA encoding an O-fucosyltransferase polypeptide can be obtained from cDNA libraries prepared from tissue believed to contain an O-fucose glycosylated polypeptide encoding mRNA and to express it at a detectable level. For example, a cDNA library can be constructed by obtaining polyadenylated mRNA from a cell line known to express O-fucose glycosylated polypeptides bearing an EGF domain, and using the mRNA as a template to synthesize double stranded cDNA. Human and non-human cell lines suitable for this purpose have been listed above under the description for "host cells."

Libraries, either cDNA or genomic, are screened with probes designed to identify the gene of interest or the protein encoded by it. For cDNA expression libraries, suitable probes include monoclonal and polyclonal antibodies that recognize and specifically bind to O-fucosyltransferase enzymes. For cDNA libraries, suitable probes include carefully selected oligonucleotide probes (usually of about 20–80 bases in length) that encode known or suspected portions of O-fucosyltransferase polypeptides from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al, *Molecular Cloning: A Laboratory Manual*, Cold Spring Harbor Press, N.Y. (1989); and in Chapter 6 of Ausubel et al, *Current Protocols in Molecular Biology*, John Wiley and Sons, USA (1995).

A preferred method of practicing the invention is to use carefully selected oligonucleotide sequences to screen cDNA libraries from various tissues. The oligonucleotide sequences selected should be sufficient in length and sufficiently unambiguous that false positives are minimized. The actual nucleotide sequence(s) is/are usually designed based on regions of an O-fucosyltransferase which have the least codon redundancy. The oligonucleotides may be degenerate (i.e, a mixture of possible codons for a given amino acid(s)) at one or more positions. The use of degenerate oligonucleotides is of particular importance where a library is screened from a species in which preferential codon usage is not known.

The oligonucleotide must be labeled such that it can be detected upon hydridization to DNA in the library being screened. The preferred method of labeling is to use ATP (eg. $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding O-fucosyltransferases can also be identified and isolated by other known techniques of recombinant DNA technology, such as by direct expression cloning or by using the polymerase chain reaction (PCR) as described in U.S. Pat. No. 4,683,195, issued Jul. 28, 1987, in section 14 of Sambrook et al, supra, or in Chapter 15 or Ausubel et al, supra. This method requires the use of oligonucleotide probes that will hybridize to DNA encoding O-fucosyltransferase.

Once cDNA encoding an O-fucosyltransferase from one species has been isolated, cDNAs from other species can also be obtained by cross-species hybridization. According to this approach, human or other mammalian cDNA or genomic libraries are probed by labeled oligonucleotide sequences selected from known O-fucosyltransferase sequences (such as human heart or CHO) in accord with known criteria, among which is that the sequence should be sufficient in length and sufficiently unambiguous that false positives are minimized. Typically, a $^{32}P$-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid.

Once the sequence is known, the gene encoding a particular O-fucosyltransferase polypeptide can also be obtained by chemical synthesis, following any known technique. For example, Engles and Uhlmann, *Agnew. Chem. Int*. Ed. Engl. 28, 716 (1989). These methods include triester, phosphite, phosphoramidite and H-phosphorate methods, PCR and other autoprimer methods, and oligonucleotide syntheses on solid supports.

B. Amino Acid sequence variants of a native O-fucosyltransferase protein or fragment Amino acid sequence variants of native O-fucosyltransferases and functional fragments thereof are prepared by methods known in the art by introducing appropriate nucleotide changes into a native or variant O-fucosyltransferase, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the O-fucosyltransferase, the amino acid sequence variants of O-fucosyltransferase are preferably constructed by mutating the DNA, either to arrive at an allele or an amino acid sequence variant that does not occur in nature.

Amino acid alterations can be made at sites that differ in O-fucosyltransferases from various species, or in highly conserved regions, depending on the goal to be achieved. For example, mutations which result in an enzyme with greater affinity for the EGF domain of polypeptides would be useful as inhibitors of natural O-fucosyltransferase. In addition, such variants would also be useful in the diagnosis of pathological conditions associated with the overexpression of O-fucosyltransferase. Moreover, inhibitors of O-fucosyltransferase would be expected to be useful in the treatment of conditions associated with proteins or factors having their efficacy determined at least in part by the presence of O-linked fucose.

Sites of mutations will typically be modified in series, eg. by (1) substituting first with conservative choices and then with more radical selections depending upon the results achieved, (2) deleting the target residue of residues, or (3) inserting residues of the same or different class adjacent to the located site, or combinations of options (1)–(3).

One helpful technique is called "alanine scanning" (Cunningham and Wells, *Science* 244, 1081–1085 (1985). Here, a residue or group of target residues is identified and substituted by alanine or polyalanine. Those domains demonstrating functional sensitivity to the alanine substitutions are then refined by introducing further or other substitutes at or for the sites of alanine substitution.

After identifying the desired mutation(s), the gene encoding an O-fucosyltransferase variant can for example, be obtained by chemical synthesis as hereinabove described.

More preferably, DNA encoding an O-fucosyltransferase amino acid variant sequence is prepared by site-directed mutagenesis of DNA that encodes an earlier prepared variant or a nonvariant version of O-fucosyltransferase. Site-directed (site-specific) mutagenesis allows the production of O-fucosyltransferase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al, *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al, *Third Cleveland Symposium on Macromolecules and Recombinant DNA*, A. Walton, ed., Elsevier, Amsterdam (1981). This and other phage vectors are commercially available and their use is well known to those of ordinary skill in the art. A versatile and efficient procedure for the construction of oligodeoxyribonucleotide directed site-specific mutations in DNA fragments using M13-derived vectors was published by Zoller, M J and Smith, M, *Nucleic Acids Res*. 10 6487–6500 (1982). Also, plasmid vectors that contain a single-stranded phage origin of replication, Veira et al., *Meth. Enzymol*. 153, 3 (1987) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al, *Proc. Natl. Acad. Sci. USA* 75, 5765 (1978). This primer is then annealed with the single-stranded protein sequence-containing vector, and subjected to DNA-polymerizing enzymes such as, *E. Coli* polymerase I Kienow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of an O-fucosyltransferase. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutations(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphate and is included in the GeneAmp® kits (obtained from Perkin-Elmer Cetus, Norwalk, Conn. and Emeryville, Calif.) and 25 pmole of each oligonucleotide primer, to a final volume of 50 $\mu$l. The reaction mixture is over layered with 35 $\mu$l mineral oil. The reaction is denatured for 5 minutes at 100° C., placed briefly on ice, and then 1 $\mu$l *Thermus aquaticus* (Taq) DNA polymerase (5 units/l) purchased from Perkin-Elmer Cetus, Norwalk, Conn. and Emeryville, Calif.) is added below the mineral oil layer. The reaction mixture is then inserted into a DNA Thermal Cycler (also purchased from Cetus) and programmed as follows:

2 min. 55° C.
30 sec. 72° C., then 19 cycles of the following:
30 sec. 94° C.
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material subsequently subjected to appropriate treatments for insertion into a vector.

Another method for preparing variants, cassette mutagenesis, is based on the technique described by Wells et al, *Gene* 34, 315 (1985). The starting material is the plasmid (or vector) comprising the O-fucosyltransferase DNA to be mutated. The codon(s) within the O-fucosyltransferase to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the O-fucosyltransferase DNA. After the restriction sites have been introduced into the plasmid, the plasmid is cut at these sites to linearize it. A double-stranded oligonucleotide encoding sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasm id. This plasm id now contains mutated O-fucosyltransferase DNA sequence.

Further details of the foregoing and similar mutagenesis techniques are found in general Molecular Biology textbooks, for example, Sambrook *et al, supra*, and *Current protocols in Molecular Biology*, Ausubel, et al., supra.

Substitutions of particular amino acid residues based on common side chain properties is also anticipated within the scope of this invention. Naturally-occurring amino acids are divided into groups based on common side chain properties:

(1) hydrophobic: norleucine, met, ala, val, leu, ile;
(2) neutral hydrophobic: cys, ser, thr;
(3) acidic: asp, glu;
(4) basic: asn, gin, his, lys, arg;
(5) residues that influence chain orientation: gly, pro; and
(6) aromatic: tip, tyr, phe Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant, and may result in a non-functional O-fucosyltransferases. Amino acid positions that are conserved among various species are generally substituted in a relatively conservative manner if the goal is to retain biological function.

Amino acid sequence deletions range from about 1 to 30 residues, more preferably about 1 to 10 residues, and typically are contiguous. Deletions, may be introduced into regions not directly involved in the catalytic domain.

Amino acid insertions include amino- and/or carboxyl-termninal fusions ranging in length from one residue to polypeptides containing a hundred or more residues, as well as intrasequence insertions of single or multiple amino acid residues. Intrasequence insertions (*i.e.* insertions within the O-fucosyltransferase amino acid sequence) may range generally from about 1 to about 10 residues, more preferably 1 to 5 residues, most preferably 1 to 3 residues. Examples of terminal insertions include the O-fucosyltransferase polypeptides with an N-terminal methionyl residue, an artifact of its direct expression in bacterial recombinant cell culture, and fusion of a heterologous N-terminal signal sequence to the N-terminus of the O-fucosyltransferase molecule to facilitate the secretion of the mature O-fucosyltransferase from recombinant host cells. Such signal sequences will generally be obtained from, and thus homologous to the intended host cell species. Suitable sequences include STII or lpp for *E. Coli.*, alpha factor for yeast, and viral signals such as herpes gD for mammalian cells.

Since it is often difficult to predict in advance the characteristics of a variant O-fucosyltransferase, it will be appreciated that some screening will be needed to select the optimum variant.

C. Insertion of DNA into Cloning Vehicle

Once the nucleic acid encoding a native or variant O-fucosyltransferase is available, it is generally ligated into a replicable expression vector for further cloning (amplification of the DNA.), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin or replication, one or more marker genes, an enhancer element, a promoter, and a transcription termination sequence.

(1) Signal sequence Component

In general, the signal sequence may be a component of the vector, or it may be a part of the O-fucosyltransferase molecule that is inserted into the vector. If the signal sequence is heterologous, it should be selected such that it is recognized and processed (i.e., cleaved by a signal peptidase) by the host cell.

Since O-fucosyltransferase is likely a membrane-bound protein, it is likely to have a native signal sequence. This native signal sequence can be used or another may be chosen. Heterologous signal sequences suitable for prokaryotic host cells are prokaryotic signal sequences, such as the alkaline phosphatase, penicillinase, Ipp, or heat-stable enterotoxin II leaders. For yeast secretion, the yeast invertase, alpha factor, or acid phosphatase leaders may be used. In mammalian cell expression, mammalian signal sequences are suitable.

(2) Origin of Replication Component

Both expression and cloning vectors contain a nucleic acid that enables the vector to replicate in one or more selected host cells. Generally, in cloning vectors this sequence is one that enables the vector to replicate independently of the host chromosomes, and includes origins or replication or autonomously replicating sequences. Such sequences are well known for a variety of bacteria, yeast and viruses. The origin of replication from the well-known plasmid pBR322 is suitable for most gram negative bacteria, the 2μ plasmid origin for yeast and various viral origins (SV40, polyoma, adenovirus, VSV, BPV) are useful for cloning vectors in mammalian cells. Origins of replication are not needed for mammalian expression vectors (the SV40 origin may typically by used only because it contains the early promoter). Most expression vectors are "shuttle" vectors, i.e. they are capable of replication in at least on class of organisms but can be transfected into another organism for expression. For example, a vector is cloned in *E. coli* and then the same vector is transformed into yeast or mammalian cells for expression even though it is not capable of replicating independently of the host cell chromosome.

DNA is also cloned by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the DNA encoding the desired heterogous polypeptide. However, the recovery of genomic DNA is more complex than that of an exogenously replicated vector because restriction enzyme digestion is required to excise the encoded polypeptide molecule.

(3) Selection Gene Component

Expression and cloning vectors should contain a selection gene, also termed a selectable marker. This is a gene that encodes a protein necessary for the survival or growth of host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, *eg*, ampicillin, neomycin, methotrexate or tetracycline, (b) complement autotrophic deficiencies, or (c) supply critical nutrients not available from complex media, *eg.* the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin, Southern et al., *J. Molec. Appl. Genet.* 1, 327 (1982), mycophenolic acid, Mulligan et al., *Science* 209, 1422 (1980), or hygromycin, Sudgen et al., *Mol. Cel. Biol.* 5, 410–413 (1985). The three examples given above employ bacterial genes under eukaryotic control to convey resistance to the appropriate drug G418 or neomycin (geneticin), xgpt (mycophenolic acid), or hygromycin, respectively.

Other examples of suitable selectable markers for mammalian cells are dihydrofolate reductase (DHFR) or thymidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Nat'l. Acad. Sci. USA* 77, 4216 (1980). A particularly useful DHFR is a mutant DHFR that is highly resistant to MTX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp1 gene present in the yeast plasmid YRp7 (Stinchcomb et al., 1979, *Nature* 282:39; Kingsman et al, 1979, *Gene* 7:141; or Tschemper et al., 1980, *Gene* 10: 157). The trp1 gene provides a selection marker for a mutant strain of yeast lacking the ability to grow in tryptophan, for example, ATCC No. 44076 or PEP4-1 (Jones, 1977, *Genetics* 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(4) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for a O-fucosyltransferase polypeptide is not usable. However, heterologous promoters generally will result in greater transcription and higher yields of expressed O-fucosyltransferase as compared to the native O-fucosyltransferase promoters.

Promoters suitable for use with prokaryotic hosts include the β-lactamase and lactose promoter systems (Chang et al., *Nature* 275:615 (1978); and Goeddel et al., *Nature* 281:544 (1979)), alkaline phosphatase, a tryptophan (trp) promoter system (Goeddel, *Nucleic Acids Res.* 8:4057 (1980) and EPO Appln. Publ. No. 36,776) and hybrid promoters such as the tac promoter (H. de Boer et al., *Proc. Nat'l. Acad. Sci. USA* 80:21–25 (1983)). However, other known bacterial promoters are suitable. Their nucleotide sequences have been published, thereby enabling a skilled worker operably to ligate them to DNA encoding O-fucosyltransferase (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding an O-fucosyltransferase.

Suitable promoting sequences for use with yeast hosts include the promoters for 3-phosphoglycerate kinase (Hitzeman et al. *J. Biol. Chem.* 255:2073 (1980)) or other glycolytic enzymes (Hess et al, *J. Adv. Enzyme Reg.* 7:149 (1978); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences axe suitably inserted into mammalian expression vectors.

O-fucosyltransferase transcription from vectors in mammalian host cells may be controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the O-fucosyltransferase sequence, provided such promoters are compatible with the host cell systems.

The early and late promoters of the SV40 virus are conveniently obtained as an SV40 restriction fragment which also contains the SV40 viral origin of replication [Fiers et al, *Nature* 273:113 (1978), Mulligan and Berg, *Science* 209, 1422–1427 (1980); Pavlakis et al., *Proc. Natl. Acad. Sci. USA* 78, 7398–7402 (1981)]. The immediate early promoter of the human cytomegalovirus is conveniently obtained as a HindIII E restriction fragment [Greenaway et al., *Gene* 18, 355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., *Nature* 295, 503–508 (1982) on expressing cDNA encoding human immune interferon in monkey cells; Reyes et al., *Nature* 297, 598–601 (1982) on expressing human β-interferon cDNA in mouse cells under the control of a thymidine khinase promoter from herpes simplex virus; Canaani and Berg, *Proc. Natl. Acad. Sci. USA* 79, 5166–5170 (1982) on expression of the human interferon β1 gene in cultured mouse and rabbit cells; and Gorman et al., *Proc. Natl. Acad. Sci., USA* 79, 6777–6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

(5) Enhancer Element Component

Transcription of a DNA encoding the O-fucosyltransferases of the present invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent having been found 5' [Laimins et al., *Proc. Natl. Acad. Sci. USA* 78, 993 (1981)] and 3' [Lasky et al., *Mol Cel. Biol*. 3, 1108 (1983)] to the transcription unit, within an intron [Banerji et al., *Cell* 33, 729 (1983)] as well as within the coding sequence itself [Osborne et al., *Mol. Cel. Biol*. 4, 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297, 17–18 (1982) on enhancing elements for activation of eukaryotic promoters. The enhancer may be spliced into the vector at a position 5' or 3' to the O-fucosyltransferase DNA, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the O-fucosyltransferase. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res*. 9, 309 (1981) or by the method of Maxam et al., *Methods in Enzymology* 65, 499 (1980).

Particularly useful in the practice of this invention are expression vectors that provide for the transient expression in mammalian cells of DNA encoding an O-fucosyltransferase. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of an O-fucosyltransferase.

Other methods, vectors, and host cells suitable for adaptation to the synthesis of the O-fucosyltransferase polypeptides in recombinant vertebrate cell culture are described in Getting et al., *Nature* 293, 620–625 (1981); Mantel et al, *Nature* 281, 40–46 (1979); Levinson et al.; EP 117,060 and EP 117,058. A particularly useful plasmid for mammalian cell culture expression of the O-fucosyltransferase polypeptides is pRK5 (EP 307,247). Especially preferred are baculovirus expression systems as described in Ausuble, Ch. 16.9–16.11, supra, in particular, pVL1392. (Pharmingen).

(7) Construction and analysis of vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequences by the methods of Messing et al., *Nuclei Acids Res*. 9, 309 (1981) or by the method of Maxam et al, *Methods in Enzymology* 65, 499 (1980).

(8) Transient expression vectors

Particularly useful in the practice of this invention are expression vectors that provide for the transient expression in mammalian cells of DNA encoding a O-fucosyltransferase polypeptide. In general, transient expression involves the use of an expression vector that is able to replicate efficiently in a host cell, such that the host cell accumulates many copies of the expression vector and, in turn, synthesizes high level of a desired polypeptide encoded by the expression vector. Sambrook et al., supra, pp. 16.17–16.22. Transient expression systems, comprising a suitable expression vector and a host cell, allow for the convenient positive screening of such polypeptides for desired biological or physiological properties. Thus transient expression systems are particularly useful in the invention for purposes of identifying analogs and variants of native O-fucosyltransferase polypeptides with O-fucosyltransferase enzymatic activity.

(9) Suitable exemplary vertebrate cell vectors

Other methods, vectors, and host cells suitable for adaptation to the synthesis of a O-fucosyltransferase polypeptide (including functional derivatives of native proteins) in recombinant vertebrate cell culture are described in Gething et al., *Nature* 293, 620–625(1981); Mantei et al., *Nature* 281, 40–46(1979); Levinson et al., EP 117,060; and EP 117,058. A particularly useful plasmid for mammalian cell culture expression of an O-fucosyltransferase polypeptide is pRK5 (EP 307,247), pSVI6B (PCT Publication No. WO 91/08291). Particularly preferred is insect vector pVL1392 (Pharmingen), Ausubel, Ch. 16.9–16.11, supra.

III. Selection and Transformation of Host Cells

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technology* 6, 47–55 (1988); Miller et al., in *Genetic Engineering*, Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the O-fucosyltransferase DNA. During incubation of the plant cell culture with *A. tumefaciens*, the DNA encoding a O-fucosyltransferase is transferred to the plant cell host such that it is transfected, and will, under appropriate conditions, express the O-fucosyltransferase DNA. In addition, regulatory and signal sequences compatible with plant cells are available, such as the opaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells 9BHK, )ATCC CCL 10); Chinese hamster ovary cells/-DHFR [CHO, Urlaub and Chasin, *Proc. Natl. Acad. Sci. USA* 77, 4216 (1980)]; mouse sertoli cells [TM4, Mather, *Biol. Reprod* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 3065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells. Most preferred are insect cells capable of baculovirus expression: Sf9 cells, ATCC-CRL 1711, Pharmingen (21300C, Invitrogen (B825-01), or Sf21 cells. Clontech (K1601-E) Invitrogen. See Ausubel, ch. 16.9–16.11, supra.

Particularly preferred host cells for the purpose of the present invention are vertebrate cells producing the O-fucosyltransferase polypeptides.

Host cells are transfected and preferably transformed with the above-described expression or cloning vectors and cultured in conventional nutrient media modified as is appropriate for inducing promoters or selecting transformants containing amplified genes.

IV. Culturing Host Cells

Prokaryotes cells used to produced the O-fucosyltransferase polypeptides of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Bames and Sato, *Anal. Biochem.* 102, 255 (1980), U.S. Pat. Nos. 4,767,704; 4,657, 866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the O-fucosyltransferase polypeptides of this invention may be produced by homologous recombination, or with recombinant production methods utilizing control elements introduced into cells already containing DNA encoding the particular O-fucosyltransferase.

V. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}$p. However, other techniques may also be employed, such as using biotin-modified nucleotides for introduction into a polynucleotide. The biotin then serves as a site for binding to avidin or antibodies, which may be labeled with a wide variety of labels, such as radionucleotides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/ or assay of sample fluids may be either monoclonal or polyclonal, and may be prepared in any animal. Conveniently, the antibodies may be prepared against a native O-fucosyltransferase polypeptide, or against a synthetic polypeptide based on the DNA sequence provided herein as described further hereinbelow.

VI. Covalent Modifications of O-fucosyltransferase Polypeptides

Covalent modifications of O-fucosyltransferase are included within the scope of this invention. Such modifications are traditionally introduced by reacting targeted amino acid residues of the O-fucosyltransferase with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the fucosyltransferase, or for the preparation of fucosyltransferase antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amnines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-melhylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296or U.S. Pat. Nos. 4,640,835; 4,496,689; 4,301,144; 4,670,417; 4,791,192 or 4,179,337.

Derivatization with bifunctional agents is useful for preparing intramolecular aggregates of the O-fucosyltransferase with polypeptides as well as for cross-linking the O-fucosyltransferase polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and asparaginyl residues are frequently post-translaitionally deamidated to the corresponding glutamyl and aspartyl residues. Alternatively, these residues are dearnidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel polypeptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The O-fucosyltransferase polypeptides may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The O-fucosyltransferases may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

VII. Glycosylation variants of the O-fucosyltransferase

The actual glycosylation pattern of the native O-fucosyltransferase is unknown, however, variants having glycosylation which differ from the actual native sequence are within the scope herein. For ease, changes in the glycosylation pattern of a native polypeptide are usually made at the DNA level, essentially using the techniques discussed hereinabove with respect to the amino acid sequence variants. Thus, glycosylation signals can be introduced into the DNA sequence of native O-fucosylation polypeptides.

Chemical or enzymatic coupling of glycosides to the O-fucosylation molecules of the molecules of the present invention may also be used to add carbohydrate substitutes. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published Sep. 11, 1987), and in Aplin and Wriston, *CRC Crit. Rev. Biochem.*, pp. 259–306.

VIII. Anti-O-fucosyltransferase antibody preparation (A) Polyclonal antibodies

Polyclonal antibodies to a O-fucosyltransferase molecule generally are raised in animals by multiple subcutaneous (sc) or intraperitoneal (ip) injections of the O-fucosyltransferase and an adjuvant. It may be useful to conjugate the O-fucosyltransferase or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to ¹⁄₁₀ the original amount of conjugate in Freud's complete adjuvant by subcutaneous injection at multiple sites. 7 to 14 days later the animals are bled and the serum is assayed for anti-O-fucosyltransferase antibody titer. Animals are boosted until the titer plateaus. Preferably, the animal boosted with the conjugate of the same O-fucosyltransferase but conjugated to a different protein and/or through a different cross-linking reagent. Conjugates also can be made in recombinant cell culture as protein fusions. Also, aggregating agents such as alum are used to enhance the immune response.

(B) Monoclonal antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-O-fucosyltransferase monoclonal antibodies of the invention may be made using the hybridoma method first described by Kohler & Milstein, *Nature* 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., *Monoclonal Antibody Production Techniques and Applications*, pp.51–63 (Marcel Dekker, Inc., New York, 1987)].

Culture medium in which hybridoma cells are growing is assayed for production of monoclonal antibodies directed against O-fucosyltransferase. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, *Anal. Biochem.* 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Princitples and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression viectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-O-fucosyltransferase monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an O-fucosyltransferase and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., Biochemistry 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard (which may be an O-fucosyltransferase polypeptide or an immunologically reactive portion thereof) to compete with the test sample analyte (O-fucosyltransferase) for binding with a limited amount of antibody. The amount of O-fucosyltransferse in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376, 110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

(C) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986); Riechmann et al., *Nature* 332, 323–327 (1988); Verhoeyen et al., *Science* 239, 1534–1536 (1988)], by substituting rodent CDRs or CDR sequences Ofor the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551–255 (1993); Jakobovits et al., *Nature* 362, 255–258 (1993).

(D) Bispecific antibodies

Bispecific antibodies are monoclonal, preferably human or humanized, antibodies that have binding specificities for at least two different antigens. In the present case, one of the binding specificities is for a O-fucosyltransferase, the other one is for any other antigen, and preferably for another receptor or receptor subunit. For example, bispecific antibodies specifically binding two different O-fucosylliansferases, are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuellc, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker t al., *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al., *Methods in Enzymology* 121, 210 (1986).

(5) Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

IX. Methods of Using O-Fucosyltransferase Inhibitors

As reported previously, O-linked fucose has been found on a number of interesting biological molecules. Moreover it has been determined that glycosylations containing O-linked fucose are essential for proper activity of these biological molecules. More importantly, the absence of such O-linked fucose in these molecules has inhibited or lessened the efficacy of these molecules. For example, it has been reported in S. A. Rabbani et al., *J. Biol. Chem.* (1 992) 267:14151–56, that the binding of urokinase-type plasminogen activator (uPA) to its receptor (uPAR) is mediated by the EGF-domain. Furthermore, Rabbani et al. has reported that the fucosylated EGF domain of uPA was mitogenic for an osteosarcoma cell line, SaOS-2 and that, non-fucosylated EGF domain exhibited no mitogenic activity. This is particularly interesting, since non-fucosylated uPA, in a competitive inhibition assay with fucosylated uPA reduced the mitogenicity in the model.

The following proteins are known to have EGF domains similar to those capable of being glycosylated by the present O-fucosyltransferase: coagulation factor VII, coagulation factor VII(b), fibropellin C (III), scavenger receptor Cys-rich epidermal growth factor, notch 4, C-Serate -1, Motch B protein, neurogenic locus notch 3, notch 2, major fat-globule membrane protein/MGF-E8, coagulation factor IX, coagulation factor XII, hepatocyte growth factor, agrin, alpha-2-macroglobulin receptor (low-density lipoprotein receptor-related protein 1 precursor), versican, chondroitin sulfate proteoglycan, plasminogen activator (uPA), teratocarcinoma-derived growth factor (Cripto growth factor), teratocarcinoma-derived growth factor-3 ((Cripto-3 growth factor), Motch A, milk fat globule-EGF factor VIII (MFGM), fibropellin Ia, fibropellin Ib, proteoglycan PG-M (V3), fibropellin I, C-serrate-2, transmembrane protein jagged, transmembrane protein jagged-1, versican v2, neurogenic locus notch homolog 4 (transforming protein int-3), crumbs, tie receptor tyrosine kinase, fibroblast growth factor receptor ligan, fetal antigen 1, preadipocyte factor 1, delta-like dlk protein. stromal cell derived protein-1, deltaD transmembrane protein, x-Delta-1, agrin-related protein 1, neurogenic protein Delta precursor, prepromultimerin, serrate protein, slit protein 2, slit, G-protein coupled receptors, EGF repeat transmembrane protein and neurogenic locus notch 1.

Methods for preparing O-fucosyltransferase inhibitors are similar to those as is described for the preparation of O-fucosyltransferase variants under section B of Part II: Recombinant Production of O-Fucosyltransferase.

Therapeutic formulations of the polypeptide or antibody are prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See *Remington's Pharmaceutical Sciences*, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fiunarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%–1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" are present to ensure isotonicity of liquid compositions of the present invention and include polyhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, omithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacliarides such as raffinose; polysaccharides such as dextran. Stabilizers are present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in *Remington's Pharmaceutical Sciences*, 16th edition, A. Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semipermeable matrices of solid hydrophobic polymers containing the antibody mutant, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic aciid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local therapeutic agent concentration of between about 5 and 20 ng/ml, and, preferably, between about 10 and 20) ng/ml. In an additional specific embodiment of the invention, a pharmaceutical composition effective in promoting the growth and survival of retinal neurons may provide a local therapeutic agent concentration of between about 10 ng/ml and 100 ng/ml.

In a preferred embodiment, an aqueous solution of therapeutic polypeptide, antibody or fragment thereof is administered by subcutaneous injection. Each dose may range from about 0.5 µg to about 50 µg per kilogram of body weight, or more preferably, from about 3 µg to about 30 µg per kilogram body weight.

The dosing schedule for subcutaneous administration may vary form once a week to daily depending on a number of clinical factors, including the type of disease, severity of disease, and the subject's sensitivity to the therapeutic agent.

The following examples are offered by way of illustration and not by way of limitation. The disclosures of all citations in the specification are expressly incorporated herein by reference.

EXAMPLES

Example I

Sequence Analysis

Amino terminal sequences of the purified O-fucosyltransferase from CHO cells was obtained using an automated gas-phase sequencer. The protein (2 µg) was subjected to analysis for 61 cycles. The sequence obtained was the following:

R L A G S W D L A G Y L L Y X P X M G R F G N Q A D H - F L G S L A F A K L X V R T L A V P P W I E Y Q H H K P P F T N L H [SEQ ID NO:3]

Cycles that yielded uncertain residues were marked as X. They are probably glycosylation sites or cysteine residues forming disulfide bonds with other parts of the protein. A search on GenBank with the above sequence found two homologous genes of unknown function from human and *C. elegans* (FIG. 9). The human sequence, KIAA0180, is 5009 bp partial cDNA coding for protein of unknown function from myeloblast cell line KG-1. The similarity between Applicants' CHO cell and the published human sequence is around 95% at the region they overlap (39 amino acid residues at carboxyl side of the CHO cell sequence). The polypeptide form *C. elegans* was generated by computer analysis of *C. elegans* genomic sequence, CLELC 15C7_5. The entire 61 residues of Applicants' CHO cell sequence has a 37% similarity with the *C. elegans* sequence. However, if only the C-terminal 43 amino acid residues of the CHO cell sequence is compared, the similarity increases to 76%. A realistic comparison between the CHO cell and published human sequences is not possible due to the incomplete sequence information available on the human sequence. The similarity between the human and *C. elegans* sequences is about 40%.

Northern Blot Analysis

Oligonucleotide probes were made by filling two partially complement oligonucleotides from human KIAA0180 (sequences 16-55 and 80-41). These sequences also overlapped with the CHO cell polypeptide sequence as is indicated in FIG. 11. The two northern probes corresponded to the following sequences:

5'-CTTCT TGGGCTCTCT GGCATTTGCA AAGCT-GCTAA ACCGT-3' [SEQ ID) NO:10]

[SEQ ID NO:11] 3'-TTCGACGATT TGGCATGGAA CCGACAGGGA GGAAC(,TAAC-5'

The human multi-tissue RNA blot was purchased from Clontech and the experiment was carried out according to the vendor's instructions. The blot resulted in two bands of about 5 and 5.5 kb, respectively, which were present in heart, placenta, liver, muscle and pancreas, but not lung, kidney and brain (See FIG. 10). The sequences of the probes were taken from human KIAA0180 position 16-80, the region which matched with the CHO cell O-fucosyltransferase N-terminal polypeptide sequence of FIG. 11.

Isolation of cDNA Clones

The primers for the polymerase chain reaction (PCR) were taken from KIAA0180 and corresponded to kiaa 16–55 and kiaa 1110–1071. The primers corresponded to the following sequences:

5'-CTTCTTGGGCTCTCTGGCATTTGCA AAGCT-GCTAA ACCGT-3' [SEQ ID NO:12]

3'-TCCCTGGGGA GTTCCTCCCT CTGCGAGGTA-5' [SEQ ID NO:13]

The predicted product was about 1.1 kb (See FIG. 11). Probes were then made by the random priming method using the PCR product as the template.

Human heart cDNA library was purchased from Clontech. The screening was carried out according to the product manual. After the screening of one million recombinant clones, 31 positive clones were identified, of which 20 were subjected to two more screenings for confirmation. Recombinant lambda DNA from the isolated clones was digested with EcoR1 and subjected to southern blotting (Ausubel et al, Ch. 2, supra), using the same probe as for the northern blot described above, which resulted in 8 clones possibly containing the coding sequence for O-fucosyltransferase.

Subcloning and DNA Sequencing:

The positive EcoR1 fragments, as identified by the southern blot, were purified using a Qiagen extraction kit from agarose gel and subcloned into pBluescriptII SK+plasmid (Stratagene). The plasmid DNA was prepared using the Qiagen Maxiprep kit and used for DNA sequencing. DNA sequencing was carried out on a ABI 370 automated DNA sequencer, which identified that seven of the eight clones contained the KIAA0180 sequence. A compiled sequence was obtained from the data which contained both the KIAA0180 first EcoR1 fragment and the N-terminal polypeptide sequence of O-fucosyltransferase from the CHO cells (FIG. 12A). Although the translated polypeptide starts with a Met residue, the exact N-terminal residues are yet to be determined. The clones that extended beyond the 5' methionine residue all had different sequences, possibly due to a cloning artifact introduced by the GC rich region. The polypeptide from the obtained sequence as indicated in FIG. 12B most likely represents the sequence of active human O-fucosyltransferase, since the N-terminal sequence of active CHO enzyme started at the same position, although with arginine instead of methionine. The alignment of human and CHO cell sequences is also shown in FIG. 12B.

Expression

Baculovirus expression system was used to express the protein in Sf9 insect cells. A modified form of plasmid pVL1392 was used as the vector, as indicated by FIG. 13. This plasmid was particularly designed for expression in baculovirus-insect expression systems. It consisted of an artificial signal peptide designed for secretion, a six-histidine tag for purification and the putative human O-fucosyltransferase described above. Transfection was carried out with a BaculoGold expression kit (Pharmingen). Five (5) recombinant virus clones were plaque-purified three times. Virus stocks of $10^8$ pfu/ml were prepared by repeated amplification. Expression was done transfecting $5 \times 10^8$ pfu recombinant viruses to $2 \times 10^7$ Sf9 cells. The O-fucosyltransferase activity assay of the Sf9 culture media after the virus infection showed that four (4) of the five clones expressed secretory O-fucosyltransferase and cultures infected with the fifth virus and uninfected Sf9 cells had no enzyme activity (FIG. 14).

Both culture media and cells were collected 72 hours after infection and recombinant O-fucosyltransferase was purified using $Ni^{2+}$—NTA agarose according to the manufacturer's directions. The protein purified from the cell lysate gave a single band of 43 kd on silver stained SDS-PAGE (FIG. 15), which agreed with the predicted size of the molecule. The amino terminal sequence, as determined by N-terminal sequence analysis was obtained using gas-phase sequencing and confirmed that the expressed protein was recombinant and not an Sf9 cell endogenous enzyme. The N-terminal sequence was determined to be the following:

RSHHHHHHMPAGSWDPAGYLLYXPXMGR [SEQ ID NO:14]

Example 2

Fucosyltransferase Assay

A reaction volume of 50 μl contained the following ingredient: 0.1 M imidazole-HCl, pH 7.0; 50 mM $MnCl_2$; 0.1 mM GDP-$^{14}$C-Fucose (4000–8000 cpm/nmol), 20 μM recombinant human Factor VII EGF-1 domain and about 0.01–0.1 milliunit of enzyme activity. The mixture was incubated at 37° C. for 10–20 minutes. The reaction was stopped by placing the mixture on ice, then diluting with 950 μl of 0.25 M EDTA, pH 8.0. Separation of incorporated fucose from GDP-fucose, ftucose-phosphate and free fucose was carried out by passing the solution through a C18 cartridge (Alltech, Extract Clean, C18, 200 mg). The cartridge was washed with 5 ml of $H_2O$, and the product was then eluted with 3 ml of 80% acetonitrile containing 0.052% TFA. The eluant was mixed with 10 ml Aquasol II (NEN/Du Pont) and counted using a liquid scintillation counter.

Recombinant Human Factor VII and IXEGF Domains and Mutants

The construction of human Factor IX EGF domain and its mutant genes were the same as for Factor VII EGF domain. A recombinant form of the first EGF domain from human factor VII was produced in E coli. The sequences of the EGF domains was taken from residue 45–87 of the mature protein, with six histidine residues attached at the C-terminus, followed by three residues from the cloning vector. The construct included the following primary sequence:

TVDGDQCESNPCLNGG SCKDDINSYECWCPFGFEGKNCELDVTHHHH-HHGSA [Seq. ID. No. 15]

The mutants were constructed using the same oligonucleotide cassette with mutated sequences according to the method of cassette mutagenesis, Wells et al., Gene 34, 315 (1985). The expression was carried out on a 1 liter scale. The recombinant EFG domains were purified from periplasmic shokates using $Ni^{2+}$—NTA agarose (Qiagen) according to the manufacturer's instruction for non-denaturing purification. For 1 liter of culture fluid, 0.5 ml of resin was used and the eluant was then concentrated in Centricon-3 to about 200 μl and used in subsequent steps.

Example 3

Purification of O-fucosyltransferase from CHO Cell Extract

Purification of O-fucosyltransferase: Most of the enzyme activity is recoverable in the soluble fraction of the cell lysate. While the activity should not bind to a DE-52 anion exchange column, it should be found to be quantitatively retained on Affi-Gel blue resin. We have discovered further that this enzyme bears a high affinity towards both its acceptor substrate, the recombinant EGF domain, and a donor substrate analog, GDP-hexanolamine. As a result, affinity resins with these two molecules as ligands were made, which is a key purification step. The enzyme was purified 5000-fold from the cell paste with 20% yield, as measured by activity. This information in reported in Table 1.

Step 1: Preparation of CHO Cell Extract:

Since O-fucosyltransferase exhibits properties similar to those of other membrane-bound proteins, it is likely to have also a stem region very susceptible to proteolysis. In order to avoid the processing of membrane particles, protease inhibitors should be omitted during the initial homogenate preparation. The frozen CHO cell paste was thawed at room temperature and kept cold at 4° C. afterward during the entire procedure. Low ionic strength buffer was used during homogenization to help break the cells, and the addition of DNase I to the homogenate reduced the viscosity and facilitated the subsequent chromatography steps. As indicated in Table 1, most of the activity was recovered after the first step, which achieved a 2.2-fold purification.

Frozen CHO cell paste (100 grams) was thawed at room temperature and kept i-old on ice. The cells were homogenized by sonication in 300 ml buffer of 20 mM imidazole-HCl, pH 7.0 and 25 mM NaCl with three 30 second bursts (Virsonic 550, at 20% output with ½ inch probe). DNaseI (2 mg/ml, 1 ml) and 1 M $MgCl_2$ (0.4 ml) were added to the homogenate, which was then centrifuged at 10,000×g (Sorvell RC-5, GSA rotor) for 45 minutes. The supernatant (355 ml) was retained for further purification.

Step 2: DE-52 and Affi-Gel Blue Chromatography:

Since the enzyme flowed through the DE-52 column and bound to the Affi-Gel Blue, the two column were connected for loading and initial washing steps. At point A as indicated in FIG. 2, the DE-52 column was detached from the Affi-Gel Blue column. Some loosely bound protein was washed offl upon increase of salt concentration (125 mM NaCl). At point B, as indicated in FIG. 2, the enzyme was then eluted with 1 M NaCl: The application of a NaCl gradient here did not improve the purification. In FIG. 2, the amount of protein not associated with the enzyme activity was relatively low because a significant portion of that bound to the DE-52 column and was not shown in the chromatogram. The combined purification for the two columns was 7.3 fold with 70% yield. The total volume of the preparation was reduced from 350 to 40 ml.

Two columns, one DE-52 (2.5×3.0 cm) and the other Affi-Gel Blue (2.5×15 cm) were connected and equilibrated with the same buffer used for homogenization. The supernatant from the CHO cell extract step was loaded onto the DE-52 column (1 ml/min.) and the columns were washed with the same buffer. The De-52 column was then detached from the Affi-Gel Blue column. The latter was washed with 200 ml buffer of 25 mM imidazole-HCl, pH 7.0 and 125 mM NaCl and followed by 400 ml high salt (25 mM imidazole-HCl, pH 7.0, 1 M NaCl) elution. The eluted fraction containing enzyme activity were pooled and dialyzed against the buffer of 25 mM This-HCl, pH 8.0, 25 mM NaCl and 25% (w/v) glycerol. The final volume was 40 ml.

Step 3: FVII-EGF-H6-$Ni^{2+}$—NTA-Agarose (Acceptor Substrate)

The preferable acceptor analog resin for use with the present invention is Factor VII-EGF-$his_6$ and $Ni^{2+}$—NTA agarose. The use of $Ni^{2+}$—NTA agarose has several advantages over conventional covalent cross-linking resins. First, the EGF ligand is attached to the resin in a defined orientation, according to the position of polyhistidine sequence. The EGF ligand may be prepared as described in Example 2. The O-fucosyltransferase enzyme bound to the resin better when the polyhistidine tag was at the carboxyl-terminus of the EGF domain rather than at its amino-terminus, hence the former was used for the purification. Second, the binding of the polyhistidine tag to $Ni^{2+}$—NTA resin was stable under most conditions used for protein purification. The coupling of EGF to $Ni^{2+}$—NTA-Agarose was almost quantitative and the resin was very stable. It is possible to elute the protein with the ligand together under very mild conditions, such as imidazole or EDTA. The coupling of the recombinant EGF to $Ni^{2+}$—NTA agarose is very simple and fast, and is preferably carried out by mixing the resin and ligand in Tris buffer. It is further possible to use the recombinant E,GF without the initial purification on a nickel column.

We have observed no leakage of recombinant EGF domain even after extensive washing. As shown in FIG. 3, the binding of the enzyme to the resin was quantitative. At point A in FIG. 3, the column was washed with buffer containing 0.5 M NaCl, and a large amount of non-specifically bound protein was eluted. The binding of enzyme to the EGF domain was sufficiently strong so as to withstand a washing with 2M NaCl.

Since denaturation of the enzyme was possible, and linkage to the $Ni^{2+}$—NTA resin was non-covalent, the enzyme was recovered by first dissociating the EGF domain from the resin. At Point B, as indicated in FIG. 3, the column was washed with buffer containing 25 mM imidazole, and more non-specifically bound protein came off. At point C, as indicated in FIG. 3, 0.3 M imidazole solution was used to elute the polyhistidine tagged EGF domain together with the enzyme. The step purification was actually significantly higher than the 16-fold indicated in Table I because there was almost 6 mg of recombinant Factor VII EGF domain present in the eluate.

The affinity resin with acceptor substrate as ligand was made by mixing 6 mg of FVII-EGF-$H_6$ with 10 ml $Ni^{2+}$—NTA-Agarose resin in 0.1 M This-HCl, pH 8.0 for 4 hours at 4° C. The resin was then packed into column (1.5×6.0 cm) and washed with 40 ml 0.1 M This-HCl, pH 8.0, followed by another wash of 30 ml 0.1 M This-HCl, 0.5 M NaCl. It was then equilibrated with the same buffer used for dialysis in the DE-52 and Affi-Gel Blue chromatography step.

The dialyzed sample was supplemented with 1 mM $MnCl_2$ and 0.1 mM GDP and loaded onto the affinity column at a flow rate of 0.5 ml/min. followed by 40 ml of the same buffer (with 1 mM $MnCl_2$ and 0.2 mM GDP). The column was then washed with 45 ml of the same buffer containing 0.5 M NaCl and 45 ml of 25 mM imidazole-HCl, pH 7.0, 25 mM NaCl and 25% (w/v) glycerol, respectively. The enzyme was then eluted off the column with 90 ml of 0.3 M imidazole-HCl, pH 7.0, 25% (w/v) glycerol. The fractions containing activity were pooled and dialyzed against 25 mM imidazole-HCl, pH 7.0, 25 mM NaCl, 25% (w/v) glycerol.

Step 4: GDP-Hexanolamine Agarose (Donor Substrate)

GDP-hexanolamine-agarose has been used extensively in purification of many fucosyltransferases. Beyer et al., *J. Biol. Chem.* 255 (11), 5364–5372 (1980). O-fucosyltransferase also binds to this resin. However, as indicated in FIG. 4, at least half of the total amount of the enzyme flowed through the column when the sample was loaded onto column containing GDP-hexanolamineagarose. At point A, as indicated in FIG. 4, the column was washed with buffer containing 125 mM NaCl, resulting in the elution of some non-specifically bound protein. After this point, a GDP gradient (0–2 mM) was used for specific elution of the enzyme. The fractions collected from this gradient contained a very limited amount of protein, as indicated by FIG. 5. In FIG. 5, a SDS-PAGE gel overstained with silver staining only a single band of 44 KD was visible. The variation of the band intensity also reflects the enzyme activity amongst the different fractions.

The affinity resin with donor substrate analog as ligand was made by coupling GDP-Hexanolamine (30 μmol) to CNBr activated Separose 4B resin (10 ml, Pharmacia) according to the manufacturer's instructions). The resin was then packed in a column and equilibrated with the same buffer used for preparation of the acceptor substrate column.

The dialyzed sample (13 ml) was supplemented with 5 mM $MnCl_2$ and loaded onto the column at 5 ml/hr. The column was then washed with 30 ml of 25 mM imidazole-HCl, pH 7.0, 25 mM NaCl, 5 mM $MnCl_2$ and 25% (w/v) glycerol, followed by 45 ml of the same buffer with 125 mM NaCl and then another 10 ml of the buffer containing 24 mM NaCl. The elution was carried out by using a linear gradient from 0–2 mM GDP, which started with 100% of 25 mM imidazole-HCl, pH 7.0, 25 mM NaCl, 5 mM $MnCl_2$, 25% (w/v) glycerol and finished with 100% of the same buffer with 2 mM GDP in a total volume of 50 ml. The column was washed with another 40 ml of the latter buffer. Fractions containing activity were first examined by silver stained SDS-PAGE and those with only a single band were pooled. Glycerol was then added to a final concentration of 50% (w/v) for storage at –20° C.

The results of the purification are reported in Table 1 which indicates the results of one preparation of enzyme from 100 grams of CHO cell paste. Chromatograms of steps 2–4 are reported in FIGS. 2–4, respectively.

2. Endo H digestion

The protein was denatured as described above. The digestion was carried out with 1 mU of the glycosidase in 30 μl of 50 mM sodium citrate, pH 5.5, 2 mM PMSF, 0.25% NP-40 at 37° C. for 4.5 hours. An aliquo (10 μl) of the sample was analyzed on SDS-PAGE to determine the progress of the digestion.

Reverse Phase HPLC and Elctrospray Mass Spectrometry

LC-MS analyses were performed on a PE/Sciex AP-300 triple quadruple mass spectrometer interacted with a Hewlett-Packard 1090 liquid chromatograph system. Separations were carried out on a C-18 column (2.1×250 mm, Vydac), running a water/acetonitrile/TFA gradient at 0.2 ml/min. Buffer A contained 0.06% TFA and water, Buffer B was 0.052% TFA and 80% acetonitrile. The gradient had the following steps: 0–1 min., 2–10% B; 1–5 min., 10–25% B; 5–25 min., 25%–35% B; 25–30 min., 35–98% B. The column effluent was monitored at 214 nm for protein and subsequently introduced into the mass spectrometer through a 1:5 splicer in front of a regular ion sprayer. The orifice potential was set at 50 V and the ion-spray potential was at 4700 V. Mass scan was performed from 400–2500 m/z with step size of 0.5 amu and dwell time 0.1 ms. The data were analyzed using a BioMultiView 1.2.

Characterizations

1. Glycosidase digestion:

Many glycosyltransferases are glycoproteins themselves and contain various types and amounts of oligosaccharides. Moreover, the majority of these glycosyltransferases reside in the eridoplasmic reticulum or Golgi apparatus. The nature of glycosylation of the purified O-fucosyltransferase was examined using two endogylcosidases, PNGase F and Endo H. FIG. 6 indicates that after PNGase digestion, the molecular weight of the protein reduced about 4 kd to 40 kd (Lane 2), suggesting the presence of an N-linked oligosaccharide. The results also indicate that more than one high mannose type oligosaccharide was present on the enzyme.

TABLE 1

Summary of the O-fucosyltransferase purification

| Preparation | Total protein (mg) | Total volume (ml) | Total activity (units) | Specific activity (units/mg) | Step purification (fold) | Total purification (fold) | Step yield (%) | yield (%) |
|---|---|---|---|---|---|---|---|---|
| Homogenate | 5735.8 | 400 | 0.911 | 0.00016 | — | — | — | — |
| 1. Supernatant | 2238.6 | 350 | 0.785 | 0.00035 | 2.2 | 2.2 | 86.2 | 86.2 |
| 2. DE-52/Affi-Gel Blue | 215.4 | 40 | 0.550 | 0.0026 | 7.3 | 16.1 | 71.1 | 60.4 |
| 3. FVIIEGF-Ni2+-NTA-Agarose | 9.81 | 13 | 0.401 | 0.041 | 16.0 | 256 | 72.9 | 44.1 |
| 4. GDP-Hexanolamine-Agarose | 0.237 | 21 | 0.186 | 0.784 | 19.2 | 4937 | 46.4 | 20.4 |

Example 3

Glycosidase Digestion of the Purified O-fucosyltransferase

1. PNGase F digestion

Pure protein in storage buffer (50 μl) was first precipitated with 250 μl acetone at –20° C. and was then spun in a microcentrifuge for 15 minutes. The pellet was washed with 200 μl acetone and air dried. The protein was then redissolved in 10 μl of 0.5% SDS, 10 mM β-mercaptoethanol and 0.15 M This-HCl, pH 8.0 and heated at 100° C. for 3 minutes. The digestion as carried out by adding 0.5 units of PNGase F in 20 μl of 2% NP-40, 30 mM EDTA, pH 8.0 and the solution was incubated at 37° C. overnight. The digested sample (10 μl) was directly analyzed on SDS-PAGE.

2. Acceptor substrate specificity:

As described previously, all the O-fucosylation on EGF domains occur within the putative consensus sequence CXXGGS/TC. In order to prove whether or not the two glycine residues are required for O-fucosylation, human factor IX EGF domain mutants were constructed as shown in Table 11. Three mutants were constructed using alanine to replace either of the two or both glycine residues and tested as acceptor substrate for the purified O-fucosyltransferase. Assays using the four recombinant EGF domains all gave positive counts. It appeared that the two glycine residues were not absolutely required for activity.

TABLE II

Human Factor IX EGF domain mutants

| Sequence name | Sequence | Mol. Wt. | Fucose (cpm) |
|---|---|---|---|
| EGF.AA | -CLNAASC- | 5816.3 | 1818 |
| EGF.AG | -CLNAGSC- | 5802.3 | 4585 |
| EGF.GA | -CLNGASC- | 5802.3 | 6480 |
| EGF (wild type) | -CLNGGSC- | 5788.2 | 12062 |

Analysis of the recombinant factor IX EGF domains using reverse phase HPLC revealed that upon the change of glycine to alanine, the mutant EGF domains exhibited multiple peaks on the chromatograms whereas the wildtype had only one peak (FIG. 7). Further characterizations of the different peaks by electrospray mass spectrometry indicated that all the peaks from one mutant had the same molecular weight, suggesting that the multiple peaks represented differently folded species of mutant EGF domains. The analysis also leads to the conclusion that the change of either glycine residue had a significant effect upon the folding of the EGF domain.

In order to determine if all the different forms of the mutants served as substrate for the O-fucosyltransferase, reverse-phase HPLC online with electrospray mass spectrometry was used to analyze the product of the fucosylation reaction. Shown in FIG. 8 is the experiment using the mutant ala-ala. Analysis of the other tested mutants gave similar results. After the fucosylation reaction, the molecular weight of three of the four peaks (30.4) had a different molecular weight (5964), which was 146 more than the other peaks (5817) and the corresponding peak before the fucosylation reaction. These results indicate that only one of the four differently folded species served as an acceptor substrate for the O-fucosyltransferase. Although the two glycine residues were not absolutely required for activity, their presence was important for proper folding of the EGF domain, hence the wild type EGF domain was a better substrate than the mutants. The enzyme O-fucosyltransferase required its substrate in order to have the proper three dimensional structure in order to function properly.

What is claimed is:

1. An isolated and purified O-fucosyltransferase enzyme, purified such that only a single band is visible upon silver staining of an SDS-PAGE gel, which is capable of glycosylating an EGF domain of a polypeptide with an activated fucose moiety, wherein said enzyme is selected from the group consisting of a polypeptide comprising SEQ ID NO:9, a polypeptide comprising SEQ ID NO:3, a polypeptide comprising SEQ ID NO:2, a polypeptide comprising SEQ ID NO:9 with conservative substitutions, a polypeptide comprising SEQ ID NO:3 with conservative substitutions and a polypeptide comprising SEQ ID NO:2 with conservative substitutions.

2. The enzyme of claim 1 wherein the polypeptide glycosylated comprises the sequence -Cys-Xaa-Xaa-Xaa-Xaa-Ser/Thr-Cys-.

3. The enzyme of claim 2 wherein the polypeptide glycosylated comprises the sequence -Cys-Xaa-Xaa-Gly-Gly-Ser/Thr-Cys-.

4. The enzyme of claim 1 which comprises the following sequence:

MPAGSWDPAGYLLYCPCMGRFGNQADH-FLGSLAFAKLLNRTLAVPPWIEYQHH KPPFTNLH SEQ ID NO:9.

5. The enzyme of claim 1 which comprises the following sequence:

RLAGSWDLAGYLLYXPXMGRFGNQADH-FLGSLAFAKLXVRTLAVPPWIEYQHH KPPFT-NLH SEQ ID NO:3.

6. The enzyme of claim 1 comprising SEQ ID NO:2.

* * * * *

UNITED STATES PATENT AND TRADEMARK OFFICE
CERTIFICATE OF CORRECTION

PATENT NO.    : 6,100,076
DATED         : August 8, 2000
INVENTOR(S)   : Yang Wang et al.

It is certified that error appears in the above-identified patent and that said Letters Patent is hereby corrected as shown below:

Column 3,
Line 19, please replace "O-fucosyltansferase" with -- O-fucosyltransferase --.

Column 8,
Line 59, after "1992" and before "copending", please replace "arid in" with
-- and in --.

Column 14,
Line 23, please replace "O-fucosyltransfera 3e" with -- O-fucosyltransferase --.

Column 17,
Line 10, after "*E. Coli* polymerase I" and before "fragment", please replace
"Kienow" with -- Klenow --.

Column 18,
Line 65, please replace "termninal" with -- terminal --.

Column 22,
Line 37, after "sequences" and before "suitably", please replace "axe" with
-- are --.

Column 26,
Line 42, before "and Sato, *Anal.*", please replace "Bames" with -- Barnes --.

Column 27,
Line 11, at the end of the line, please replace "$^{32}$p" with -- $^{32}$P --.

Column 29,
Line 22, before "deamidated", please replace "post-translaitionally" with
-- post-translationally --.
Line 24, after "residues are", please replace "dearnidated" with -- deamidated --.

Column 33,
Line 15, after "CDR" sequences", please replace "Ofor" with -- for --.

UNITED STATES PATENT AND TRADEMARK OFFICE
CERTIFICATE OF CORRECTION

PATENT NO. : 6,100,076
DATED : August 8, 2000
INVENTOR(S) : Yang Wang et al.

It is certified that error appears in the above-identified patent and that said Letters Patent is hereby corrected as shown below:

Column 34,
Line 2, please replace "O-fucosylliansferases", with -- O-fucosyltransferases --.
Line 9, at the beginning of the line, please replace "Cuellc" with -- Cuello --.

Column 41,
Line 27, after "kept" and before "on ice", please replace "i-old" with -- cold --.
Line 40, at the end of the line, please replace "off1" with -- off --.

Column 44,
Line 29, after "in the" and before "reticulum", please replace "eridoplasmic" with -- endoplasmic --.

Signed and Sealed this

Eighth Day of January, 2002

*Attest:*

JAMES E. ROGAN
*Attesting Officer*    *Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 1514 base pairs
        (B) TYPE: Nucleic Acid
        (C) STRANDEDNESS: Single
        (D) TOPOLOGY: Linear (xi) SEQUENCE DESCRIPTION: SEQ ID NO:1:

```
ATGCCCGCGG GCTCCTGGGA CCCGGCCGGT TACCTGCTCT ACTGCCCCTG          50

CATGGGGCGC TTTGGGAACC AGGCCGATCA CTTCTTGGGC TCTCTGGCAT         100

TTGCAAAGCT GCTAAACCGT ACCTTGGCTG TCCCTCCTTG GATTGAGTAC         150

CAGCATCACA AGCCTCCTTT CACCAACCTC CATGTGTCCT ACCAGAAGTA         200

CTTCAAGCTG GAGCCCCTCC AGGCTTACCA TCGGGTCATC AGCTTGGAGG         250

ATTTCATGGA GAAGCTGGCA CCCACCCACT GGCCCCCTGA GAAGCGGGTG         300

GCATACTGCT TGAGGTGGC AGCCCAGCGA AGCCCAGATA AGAAGACGTG          350

CCCCATGAAG GAAGGAAACC CCTTTGGCCC ATTCTGGGAT CAGTTTCATG         400

TGAGTTTCAA CAAGTCGGAG CTTTTTACAG GCATTTCCTT CAGTGCTTCC         450

TACAGAGAAC AATGGAGCCA GAGATTTCT CCAAAGGAAC ATCCGGTGCT          500

TGCCCTGCCA GGAGCCCCAG CCCAGTTCCC CGTCCTAGAA GAACACAGGC         550

CACTACAGAA GTACATGGTA TGGTCAGACG AAATGGTGAA GACGGGAGAG         600

GCCCAGATTC ATGCCCACCT TGTCCGGCCC TATGTGGGCA TTCATCTGCG         650

CATTGGCTCT GACTGGAAGA ACGCCTGTGC CATGCTGAAG GACGGGACTG         700

CAGGCTCGCA CTTCATGGCC TCTCCGCAGT GTGTGGGCTA CAGCCGCAGC         750

ACAGCGGCCC CCCTCACGAT GACTATGTGC CTGCCCTGACC TGAAGGAGAT        800

CCAGAGGGCT GTGAAGCTCT GGGTGAGGTC GCTGGATGCC CAGTCGGTCT         850
```

```
ACGTTGCTAC TGATTCCGAG AGTTATGTGC CTGAGCTCCA ACAGCTCTTC      900

AAAGGGAAGG TGAAGGTGGT GAGCCTGAAG CCTGAGGTGG CCCAGGTCGA      950

CCTGTACATC CTCGGCCAAG CCGACCACTT TATTGGCAAC TGTGTCTCCT     1000

CCTTCACTGC CTTTGTGAAG CGGGAGCGGG ACCTCCAGGG GAGGCCGTCT     1050

TCTTTCTTCG GCATGGACAG GCCCCCTAAG CTGCGGGACG AGTTCTGATT     1100

CTGGCCGGAG CACCAGACCC TCTGATCCTG GAGGGACCAG AGTCTGAGCT     1150

GGTCCTTCCA GCCAGGCCTG GCAGCCGAGG GTGCTCCGGG ATTGCAAACT     1200

CCTCTTCTCA CCTGCCAAAG ATGGAGAAGA GTGCCAGGGA CCCCTCAAGG     1250

AGGGAGACGC TCCATATCCC AGGGCATAGG ACTTGCAGGT TCCTAGGAGC     1300

AGGAGCATCT CCCATCGCAC GTGCTTTCTG CTCTTCTGGG AATTTCTCAC     1350

ACTGGCAAAG CAGTCCAGCC TCCGTCTTCT GGTCCACTCT GCTCTGAGCA     1400

GCCTGGGATG CTGAACTCTT CAGAGAGATT TTTTTATAGA GAGATTTCTA     1450

TAATTTTGAT ACAAGGTCAT GACTATCCTA GAACTCTCTG TGGTTTTTGA     1500

AAATCATTGA ATTC                                           1514
```

(2) INFORMATION FOR SEQ ID NO:2:

(i) SEQUENCE CHARACTERISTICS:
        (A) LENGTH: 365 amino acids
        (B) TYPE: Amino Acid
        (D) TOPOLOGY: Linear (xi) SEQUENCE DESCRIPTION: SEQ ID NO:2:

```
Met Pro Ala Gly Ser Trp Asp Pro Ala Gly Tyr Leu Leu Tyr Cys
 1               5                  10                  15

Pro Cys Met Gly Arg Phe Gly Asn Gln Ala Asp His Phe Leu Gly
                20                  25                  30

Ser Leu Ala Phe Ala Lys Leu Leu Asn Arg Thr Leu Ala Val Pro
                35                  40                  45

Pro Trp Ile Glu Tyr Gln His His Lys Pro Pro Phe Thr Asn Leu
                50                  55                  60

His Val Ser Tyr Gln Lys Tyr Phe Lys Leu Glu Pro Leu Gln Ala
                65                  70                  75

Tyr His Arg Val Ile Ser Leu Glu Asp Phe Met Glu Lys Leu Ala
                80                  85                  90

Pro Thr His Trp Pro Pro Glu Lys Arg Val Ala Tyr Cys Phe Glu
                95                 100                 105

Val Ala Ala Gln Arg Ser Pro Asp Lys Lys Thr Cys Pro Met Lys
               110                 115                 120

Glu Gly Asn Pro Phe Gly Pro Phe Trp Asp Gln Phe His Val Ser
               125                 130                 135

Phe Asn Lys Ser Glu Leu Phe Thr Gly Ile Ser Phe Ser Ala Ser
               140                 145                 150

Tyr Arg Glu Gln Trp Ser Gln Arg Phe Ser Pro Lys Glu His Pro
               155                 160                 165

Val Leu Ala Leu Pro Gly Ala Pro Ala Gln Phe Pro Val Leu Glu
               170                 175                 180

Glu His Arg Pro Leu Gln Lys Tyr Met Val Trp Ser Asp Glu Met
               185                 190                 195

Val Lys Thr Gly Glu Ala Gln Ile His Ala His Leu Val Arg Pro
               200                 205                 210
```

```
Tyr Val Gly Ile His Leu Arg Ile Gly Ser Asp Trp Lys Asn Ala
                215                 220                 225

Cys Ala Met Leu Lys Asp Gly Thr Ala Gly Ser His Phe Met Ala
                230                 235                 240

Ser Pro Gln Cys Val Gly Tyr Ser Arg Ser Thr Ala Ala Pro Leu
                245                 250                 255

Thr Met Thr Met Cys Leu Pro Asp Leu Lys Glu Ile Gln Arg Ala
                260                 265                 270

Val Lys Leu Trp Val Arg Ser Leu Asp Ala Gln Ser Val Tyr Val
                275                 280                 285

Ala Thr Asp Ser Glu Ser Tyr Val Pro Glu Leu Gln Gln Leu Phe
                290                 295                 300

Lys Gly Lys Val Lys Val Val Ser Leu Lys Pro Glu Val Ala Gln
                305                 310                 315

Val Asp Leu Tyr Ile Leu Gly Gln Ala Asp His Phe Ile Gly Asn
                320                 325                 330

Cys Val Ser Ser Phe Thr Ala Phe Val Lys Arg Glu Arg Asp Leu
                335                 340                 345

Gln Gly Arg Pro Ser Ser Phe Phe Gly Met Asp Arg Pro Pro Lys
                350                 355                 360

Leu Arg Asp Glu Phe
                365
```

(2) INFORMATION FOR SEQ ID NO:3:

(i) SEQUENCE CHARACTERISTICS:
        (A) LENGTH: 61 amino acids
        (B) TYPE: Amino Acid
        (D) TOPOLOGY: Linear (xi) SEQUENCE DESCRIPTION: SEQ ID NO:3:

```
Arg Leu Ala Gly Ser Trp Asp Leu Ala Gly Tyr Leu Leu Tyr Xaa
 1               5                  10                  15

Pro Xaa Met Gly Arg Phe Gly Asn Gln Ala Asp His Phe Leu Gly
                20                  25                  30

Ser Leu Ala Phe Ala Lys Leu Xaa Val Arg Thr Leu Ala Val Pro
                35                  40                  45

Pro Trp Ile Glu Tyr Gln His His Lys Pro Pro Phe Thr Asn Leu
                50                  55                  60

His
 61
```

(2) INFORMATION FOR SEQ ID NO:4:

(i) SEQUENCE CHARACTERISTICS:
        (A) LENGTH: 1300 base pairs
        (B) TYPE: Nucleic Acid
        (C) STRANDEDNESS: Single
        (D) TOPOLOGY: Linear (xi) SEQUENCE DESCRIPTION: SEQ ID NO:4:

```
TTATTCATAC CGTCCCACCA TCGGGCGCGG ATCAGATCCA TGGCCAAGTT          50

CCTGGTCAAC GTGGCCCTGC TGCTGCTGCT GCTGCTGCTG TCCGGAGCCT         100

GGGCCCATAT GAGATCCCAT CACCATCACC ATCACATGCC CGCGGGCTCC         150

TGGGACCCGG CCGGTTACCT GCTCTACTGC CCCTGCATGG GGCGCTTTGG         200

GAACCAGGCC GATCACTTCT TGGGCTCTCT GGCATTTGCA AAGCTGCTAA         250
```

| | |
|---|---|
| ACCGTACCTT GGCTGTCCCT CCTTGGATTG AGTACCAGCA TCACAAGCCT | 300 |
| CCTTTCACCA ACCTCCATGT GTCCTACCAG AAGTACTTCA AGCTGGAGCC | 350 |
| CCTCCAGGCT TACCATCGGG TCATCAGCTT GGAGGATTTC ATGGAGAAGC | 400 |
| TGGCACCCAC CCACTGGCCC CCTGAGAAGC GGGTGGCATA CTGCTTTGAG | 450 |
| GTGGCAGCCC AGCGAAGCCC AGATAAGAAG ACGTGCCCCA TGAAGGAAGG | 500 |
| AAACCCCTTT GGCCCATTCT GGGATCAGTT TCATGTGAGT TTCAACAAGT | 550 |
| CGGAGCTTTT TACAGGCATT TCCTTCAGTG CTTCCTACAG AGAACAATGG | 600 |
| AGCCAGAGAT TTTCTCCAAA GGAACATCCG GTGCTTGCCC TGCCAGGAGC | 650 |
| CCCAGCCCAG TTCCCCGTCC TAGAGGAACA CAGGCCACTA CAGAAGTACA | 700 |
| TGGTATGGTC AGACGAAATG GTGAAGACGG GAGAGGCCCA GATTCATGCC | 750 |
| CACCTTGTCC GGCCCTATGT GGGCATTCAT CTGCGCATTG GCTCTGACTG | 800 |
| GAAGAACGCC TGTGCCATGC TGAAGGACGG GACTGCAGGC TCGCACTTCA | 850 |
| TGGCCTCTCC GCAGTGTGTG GGCTACAGCC GCAGCACAGC GGCCCCCCTC | 900 |
| ACGATGACTA TGTGCCTGCC TGACCTGAAG GAGATCCAGA GGGCTGTGAA | 950 |
| GCTCTGGGTG AGGTCGCTGG ATGCCCAGTC GGTCTACGTT GCTACTGATT | 1000 |
| CCGAGAGTTA TGTGCCTGAG CTCCAACAGC TCTTCAAAGG GAAGGTGAAG | 1050 |
| GTGGTGAGCC TGAAGCCTGA GGTGGCCCAG GTCGACCTGT ACATCCTCGG | 1100 |
| CCAAGCCGAC CACTTTATTG CAACTGTGT CTCCTCCTTC ACTGCCTTTG | 1150 |
| TGAAGCGGGA GCGGGACCTC CAGGGGAGGC CGTCTTCTTT CTTCGGCATG | 1200 |
| GACAGGCCCC CTAAGCTGCG GGACGAGTTC TGATTCTGGC CGGAGCACCA | 1250 |
| GACCCTCTGA TCCTGGAGGG ACCAGAGTCT GAGCTGGTCC TTCCAGCCAG | 1300 |

(2) INFORMATION FOR SEQ ID NO:5:

(i) SEQUENCE CHARACTERISTICS:
        (A) LENGTH: 11284 base pairs
        (B) TYPE: Nucleic Acid
        (C) STRANDEDNESS: Single
        (D) TOPOLOGY: Linear (xi) SEQUENCE DESCRIPTION: SEQ ID NO:5:

| | |
|---|---|
| AAGCTTTACT CGTAAAGCGA GTTGAAGGAT CATATTTAGT TGCGTTTATG | 50 |
| AGATAAGATT GAAAGCACGT GTAAAATGTT TCCCGCGCGT TGGCACAACT | 100 |
| ATTTACAATG CGGCCAAGTT ATAAAAGATT CTAATCTGAT ATGTTTTAAA | 150 |
| ACACCTTTGC GGCCCGAGTT GTTTGCGTAC GTGACTAGCG AAGAAGATGT | 200 |
| GTGGACCGCA GAACAGATAG TAAAACAAAA CCCTAGTATT GGAGCAATAA | 250 |
| TCGATTTAAC CAACACGTCT AAATATTATG ATGGTGTGCA TTTTTTGCGG | 300 |
| GCGGGCCTGT TATACAAAAA AATTCAAGTA CCTGGCCAGA CTTTGCCGCC | 350 |
| TGAAAGCATA GTTCAAGAAT TTATTGACAC GGTAAAAGAA TTTACAGAAA | 400 |
| AGTGTCCCGG CATGTTGGTG GGCGTGCACT GCACACACG TATTAATCGC | 450 |
| ACCGGTTACA TGGTGTGCAG ATATTTAATG CACACCCTGG GTATTGCGCC | 500 |
| GCAGGAAGCC ATAGATAGAT TCGAAAAAGC CAGAGGTCAC AAAATTGAAA | 550 |
| GACAAAATTA CGTTCAAGAT TTATTAATTT AATTAATATT ATTTGCATTC | 600 |
| TTTAACAAAT ACTTTATCCT ATTTTCAAAT TGTTGCGCTT CTTCCAGCGA | 650 |

-continued

| | | |
|---|---|---|
| ACCAAAACTA TGCTTCGCTT GCTCCGTTTA GCTTGTAGCC GATCAGTGGC | 700 |
| GTTGTTCCAA TCGACGGTAG GATTAGGCCG GATATTCTCC ACCACAATGT | 750 |
| TGGCAACGTT GATGTTACGT TTATGCTTTT GGTTTTCCAC GTACGTCTTT | 800 |
| TGGCCGGTAA TAGCCGTAAA CGTAGTGCCG TCGCGCGTCA CGCACAACAC | 850 |
| CGGATGTTTG CGCTTGTCCG CGGGGTATTG AACCGCGCGA TCCGACAAAT | 900 |
| CCACCACTTT GGCAACTAAA TCGGTGACCT GCGCGTCTTT TTTCTGCATT | 950 |
| ATTTCGTCTT TCTTTTGCAT GGTTTCCTGG AAGCCGGTGT ACATGCGGTT | 1000 |
| TAGATCAGTC ATGACGCGCG TGACCTGCAA ATCTTTGGCC TCGATCTGCT | 1050 |
| TGTCCTTGAT GGCAACGATG CGTTCAATAA ACTCTTGTTT TTTAACAAGT | 1100 |
| TCCTCGGTTT TTTGCGCCAC CACCGCTTGC AGCGCGTTTG TGTGCTCGGT | 1150 |
| GAATGTCGCA ATCAGCTTAG TCACCAACTG TTTGCTCTCC TCCTCCCGTT | 1200 |
| GTTTGATCGC GGGATCGTAC TTGCCGGTGC AGAGCACTTG AGGAATTACT | 1250 |
| TCTTCTAAAA GCCATTCTTG TAATTCTATG GCGTAAGGCA ATTTGGACTT | 1300 |
| CATAATCAGC TGAATCACGC CGGATTTAGT AATGAGCACT GTATGCGGCT | 1350 |
| GCAAATACAG CGGGTCGCCC CTTTTCACGA CGCTGTTAGA GGTAGGGCCC | 1400 |
| CCATTTTGGA TGGTCTGCTC AAATAACGAT TTGTATTTAT TGTCTACATG | 1450 |
| AACACGTATA GCTTTATCAC AAACTGTATA TTTTAAACTG TTAGCGACGT | 1500 |
| CCTTGGCCAC GAACCGGACC TGTTGGTCGC GCTCTAGCAC GTACCGCAGG | 1550 |
| TTGAACGTAT CTTCTCCAAA TTTAAATTCT CCAATTTTAA CGCGAGCCAT | 1600 |
| TTTGATACAC GTGTGTCGAT TTTGCAACAA CTATTGTTTT TTAACGCAAA | 1650 |
| CTAAACTTAT TGTGGTAAGC AATAATTAAA TATGGGGGAA CATGCGCCGC | 1700 |
| TACAACACTC GTCGTTATGA ACGCAGACGG CGCCGGTCTC GGCGCAAGCG | 1750 |
| GCTAAAACGT GTTGCGCGTT CAACGCGGCA ACATCGCAA AAGCCAATAG | 1800 |
| TACAGTTTTG ATTTGCATAT TAACGGCGAT TTTTTAAATT ATCTTATTTA | 1850 |
| ATAAATAGTT ATGACGCCTA CAACTCCCCG CCCGCGTTGA CTCGCTGCAC | 1900 |
| CTCGAGCAGT TCGTTGACGC CTTCCTCCGT GTGGCCGAAC ACGTCGAGCG | 1950 |
| GGTGGTCGAT GACCAGCGGC GTGCCGCACG CGACGCACAA GTATCTGTAC | 2000 |
| ACCGAATGAT CGTCGGGCGA AGGCACGTCG GCCTCCAAGT GGCAATATTG | 2050 |
| GCAAATTCGA AAATATATAC AGTTGGGTTG TTTGCGCATA TCTATCGTGG | 2100 |
| CGTTGGGCAT GTACGTCCGA ACGTTGATTT GCATGCAAGC CGAAATTAAA | 2150 |
| TCATTGCGAT TAGTGCGATT AAAACGTTGT ACATCCTCGC TTTTAATCAT | 2200 |
| GCCGTCGATT AAATCGCGCA ATCGAGTCAA GTGATCAAAG TGTGGAATAA | 2250 |
| TGTTTTCTTT GTATTCCCGA GTCAAGCGCA GCGCGTATTT TAACAAACTA | 2300 |
| GCCATCTTGT AAGTTAGTTT CATTTAATGC AACTTTATCC AATAATATAT | 2350 |
| TATGTATCGC ACGTCAAGAA TTAACAATGC GCCCGTTGTC GCATCTCAAC | 2400 |
| ACGACTATGA TAGAGATCAA ATAAAGCGCG AATTAAATAG CTTGCGACGC | 2450 |
| AACGTGCACG ATCTGTGCAC GCGTTCCGGC ACGAGCTTTG ATTGTAATAA | 2500 |
| GTTTTTACGA AGCGATGACA TGACCCCCGT AGTGACAACG ATCACGCCCA | 2550 |
| AAAGAACTGC CGACTACAAA ATTACCGAGT ATGTCGGTGA CGTTAAAACT | 2600 |
| ATTAAGCCAT CCAATCGACC GTTAGTCGAA TCAGGACCGC TGGTGCGAGA | 2650 |

```
AGCCGCGAAG TATGGCGAAT GCATCGTATA ACGTGTGGAG TCCGCTCATT    2700

AGAGCGTCAT GTTAGACAA GAAAGCTACA TATTTAATTG ATCCCGATGA    2750

TTTTATTGAT AAATTGACCC TAACTCCATA CACGGTATTC TACAATGGCG    2800

GGGTTTTGGT CAAAATTTCC GGACTGCGAT TGTACATGCT GTTAACGGCT    2850

CCGCCCACTA TTAATGAAAT TAAAAATTCC AATTTTAAAA AACGCAGCAA    2900

GAGAAACATT TGTATGAAAG AATGCGTAGA AGGAAAGAAA AATGTCGTCG    2950

ACATGCTGAA CAACAAGATT AATATGCCTC CGTGTATAAA AAAAATATTG    3000

AACGATTTGA AGAAAACAA TGTACCGCGC GGCGGTATGT ACAGGAAGAG    3050

GTTTATACTA AACTGTTACA TTGCAAACGT GGTTTCGTGT GCCAAGTGTG    3100

AAAACCGATG TTTAATCAAG GCTCTGACGC ATTTCTACAA CCACGACTCC    3150

AAGTGTGTGG GTGAAGTCAT GCATCTTTTA ATCAAATCCC AAGATGTGTA    3200

TAAACCACCA AACTGCCAAA AAATGAAAAC TGTCGACAAG CTCTGTCCGT    3250

TTGCTGGCAA CTGCAAGGGT CTCAATCCTA TTTGTAATTA TTGAATAATA    3300

AAACAATTAT AAATGCTAAA TTTGTTTTTT ATTAACGATA CAAACCAAAC    3350

GCAACAAGAA CATTTGTAGT ATTATCTATA ATTGAAAACG CGTAGTTATA    3400

ATCGCTGAGG TAATATTTAA AATCATTTTC AAATGATTCA CAGTTAATTT    3450

GCGACAATAT AATTTTATTT TCACATAAAC TAGACGCCTT GTCGTCTTCT    3500

TCTTCGTATT CCTTCTCTTT TTCATTTTTC TCCTCATAAA AATTAACATA    3550

GTTATTATCG TATCCATATA TGTATCTATC GTATAGAGTA AATTTTTTGT    3600

TGTCATAAAT ATATATGTCT TTTTTAATGG GGTGTATAGT ACCGCTGCGC    3650

ATAGTTTTTC TGTAATTTAC AACAGTGCTA TTTTCTGGTA GTTCTTCGGA    3700

GTGTGTTGCT TTAATTATTA AATTTATATA ATCAATGAAT TTGGGATCGT    3750

CGGTTTTGTA CAATATGTTG CCGGCATAGT ACGCAGCTTC TTCTAGTTCA    3800

ATTACACCAT TTTTTAGCAG CACCGGATTA ACATAACTTT CCAAAATGTT    3850

GTACGAACCG TTAAACAAAA ACAGTTCACC TCCCTTTTCT ATACTATTGT    3900

CTGCGAGCAG TTGTTTGTTG TTAAAAATAA CAGCCATTGT AATGAGACGC    3950

ACAAACTAAT ATCACAAACT GGAAATGTCT ATCAATATAT AGTTGCTGAT    4000

ATCATGGAGA TAATTAAAAT GATAACCATC TCGCAAATAA ATAAGTATTT    4050

TACTGTTTTC GTAACAGTTT TGTAATAAAA AAACCTATAA ATATTCCGGA    4100

TTATTCATAC CGTCCCACCA TCGGGCGCGG ATCAGATCCA TGGCCAAGTT    4150

CCTGGTCAAC GTGGCCCTGC TGCTGCTGCT GCTGCTGCTG TCCGGAGCCT    4200

GGGCCCATAT GAGATCCCAT CACCATCACC ATCACATGCC CGCGGGCTCC    4250

TGGGACCCGG CCGGTTACCT GCTCTACTGC CCCTGCATGG GGCGCTTTGG    4300

GAACCAGGCC GATCACTTCT TGGGCTCTCT GGCATTTGCA AAGCTGCTAA    4350

ACCGTACCTT GGCTGTCCCT CCTTGGATTG AGTACCAGCA TCACAAGCCT    4400

CCTTTCACCA ACCTCCATGT GTCCTACCAG AAGTACTTCA AGCTGGAGCC    4450

CCTCCAGGCT TACCATCGGG TCATCAGCTT GGAGGATTTC ATGGAGAAGC    4500

TGGCACCCAC CCACTGGCCC CCTGAGAAGC GGGTGGCATA CTGCTTTGAG    4550

GTGGCAGCCC AGCGAAGCCC AGATAAGAAG ACGTGCCCCA TGAAGGAAGG    4600

AAACCCCTTT GGCCCATTCT GGGATCAGTT TCATGTGAGT TTCAACAAGT    4650
```

| | |
|---|---|
| CGGAGCTTTT TACAGGCATT TCCTTCAGTG CTTCCTACAG AGAACAATGG | 4700 |
| AGCCAGAGAT TTTCTCCAAA GGAACATCCG GTGCTTGCCC TGCCAGGAGC | 4750 |
| CCCAGCCCAG TTCCCCGTCC TAGAGGAACA CAGGCCACTA CAGAAGTACA | 4800 |
| TGGTATGGTC AGACGAAATG GTGAAGACGG GAGAGGCCCA GATTCATGCC | 4850 |
| CACCTTGTCC GGCCCTATGT GGGCATTCAT CTGCGCATTG GCTCTGACTG | 4900 |
| GAAGAACGCC TGTGCCATGC TGAAGGACGG GACTGCAGGC TCGCACTTCA | 4950 |
| TGGCCTCTCC GCAGTGTGTG GGCTACAGCC GCAGCACAGC GGCCCCCCTC | 5000 |
| ACGATGACTA TGTGCCTGCC TGACCTGAAG GAGATCCAGA GGGCTGTGAA | 5050 |
| GCTCTGGGTG AGGTCGCTGG ATGCCCAGTC GGTCTACGTT GCTACTGATT | 5100 |
| CCGAGAGTTA TGTGCCTGAG CTCCAACAGC TCTTCAAAGG GAAGGTGAAG | 5150 |
| GTGGTGAGCC TGAAGCCTGA GGTGGCCCAG GTCGACCTGT ACATCCTCGG | 5200 |
| CCAAGCCGAC CACTTTATTG GCAACTGTGT CTCCTCCTTC ACTGCCTTTG | 5250 |
| TGAAGCGGGA GCGGGACCTC CAGGGGAGGC CGTCTTCTTT CTTCGGCATG | 5300 |
| GACAGGCCCC CTAAGCTGCG GGACGAGTTC TGATTCTGGC CGGAGCACCA | 5350 |
| GACCCTCTGA TCCTGGAGGG ACCAGAGTCT GAGCTGGTCC TTCCAGCCAG | 5400 |
| GCCTGGCAGC CAGAGGTGCT CCGGGATTGC AAACTCCTCT TCTCACCTGC | 5450 |
| CAAAGATGGA GAAGAGTGCC AGGGACCCCT CAAGGAGGGA GACGCTCCAT | 5500 |
| ATCCCAGGGC ATAGGACTTG CAGGTTCCTA GGAGCAGGAG CATCTCCCAT | 5550 |
| CGCACGTGCT TTCTGCTCTT CTGGGAATTT CTCACACTGG CAAAGCAGTC | 5600 |
| CAGCCTCCGT CTTCTGGTCC ACTCTGCTCT GAGCAGCCTG GGATGCTGAA | 5650 |
| CTCTTCAGAG AGATTTTTTT ATAGAGAGAT TTCTATAATT TTGATACAAG | 5700 |
| GTCATGACTA TCCTAGAACT CTCTGTGGTT TTTGAAAATC ATTGAATTCC | 5750 |
| TGCAGCCCGG GGGATCCACT AGTTCTAGTT CTAGAGCGGC CGCTCCAGAA | 5800 |
| TTCTAGAAGG TACCCGGGAT CCTTTCCTGG GACCCGGCAA GAACCAAAAA | 5850 |
| CTCACTCTCT TCAAGGAAAT CCGTAATGTT AAACCCGACA CGATGAAGCT | 5900 |
| TGTCGTTGGA TGGAAAGGAA AAGAGTTCTA CAGGGAAACT TGGACCCGCT | 5950 |
| TCATGGAAGA CAGCTTCCCC ATTGTTAACG ACCAAGAAGT GATGGATGTT | 6000 |
| TTCCTTGTTG TCAACATGCG TCCCACTAGA CCCAACCGTT GTTACAAATT | 6050 |
| CCTGGCCCAA CACGCTCTGC GTTGCGACCC CGACTATGTA CCTCATGACG | 6100 |
| TGATTAGGAT CGTCGAGCCT TCATGGGTGG GCAGCAACAA CGAGTACCGC | 6150 |
| ATCAGCCTGG CTAAGAAGGG CGGCGGCTGC CCAATAATGA ACCTTCACTC | 6200 |
| TGAGTACACC AACTCGTTCG AACAGTTCAT CGATCGTGTC ATCTGGGAGA | 6250 |
| ACTTCTACAA GCCCATCGTT TACATCGGTA CCGACTCTGC TGAAGAGGAG | 6300 |
| GAAATTCTCC TTGAAGTTTC CCTGGTGTTC AAAGTAAAGG AGTTTGCACC | 6350 |
| AGACGCACCT CTGTTCACTG GTCCGGCGTA TTAAAACACG ATACATTGTT | 6400 |
| ATTAGTACAT TTATTAAGCG CTAGATTCTG TGCGTTGTTG ATTTACAGAC | 6450 |
| AATTGTTGTA CGTATTTTAA TAATTCATTA AATTTATAAT CTTTAGGGTG | 6500 |
| GTATGTTAGA GCGAAAATCA AATGATTTTC AGCGTCTTTA TATCTGAATT | 6550 |
| TAAATATTAA ATCCTCAATA GATTTGTAAA ATAGGTTTCG ATTAGTTTCA | 6600 |
| AACAAGGGTT GTTTTTCCGA ACCGATGGCT GGACTATCTA ATGGATTTTC | 6650 |

| | |
|---|---|
| GCTCAACGCC ACAAAACTTG CCAAATCTTG TAGCAGCAAT CTAGCTTTGT | 6700 |
| CGATATTCGT TTGTGTTTTG TTTTGTAATA AAGGTTCGAC GTCGTTCAAA | 6750 |
| ATATTATGCG CTTTTGTATT TCTTTCATCA CTGTCGTTAG TGTACAATTG | 6800 |
| ACTCGACGTA AACACGTTAA ATAAAGCTTG GACATATTTA ACATCGGGCG | 6850 |
| TGTTAGCTTT ATTAGGCCGA TTATCGTCGT CGTCCCAACC CTCGTCGTTA | 6900 |
| GAAGTTGCTT CCGAAGACGA TTTTGCCATA GCCACACGAC GCCTATTAAT | 6950 |
| TGTGTCGGCT AACACGTCCG CGATCAAATT TGTAGTTGAG CTTTTTGGAA | 7000 |
| TTATTTCTGA TTGCGGGCGT TTTTGGGCGG GTTTCAATCT AACTGTGCCC | 7050 |
| GATTTTAATT CAGACAACAC GTTAGAAAGC GATGGTGCAG GCGGTGGTAA | 7100 |
| CATTTCAGAC GGCAAATCTA CTAATGGCGG CGGTGGTGGA GCTGATGATA | 7150 |
| AATCTACCAT CGGTGGAGGC GCAGGCGGGG CTGGCGGCGG AGGCGGAGGC | 7200 |
| GGAGGTGGTG GCGGTGATGC AGACGGCGGT TTAGGCTCAA ATGTCTCTTT | 7250 |
| AGGCAACACA GTCGGCACCT CAACTATTGT ACTGGTTTCG GGCGCCGTTT | 7300 |
| TTGGTTTGAC CGGTCTGAGA CGAGTGCGAT TTTTTTCGTT TCTAATAGCT | 7350 |
| TCCAACAATT GTTGTCTGTC GTCTAAAGGT GCAGCGGGTT GAGGTTCCGT | 7400 |
| CGGCATTGGT GGAGCGGGCG GCAATTCAGA CATCGATGGT GGTGGTGGTG | 7450 |
| GTGGAGGCGC TGGAATGTTA GGCACGGGAG AAGGTGGTGG CGGCGGTGCC | 7500 |
| GCCGGTATAA TTTGTTCTGG TTTAGTTTGT TCGCGCACGA TTGTGGGCAC | 7550 |
| CGGCGCAGGC GCCGCTGGCT GCACAACGGA AGGTCGTCTG CTTCGAGGCA | 7600 |
| GCGCTTGGGG TGGTGGCAAT TCAATATTAT AATTGGAATA CAAATCGTAA | 7650 |
| AAATCTGCTA TAAGCATTGT AATTTCGCTA TCGTTTACCG TGCCGATATT | 7700 |
| TAACAACCGC TCAATGTAAG CAATTGTATT GTAAAGAGAT TGTCTCAAGC | 7750 |
| TCCGCACGCC GATAACAAGC CTTTTCATTT TTACTACAGC ATTGTAGTGG | 7800 |
| CGAGACACTT CGCTGTCGTC GACGTACATG TATGCTTTGT TGTCAAAAAC | 7850 |
| GTCGTTGGCA AGCTTTAAAA TATTTAAAAG AACATCTCTG TTCAGCACCA | 7900 |
| CTGTGTTGTC GTAAATGTTG TTTTTGATAA TTTGCGCTTC CGCAGTATCG | 7950 |
| ACACGTTCAA AAAATTGATG CGCATCAATT TTGTTGTTCC TATTATTGAA | 8000 |
| TAAATAAGAT TGTACAGATT CATATCTACG ATTCGTCATG GCCACCACAA | 8050 |
| ATGCTACGCT GCAAACGCTG GTACAATTTT ACGAAAACTG CAAAAACGTC | 8100 |
| AAAACTCGGT ATAAAATAAT CAACGGGCGC TTTGGCAAAA TATCTATTTT | 8150 |
| ATCGCACAAG CCCACTAGCA AATTGTATTT GCAGAAAACA ATTTCGGCGC | 8200 |
| ACAATTTTAA CGCTGACGAA ATAAAAGTTC ACCAGTTAAT GAGCGACCAC | 8250 |
| CCAAATTTTA TAAAAATCTA TTTTAATCAC GGTTCCATCA ACAACCAAGT | 8300 |
| GATCGTGATG GACTACATTG ACTGTCCCGA TTTATTTGAA ACACTACAAA | 8350 |
| TTAAAGGCGA GCTTTCGTAC CAACTTGTTA GCAATATTAT TAGACAGCTG | 8400 |
| TGTGAAGCGC TCAACGATTT GCACAAGCAC AATTTCATAC ACAACGACAT | 8450 |
| AAAACTCGAA AATGTCTTAT ATTTCGAAGC ACTTGATCGC GTGTATGTTT | 8500 |
| GCGATTACGG ATTGTGCAAA CACGAAAACT CACTTAGCGT GCACGACGGC | 8550 |
| ACGTTGGAGT ATTTTAGTCC GGAAAAAATT CGACACACAA CTATGCACGT | 8600 |
| TTCGTTTGAC TGGTACGCGG CGTGTTAACA TACAAGTTGC TAACCGGCGG | 8650 |

| | |
|---|---|
| TTCGTAATCA TGGTCATAGC TGTTTCCTGT GTGAAATTGT TATCCGCTCA | 8700 |
| CAATTCCACA CAACATACGA GCCGGAAGCA TAAAGTGTAA AGCCTGGGGT | 8750 |
| GCCTAATGAG TGAGCTAACT CACATTAATT GCGTTGCGCT CACTGCCCGC | 8800 |
| TTTCCAGTCG GGAAACCTGT CGTGCCAGCT GCATTAATGA ATCGGCCAAC | 8850 |
| GCGCGGGGAG AGGCGGTTTG CGTATTGGGC GCTCTTCCGC TTCCTCGCTC | 8900 |
| ACTGACTCGC TGCGCTCGGT CGTTCGGCTG CGGCGAGCGG TATCAGCTCA | 8950 |
| CTCAAAGGCG GTAATACGGT TATCCACAGA ATCAGGGGAT AACGCAGGAA | 9000 |
| AGAACATGTG AGCAAAAGGC CAGCAAAAGG CCAGGAACCG TAAAAAGGCC | 9050 |
| GCGTTGCTGG CGTTTTTCCA TAGGCTCCGC CCCCCTGACG AGCATCACAA | 9100 |
| AAATCGACGC TCAAGTCAGA GGTGGCGAAA CCCGACAGGA CTATAAAGAT | 9150 |
| ACCAGGCGTT TCCCCCTGGA AGCTCCCTCG TGCGCTCTCC TGTTCCGACC | 9200 |
| CTGCCGCTTA CCGGATACCT GTCCGCCTTT CTCCCTTCGG GAAGCGTGGC | 9250 |
| GCTTTCTCAT AGCTCACGCT GTAGGTATCT CAGTTCGGTG TAGGTCGTTC | 9300 |
| GCTCCAAGCT GGGCTGTGTG CACGAACCCC CCGTTCAGCC CGACCGCTGC | 9350 |
| GCCTTATCCG GTAACTATCG TCTTGAGTCC AACCCGGTAA GACACGACTT | 9400 |
| ATCGCCACTG GCAGCAGCCA CTGGTAACAG GATTAGCAGA GCGAGGTATG | 9450 |
| TAGGCGGTGC TACAGAGTTC TTGAAGTGGT GGCCTAACTA CGGCTACACT | 9500 |
| AGAAGGACAG TATTTGGTAT CTGCGCTCTG CTGAAGCCAG TTACCTTCGG | 9550 |
| AAAAAGAGTT GGTAGCTCTT GATCCGGCAA ACAAACCACC GCTGGTAGCG | 9600 |
| GTGGTTTTTT TGTTTGCAAG CAGCAGATTA CGCGCAGAAA AAAAGGATCT | 9650 |
| CAAGAAGATC CTTTGATCTT TTCTACGGGG TCTGACGCTC AGTGGAACGA | 9700 |
| AAACTCACGT TAAGGGATTT TGGTCATGAG ATTATCAAAA AGGATCTTCA | 9750 |
| CCTAGATCCT TTTAAATTAA AAATGAAGTT TTAAATCAAT CTAAAGTATA | 9800 |
| TATGAGTAAA CTTGGTCTGA CAGTTACCAA TGCTTAATCA GTGAGGCACC | 9850 |
| TATCTCAGCG ATCTGTCTAT TTCGTTCATC CATAGTTGCC TGACTCCCCG | 9900 |
| TCGTGTAGAT AACTACGATA CGGGAGGGCT TACCATCTGG CCCCAGTGCT | 9950 |
| GCAATGATAC CGCGAGACCC ACGCTCACCG GCTCCAGATT TATCAGCAAT | 10000 |
| AAACCAGCCA GCCGGAAGGG CCGAGCGCAG AAGTGGTCCT GCAACTTTAT | 10050 |
| CCGCCTCCAT CCAGTCTATT AATTGTTGCC GGGAAGCTAG AGTAAGTAGT | 10100 |
| TCGCCAGTTA ATAGTTTGCG CAACGTTGTT GCCATTGCTA CAGGCATCGT | 10150 |
| GGTGTCACGC TCGTCGTTTG GTATGGCTTC ATTCAGCTCC GGTTCCCAAC | 10200 |
| GATCAAGGCG AGTTACATGA TCCCCCATGT TGTGCAAAAA AGCGGTTAGC | 10250 |
| TCCTTCGGTC CTCCGATCGT TGTCAGAAGT AAGTTGGCCG CAGTGTTATC | 10300 |
| ACTCATGGTT ATGGCAGCAC TGCATAATTC TCTTACTGTC ATGCCATCCG | 10350 |
| TAAGATGCTT TTCTGTGACT GGTGAGTACT CAACCAAGTC ATTCTGAGAA | 10400 |
| TAGTGTATGC GGCGACCGAG TTGCTCTTGC CCGGCGTCAA TACGGGATAA | 10450 |
| TACCGCGCCA CATAGCAGAA CTTTAAAAGT GCTCATCATT GGAAAACGTT | 10500 |
| CTTCGGGGCG AAAACTCTCA AGGATCTTAC CGCTGTTGAG ATCCAGTTCG | 10550 |
| ATGTAACCCA CTCGTGCACC CAACTGATCT TCAGCATCTT TTACTTTCAC | 10600 |
| CAGCGTTTCT GGGTGAGCAA AAACAGGAAG GCAAAATGCC GCAAAAAAGG | 10650 |

```
GAATAAGGGC GACACGGAAA TGTTGAATAC TCATACTCTT CCTTTTTCAA           10700

TATTATTGAA GCATTTATCA GGGTTATTGT CTCATGAGCG GATACATATT           10750

TGAATGTATT TAGAAAAATA AACAAATAGG GGTTCCGCGC ACATTTCCCC           10800

GAAAAGTGCC ACCTGACGTC TAAGAAACCA TTATTATCAT GACATTAACC           10850

TATAAAAATA GGCGTATCAC GAGGCCCTTT CGTCTCGCGC GTTTCGGTGA           10900

TGACGGTGAA AACCTCTGAC ACATGCAGCT CCCGGAGACG GTCACAGCTT           10950

GTCTGTAAGC GGATGCCGGG AGCAGACAAG CCCGTCAGGG CGCGTCAGCG           11000

GGTGTTGGCG GGTGTCGGGG CTGGCTTAAC TATGCGGCAT CAGAGCAGAT           11050

TGTACTGAGA GTGCACCATA TATGCGGTGT GAAATACCGC ACAGATGCGT           11100

AAGGAGAAAA TACCGCATCA GGCGCCATTC GCCATTCAGG CTGCGCAACT           11150

GTTGGGAAGG GCGATCGGTG CGGGCCTCTT CGCTATTACG CCAGCTGGCG           11200

AAAGGGGGAT GTGCTGCAAG GCGATTAAGT TGGGTAACGC CAGGGTTTTC           11250

CCAGTCACGA CGTTGTAAAA CGACGGCCAG TGCC                            11284
```

(2) INFORMATION FOR SEQ ID NO:6:

(i) SEQUENCE CHARACTERISTICS:
        (A) LENGTH: 397 amino acids
        (B) TYPE: Amino Acid
        (D) TOPOLOGY: Linear (xi) SEQUENCE DESCRIPTION: SEQ ID NO:6:

```
Met Ala Lys Phe Leu Val Asn Val Ala Leu Leu Leu Leu Leu Leu
 1               5                  10                  15

Leu Leu Ser Gly Ala Trp Ala His Met Arg Ser His His His His
                20                  25                  30

His His Met Pro Ala Gly Ser Trp Asp Pro Ala Gly Tyr Leu Leu
                35                  40                  45

Tyr Cys Pro Cys Met Gly Arg Phe Gly Asn Gln Ala Asp His Phe
                50                  55                  60

Leu Gly Ser Leu Ala Phe Ala Lys Leu Leu Asn Arg Thr Leu Ala
                65                  70                  75

Val Pro Pro Trp Ile Glu Tyr Gln His His Lys Pro Pro Phe Thr
                80                  85                  90

Asn Leu His Val Ser Tyr Gln Lys Tyr Phe Lys Leu Glu Pro Leu
                95                 100                 105

Gln Ala Tyr His Arg Val Ile Ser Leu Glu Asp Phe Met Glu Lys
               110                 115                 120

Leu Ala Pro Thr His Trp Pro Pro Glu Lys Arg Val Ala Tyr Cys
               125                 130                 135

Phe Glu Val Ala Ala Gln Arg Ser Pro Asp Lys Lys Thr Cys Pro
               140                 145                 150

Met Lys Glu Gly Asn Pro Phe Gly Pro Phe Trp Asp Gln Phe His
               155                 160                 165

Val Ser Phe Asn Lys Ser Glu Leu Phe Thr Gly Ile Ser Phe Ser
               170                 175                 180

Ala Ser Tyr Arg Glu Gln Trp Ser Gln Arg Phe Ser Pro Lys Glu
               185                 190                 195

His Pro Val Leu Ala Leu Pro Gly Ala Pro Ala Gln Phe Pro Val
               200                 205                 210
```

```
Leu Glu Glu His Arg Pro Leu Gln Lys Tyr Met Val Trp Ser Asp
            215                 220                 225

Glu Met Val Lys Thr Gly Glu Ala Gln Ile His Ala His Leu Val
            230                 235                 240

Arg Pro Tyr Val Gly Ile His Leu Arg Ile Gly Ser Asp Trp Lys
            245                 250                 255

Asn Ala Cys Ala Met Leu Lys Asp Gly Thr Ala Gly Ser His Phe
            260                 265                 270

Met Ala Ser Pro Gln Cys Val Gly Tyr Ser Arg Ser Thr Ala Ala
            275                 280                 285

Pro Leu Thr Met Thr Met Cys Leu Pro Asp Leu Lys Glu Ile Gln
            290                 295                 300

Arg Ala Val Lys Leu Trp Val Arg Ser Leu Asp Ala Gln Ser Val
            305                 310                 315

Tyr Val Ala Thr Asp Ser Glu Ser Tyr Val Pro Glu Leu Gln Gln
            320                 325                 330

Leu Phe Lys Gly Lys Val Lys Val Val Ser Leu Lys Pro Glu Val
            335                 340                 345

Ala Gln Val Asp Leu Tyr Ile Leu Gly Gln Ala Asp His Phe Ile
            350                 355                 360

Gly Asn Cys Val Ser Ser Phe Thr Ala Phe Val Lys Arg Glu Arg
            365                 370                 375

Asp Leu Gln Gly Arg Pro Ser Ser Phe Phe Gly Met Asp Arg Pro
            380                 385                 390

Pro Lys Leu Arg Asp Glu Phe
            395     397

(2) INFORMATION FOR SEQ ID NO:7:

(i) SEQUENCE CHARACTERISTICS:
        (A) LENGTH: 5009 base pairs
        (B) TYPE: Nucleic Acid
        (C) STRANDEDNESS: Single
        (D) TOPOLOGY: Linear (xi) SEQUENCE DESCRIPTION: SEQ ID NO:7:

GAACCAGGCC GATCACTTCT TGGGCTCTCT GGCATTTGCA AAGCTGCTAA              50

ACCGTACCTT GGCTGTCCCT CCTTGGATTG AGTACCAGCA TCACAAGCCT             100

CCTTTCACCA ACCTCCATGT GTCCTACCAG AAGTACTTCA AGCTGGAGCC             150

CCTCCAGGCT TACCATCGGG TCATCAGCTT GGAGGATTTC ATGGAGAAGC             200

TGGCACCCAC CCACTGGCCC CCTGAGAAGC GGGTGGCATA CTGCTTTGAG             250

GTGGCAGCCC AGCGAAGCCC AGATAAGAAG ACGTGCCCCA TGAAGGAAGG             300

AAACCCCTTT GGCCCATTCT GGGATCAGTT TCATGTGAGT TTCAACAAGT             350

CGGAGCTTTT TACAGGCATT TCCTTCAGTG CTTCCTACAG AGAACAATGG             400

AGCCAGAGAT TTTCTCCAAA GGAACATCCG GTGCTTGCCC TGCCAGGAGC             450

CCCAGCCCAG TTCCCCGTCC TAGAGGAACA CAGGCCACTA CAGAAGTACA             500

TGGTATGGTC AGACGAAATG GTGAAGACGG GAGAGGCCCA GATTCATGCC             550

CACCTTGTCC GGCCCTATGT GGGCATTCAT CTGCGCATTG GCTCTGACTG             600

GAAGAACGCC TGTGCCATGC TGAAGGACGG GACTGCAGGC TCGCACTTCA             650

TGGCCTCTCC GCAGTGTGTG GGCTACAGCC GCAGCACAGC GGCCCCCCTC             700

ACGATGACTA TGTGCCTGCC TGACCTGAAG GAGATCCAGA GGGCTGTGAA             750
```

-continued

| | |
|---|---|
| GCTCTGGGTG AGGTCGCTGG ATGCCCAGTC GGTCTACGTT GCTACTGATT | 800 |
| CCGAGAGTTA TGTGCCTGAG CTCCAACAGC TCTTCAAAGG GAAGGTGAAG | 850 |
| GTGGTGAGCC TGAAGCCTGA GGTGGCCCAG GTCGACCTGT ACATCCTCGG | 900 |
| CCAAGCCGAC CACTTTATTG CAACTGTGT CTCCTCCTTC ACTGCCTTTG | 950 |
| TGAAGCGGGA GCGGGACCTC CAGGGGAGGC CGTCTTCTTT CTTCGGCATG | 1000 |
| GACAGGCCCC CTAAGCTGCG GGACGAGTTC TGATTCTGGC CGGAGCACCA | 1050 |
| GACCCTCTGA TCCTGGAGGG ACCAGAGTCT GAGCTGGTCC TTCCAGCCAG | 1100 |
| GCCTGGCAGC CAGAGGTGCT CCGGGATTGC AAACTCCTCT TCTCACCTGC | 1150 |
| CAAAGATGGA GAAGAGTGCC AGGGACCCCT CAAGGAGGGA GACGCTCCAT | 1200 |
| ATCCCAGGGC ATAGGACTTG CAGGTTCCTA GGAGCAGGAG CATCTCCCAT | 1250 |
| CGCACGTGCT TTCTGCTCTT CTGGGAATTT CTCACACTGG CAAAGCAGTC | 1300 |
| CAGCCTCCGT CTTCTGGTCC ACTCTGCTCT GAGCAGCCTG GGATGCTGAA | 1350 |
| CTCTTCAGAG AGATTTTTTT ATAGAGAGAT TTCTATAATT TTGATACAAG | 1400 |
| GTCATGACTA TCCTAGAACT CTCTGTGGTT TTTGAAAATC ATTGAATTCT | 1450 |
| ATTAATGTAG GTACCTAAAG TGACCTTAAC TGAATGTGGA TGAGGCTGGG | 1500 |
| GCTGGTGTGG GTCTTTTGGC TGCTTTTCAA GGTGTCCCCC AATGTGGCCC | 1550 |
| TCAAGAGCCA TCCCCACTGC CTGGCCAGAG CCATTGTTGT CCCCTACTTC | 1600 |
| CTAGGCCATT TCTGGGGCTT GGGGGATGAA TGCTGTCCTG TGCTGTAAAC | 1650 |
| ACTATGCAAA TGGAAGTTAT CGGTTGTGGT GCTGTGCAGC GCTCTGTGGG | 1700 |
| CGACTAAGTG CCACTCACGC AGCATGTTCC TGGCAAGGAG CACATACCAT | 1750 |
| CAAGCCACAC TATCATGGTA TTGTTCTCAC AGTCTTTTGG TGGTTGATGG | 1800 |
| CCACTGCAAA CCTGGCACCA TCAGATCTCT TCTGATCTCT TGCCCCAGTG | 1850 |
| GGGCCTGGTT GGTAGAATGT TGGCATTCGG TTGATATCCA AAGCCTGTTC | 1900 |
| TCCCAGCCGT CCTCCTGCAG CTGGAGCCTT CAGGCCGTAT TCTCACGAGG | 1950 |
| GAACGTTTGC CAAGGCTCTG ACCTCACAGA AGATGCCCAG GGCCCAGAAG | 2000 |
| CCATCAGAAT TATCAGTGGA GAAGCACCTT TTGACTCTTC CCTTCCAATG | 2050 |
| TAATCTCTGC CAACACCATG AGGCTTAAGG TGCTCTAAGT CATGAGTGTT | 2100 |
| TTGGTCTCAA ATGCTGCAGT TTTAATAATC TGTGACTCCT GAGAGCCCAT | 2150 |
| GGTTTTTTGA CCTTGTGGTT CTAAAATTCC TTGTCTGACC CCTGTAGATC | 2200 |
| TTTTCCTTGC CATGTCACCT CCCTTGGCCT TTGATCCTGG AAAGGTGGCA | 2250 |
| GAGCCTCCAC TGAGCCAGGC CCAGAGCTCC TTGCAGTGCC TTCTTCCTTG | 2300 |
| TTTACCTGTG GGAGGAAACA CTTTTTTTGT CAGGGGCAGC CTGGTTCAGA | 2350 |
| GCTCAGAGGT CACACTGTAT CAAAGATCTC AAACAGCAAA GTCAGCATTT | 2400 |
| GCTGTATAGA GCTGCCACCC AACTCTAAGC AGGAGAAACT GTACAGAAAG | 2450 |
| GGCTTTGCTA TTTTTCCCTT TTGGGAAAAC AATGAAGTGT TTTAAGTCCT | 2500 |
| GGGTGGACTG AGAGATGGTT TGCCTGTCCA GACTTGCTCT CAAGCCTCAT | 2550 |
| CCAGAGAAGG AGCTGCAGAT GAGGGAGCCC GTACACTCCC TGCCACCACT | 2600 |
| AGGTTGTAAG CCTGTAGCTG GCTGGCTGAT TCATTTTGG AATTCATTTG | 2650 |
| CCATCCACAG CCTTACACTA GGCACACACT TTAGAGTCTG GGGCTCCAGT | 2700 |
| GGGGCCCGCC TAATTTTTTT TCCCCCCAAG ACAGGGCCTT GCTCTGTCTC | 2750 |

| | |
|---|---|
| CCAGGCTGGA GTGCAGTGGC ATGATCATGG CTTACTGCAG CCTTGATCTC | 2800 |
| CCAGGCTCAA GCGATCCTTC TGCCTCAGCC TCTCTGGTAG CTGAGACTGC | 2850 |
| ATGCCCAGCT CCAAATCACC TTGATTCATA TCAGCAGTAA TAATCACTTG | 2900 |
| TGTTCTGAAA GAAAGGGCAC CAGAAGTTCT AGCAAAATTC AGTTGTGTTC | 2950 |
| TGTGAGCTAG CACTTTTTCC TCTGACCCAA TTTTCTTACC TATAAAATGG | 3000 |
| TGATAAAAAC CGACAGGTTG TTCAAAGGCC CAGATCAGCT AAAGCATGTA | 3050 |
| TATAAGAGCA CGTTGTAAAC TTGAAAGAGA CAAAGGCACA AATGTGGCTG | 3100 |
| TTGATTAATT TGACTGCTTC TCGTTGCTCG TCACCTCCAT GCCAGGCACT | 3150 |
| GTGCTTGCTA ATTGCTTTAT GGGGGCATTC TCTTATTTAT TCCCCAGCCC | 3200 |
| TGGGAAATAG GAGCTGTCAT TATCCTTCTC TTTCTGCACA AGGAAAAATT | 3250 |
| AATGCCCTGA GAATTGTCAT AATTTTCCCA AGGCTGCCCA GCTGGTGGTG | 3300 |
| TTAAGCCAGA ATTTGACCTC CCAGAGCCAG TTTCCATTAG CTGCCATGCT | 3350 |
| CTGCTGCCTC TAATTCACAG AATGCACTTT CTACCCTGTG TGCCATGGAG | 3400 |
| ACCTCCTATG GAAAAATGAT CAGCCACCTT ACCTTCTACT GGGTACCTGC | 3450 |
| TGTGAGTCTG CCTATGCCAG AAGGATTAAG GAGGGGAGGT TACCCAAGAA | 3500 |
| ACAAAGCCTA CATGCCGCTT ACAGCCCCCG TTGGATGGTT GCTCAGTACA | 3550 |
| ACAGTCTTGC ATTCAGCAGG TGTTTGTTCA TCACCTACTA TGTGTCAGGC | 3600 |
| TCTATGCTAG GTACTGGGGA TACAGGAGAG AATCAAGCGT AAAGTCTTTG | 3650 |
| TTCTCAAGGA ATTTGCATTC TAGAAAGTAG AAGATGTAAT AAATGTACTG | 3700 |
| TGGGACATGT TAATAAGTGC TATAAAGAAA TATAAAGGGT TTGGGAGCAA | 3750 |
| AAAGAGGGAG TGGATCTATT TTAGATGAGC CCAGGTAAGA CCTCTCTGAA | 3800 |
| GAGCTGTCAT GAAGGAGGGA GGGAGCACAT TCCTGGCAGA GAAAACAGCA | 3850 |
| CGTGCAAAGG CCCCGAGACT GGAGTGTGTT CCTGAAGAGC AGCCAGGAGG | 3900 |
| CCAGCATGGC TGGAGAGGCA GGCATAGGCA GGGAACCGAG CAGCAGGTCA | 3950 |
| GAGCAGGCGA GCTGACATTC TGCAGCCTGG ACGGCCATGG CAGGAAGCTT | 4000 |
| TTAGTTGGAG AGATACAGGA AGCCTCCTAG GGTTCTGAGC AGAAGAGGGG | 4050 |
| CATGAGCTGA TTCACATTCT GAAGGACCTC TCTAGCTGGC CAGTGCTGAG | 4100 |
| GAGGTTGGAG AGAGAAAGGG TGAAAGCAGA GAGACCAGTG CAGGGCTGTT | 4150 |
| AACAGGGTTG CAGGCGAGAG ACTGGGGTGC TGGGCTCCCC TAGACTAGGA | 4200 |
| CTCCAGTGCC CTCCTCTCCC AAGAGACAAA GGCCATTGCA TTGAAGGAGG | 4250 |
| TGGGAAATGA TTAGATTCTG AACATATGTA ATTATTTTTC AGTCTTTTTC | 4300 |
| AAAGATACAA ATATTTACAT AGTTTTAATC ATGTAATATA TACAATTTAA | 4350 |
| TGTCCTAGTG TTTTACTTAA TAGTGTATCA TGTTTTCCCT GTTGGTATGT | 4400 |
| AGCCTGGATA AATGCTCTTA ATTATAAAAA ATTCTGTCGA GGAGTGTTCC | 4450 |
| ATAGTTTATT GTTTTCCTAT TATGAGAATT TAGGCCAAGT GTGGTGGCTC | 4500 |
| ATGCCTGTAA TCCCAGCACT TTGCGAGGCC GAGGTGGGCA GATCACTTGA | 4550 |
| GGTGAGGAGT TCAAGACCAG CCTGGCCAAC ATGGTGAATT ATCTCTACTA | 4600 |
| AAAATACAAA AAAATAATAA TAATAGCCAG GCGTGGTGGC ACATGCCTGT | 4650 |
| ATTCCCAGCT GCTTGGGAGG CTGAGGCAGG AGAATGGCTT GAACCTGGGA | 4700 |
| GGTGGAGGTT GCAGTGAGCC GAGATGGTGC CACTGCATTC CAGCCTGGGC | 4750 |

```
AACAGAGCGA GACTCCATCT CAAAAAAAAG GAGACTTCAT GTGCCCCCAA      4800

TTTTTCACTA TTGTTATTTG AAAAAATATT TTTATTTGTA AGAGTTTTTC      4850

TTTATTTAAA ATGTTCATTA ATAAAGTTGT TGGACGGGAA GCAAAAAAAA      4900

AAAGTTGTTT AAGATAAATT CCCAGAAGTG AATTTGTTAG ATCAAACACT      4950

TAAAACTTTT TGTTATGGAA GAATTCAAAT ATAAATAAAA AATTGTGAGT      5000

AATAAAATG                                                    5009
```

(2) INFORMATION FOR SEQ ID NO:8:

(i) SEQUENCE CHARACTERISTICS:
        (A) LENGTH: 474 amino acids
        (B) TYPE: Amino Acid
        (D) TOPOLOGY: Linear (xi) SEQUENCE DESCRIPTION: SEQ ID NO:8:

```
Met Ser Asn Tyr Arg Tyr Ser Lys Leu Asn Glu Glu Ile Ser
 1               5                  10                  15

Leu Glu Asp Met Pro Ser Ser Ala Asn Gln Ile Leu Thr Arg Gln
                20                  25                  30

Glu Gln Ile Ile Gln Glu Gln Asp Asp Glu Leu Glu Leu Val Gly
                35                  40                  45

Asn Ser Val Arg Thr Leu Arg Gly Met Ser Ser Met Ile Gly Asp
                50                  55                  60

Glu Leu Asp Gln Gln Ser Thr Met Leu Asp Asp Leu Gly Gln Glu
                65                  70                  75

Met Glu Tyr Ser Glu Thr Arg Leu Asp Thr Ala Met Lys Lys Met
                80                  85                  90

Ala Lys Leu Thr His Leu Glu Asp Gly Met Leu Leu Ala Arg Arg
                95                 100                 105

Ile Val Gln Ser Met Gln Asn Asp His Gly Ala Leu Ser Ser Pro
               110                 115                 120

Val Phe Pro Arg Leu Cys Pro Ser Gly Leu Thr Thr Tyr Val Pro
               125                 130                 135

Tyr Ile Val Asp Phe Ser Ser Leu Thr Phe His Ile Phe Ile Ile
               140                 145                 150

Ile Ile Ile Ile Ile Ile Asp Phe Cys Ser Gln Ser Gln Ser Lys
               155                 160                 165

Gly Arg Phe Gly Asn Gln Val Asp Gln Phe Leu Gly Val Leu Ala
               170                 175                 180

Phe Ala Lys Ala Leu Asp Arg Thr Leu Val Leu Pro Asn Phe Ile
               185                 190                 195

Glu Phe Lys His Pro Glu Thr Lys Met Ile Pro Phe Glu Phe Leu
               200                 205                 210

Phe Gln Val Gly Thr Val Ala Lys Tyr Thr Arg Val Val Thr Met
               215                 220                 225

Gln Glu Phe Thr Lys Lys Ile Met Pro Thr His Phe Val Gly Thr
               230                 235                 240

Pro Arg Gln Ala Ile Tyr Asp Lys Ser Ala Glu Pro Gly Cys His
               245                 250                 255

Ser Lys Glu Gly Asn Pro Phe Gly Pro Tyr Trp Asp Gln Ile Asp
               260                 265                 270

Val Ser Phe Val Gly Asp Glu Tyr Phe Gly Asp Ile Pro Gly Gly
               275                 280                 285
```

```
Phe Asp Leu Asn Gln Met Gly Ser Arg Lys Lys Trp Leu Glu Lys
            290                 295                 300

Phe Pro Ser Glu Glu Tyr Pro Val Leu Ala Phe Ser Ser Ala Pro
            305                 310                 315

Ala Pro Phe Pro Ser Lys Gly Lys Val Trp Ser Ile Gln Lys Tyr
            320                 325                 330

Leu Arg Trp Ser Ser Arg Ile Thr Glu Gln Ala Lys Lys Phe Ile
            335                 340                 345

Ser Ala Asn Leu Ala Lys Pro Phe Val Ala Val His Leu Arg Asn
            350                 355                 360

Asp Ala Asp Trp Val Arg Val Cys Glu His Ile Asp Thr Thr Thr
            365                 370                 375

Asn Arg Pro Leu Phe Ala Ser Glu Gln Cys Leu Gly Glu Gly His
            380                 385                 390

His Leu Gly Thr Leu Thr Lys Glu Ile Cys Ser Pro Ser Lys Gln
            395                 400                 405

Gln Ile Leu Glu Gln Ile Glu Ala His Arg Gln Glu Pro Asp Asp
            410                 415                 420

Met Tyr Thr Ser Leu Ala Ile Met Gly Arg Ala Asp Leu Phe Val
            425                 430                 435

Gly Asn Cys Val Ser Thr Phe Ser His Ile Val Lys Arg Glu Arg
            440                 445                 450

Asp His Ala Gly Gln Ser Pro Arg Pro Ser Ala Phe Phe Gly Ile
            455                 460                 465

Arg Ala Val Lys Arg His Ile Asp Leu
            470                 474

(2) INFORMATION FOR SEQ ID NO:9:

(i) SEQUENCE CHARACTERISTICS:
        (A) LENGTH: 61 amino acids
        (B) TYPE: Amino Acid
        (D) TOPOLOGY: Linear (xi) SEQUENCE DESCRIPTION: SEQ ID NO:9:

Met Pro Ala Gly Ser Trp Asp Pro Ala Gly Tyr Leu Leu Tyr Cys
 1               5                  10                  15

Pro Cys Met Gly Arg Phe Gly Asn Gln Ala Asp His Phe Leu Gly
                20                  25                  30

Ser Leu Ala Phe Ala Lys Leu Leu Asn Arg Thr Leu Ala Val Pro
                35                  40                  45

Pro Trp Ile Glu Tyr Gln His His Lys Pro Pro Phe Thr Asn Leu
                50                  55                  60

His
 61

(2) INFORMATION FOR SEQ ID NO:10:

(i) SEQUENCE CHARACTERISTICS:
        (A) LENGTH: 40 base pairs
        (B) TYPE: Nucleic Acid
        (C) STRANDEDNESS: Single
        (D) TOPOLOGY: Linear (xi) SEQUENCE DESCRIPTION: SEQ ID NO:10:

CTTCTTGGGC TCTCTGGCAT TTGCAAAGCT GCTAAACCGT                40

(2) INFORMATION FOR SEQ ID NO:11:
```

```
    (i) SEQUENCE CHARACTERISTICS:
         (A) LENGTH: 40 base pairs
         (B) TYPE: Nucleic Acid
         (C) STRANDEDNESS: Single
         (D) TOPOLOGY: Linear (xi) SEQUENCE DESCRIPTION: SEQ ID NO:11:

TTCGACGATT TGGCATGGAA CCGACAGGGA GGAACCTAAC                                   40

(2) INFORMATION FOR SEQ ID NO:12:

(i) SEQUENCE CHARACTERISTICS:
         (A) LENGTH: 40 base pairs
         (B) TYPE: Nucleic Acid
         (C) STRANDEDNESS: Single
         (D) TOPOLOGY: Linear (xi) SEQUENCE DESCRIPTION: SEQ ID NO:12:

CTTCTTGGGC TCTCTGGCAT TTGCAAAGCT GCTAAACCGT                                   40

(2) INFORMATION FOR SEQ ID NO:13:

(i) SEQUENCE CHARACTERISTICS:
         (A) LENGTH: 30 base pairs
         (B) TYPE: Nucleic Acid
         (C) STRANDEDNESS: Single
         (D) TOPOLOGY: Linear (xi) SEQUENCE DESCRIPTION: SEQ ID NO:13:

TCCCTGGGGA GTTCCTCCCT CTGCGAGGTA                                              30

(2) INFORMATION FOR SEQ ID NO:14:

(i) SEQUENCE CHARACTERISTICS:
         (A) LENGTH: 28 amino acids
         (B) TYPE: Amino Acid
         (D) TOPOLOGY: Linear (xi) SEQUENCE DESCRIPTION: SEQ ID NO:14:

Arg Ser His His His His His His Met Pro Ala Gly Ser Trp Asp
 1               5                   10                  15

Pro Ala Gly Tyr Leu Leu Tyr Xaa Pro Xaa Met Gly Arg
                20                  25          28

(2) INFORMATION FOR SEQ ID NO:15:

(i) SEQUENCE CHARACTERISTICS:
         (A) LENGTH: 52 amino acids
         (B) TYPE: Amino Acid
         (D) TOPOLOGY: Linear (xi) SEQUENCE DESCRIPTION: SEQ ID NO:15:

Thr Val Asp Gly Asp Gln Cys Glu Ser Asn Pro Cys Leu Asn Gly
 1               5                   10                  15

Gly Ser Cys Lys Asp Asp Ile Asn Ser Tyr Glu Cys Trp Cys Pro
                20                  25                  30

Phe Gly Phe Glu Gly Lys Asn Cys Glu Leu Asp Val Thr His His
                35                  40                  45

His His His His Gly Ser Ala
                50      52

(2) INFORMATION FOR SEQ ID NO:16:

(i) SEQUENCE CHARACTERISTICS:
         (A) LENGTH: 1100 base pairs
         (B) TYPE: Nucleic Acid
```

(C) STRANDEDNESS: Single
        (D) TOPOLOGY: Linear (xi) SEQUENCE DESCRIPTION: SEQ ID NO:16:

```
ATGCCCGCGG GCTCCTGGGA CCCGGCCGGT TACCTGCTCT ACTGCCCCTG            50

CATGGGGCGC TTTGGGAACC AGGCCGATCA CTTCTTGGGC TCTCTGGCAT           100

TTGCAAAGCT GCTAAACCGT ACCTTGGCTG TCCCTCCTTG GATTGAGTAC           150

CAGCATCACA AGCCTCCTTT CACCAACCTC CATGTGTCCT ACCAGAAGTA           200

CTTCAAGCTG GAGCCCCTCC AGGCTTACCA TCGGGTCATC AGCTTGGAGG           250

ATTTCATGGA AAAGCTGGCA CCCACCCACT GGCCCCCTGA AAAGCGGGTG           300

GCATACTGCT TTGAGGTGGC AGCCCAGCGA AGCCCAGATA AGAAGACGTG           350

CCCCATGAAG GAAGGAAACC CCTTTGGCCC ATTCTGGGAT CAGTTTCATG           400

TGAGTTTCAA CAAGTCGGAG CTTTTTACAG GCATTTCCTT CAGTGCTTCC           450

TACAGAGAAC AATGGAGCCA GAGATTTTCT CCAAAGGAAC ATCCGGTGCT           500

TGCCCTGCCA GGAGCCCCAG CCCAGTTCCC CGTCCTAGAA GAACACAGGC           550

CACTACAGAA GTACATGGTA TGGTCAGACG AAATGGTGAA GACGGGAGAG           600

GCCCAGATTC ATGCCCACCT TGTCCGGCCC TATGTGGGCA TTCATCTGCG           650

CATTGGCTCT GACTGGAAGA ACGCCTGTGC CATGCTGAAG GACGGGACTG           700

CAGGCTCGCA CTTCATGGCC TCTCCGCAGT GTGTGGGCTA CAGCCGCAGC           750

ACAGCGGCCC CCCTCACGAT GACTATGTGC CTGCCTGACC TGAAGGAGAT           800

CCAGAGGGCT GTGAAGCTCT GGGTGAGGTC GCTGGATGCC CAGTCGGTCT           850

ACGTTGCTAC TGATTCCGAG AGTTATGTGC CTGAGCTCCA ACAGCTCTTC           900

AAAGGGAAGG TGAAGGTGGT GAGCCTGAAG CCTGAGGTGG CCCAGGTCGA           950

CCTGTACATC CTCGGCCAAG CCGACCACTT TATTGGCAAC TGTGTCTCCT          1000

CCTTCACTGC CTTTGTGAAG CGGGAGCGGG ACCTCCAGGG GAGGCCGTCT          1050

TCTTTCTTCG GCATGGACAG GCCCCCTAAG CTGCGGGACG AGTTCTGATT          1100
```

(2) INFORMATION FOR SEQ ID NO:17:

(i) SEQUENCE CHARACTERISTICS:
        (A) LENGTH: 343 amino acids
        (B) TYPE: Amino Acid
        (D) TOPOLOGY: Linear (xi) SEQUENCE DESCRIPTION: SEQ ID NO:17:

```
Asn Gln Ala Asp His Phe Leu Gly Ser Leu Ala Phe Ala Lys Leu
  1               5                  10                  15

Leu Asn Arg Thr Leu Ala Val Pro Pro Trp Ile Glu Tyr Gln His
                 20                  25                  30

His Lys Pro Pro Phe Thr Asn Leu His Val Ser Tyr Gln Lys Tyr
                 35                  40                  45

Phe Lys Leu Glu Pro Leu Gln Ala Tyr His Arg Val Ile Ser Leu
                 50                  55                  60

Glu Asp Phe Met Glu Lys Leu Ala Pro Thr His Trp Pro Pro Glu
                 65                  70                  75

Lys Arg Val Ala Tyr Cys Phe Glu Val Ala Ala Gln Arg Ser Pro
                 80                  85                  90

Asp Lys Lys Thr Cys Pro Met Lys Glu Gly Asn Pro Phe Gly Pro
                 95                 100                 105
```

-continued

```
Phe Trp Asp Gln Phe His Val Ser Phe Asn Lys Ser Glu Leu Phe
                110                 115                 120

Thr Gly Ile Ser Phe Ser Ala Ser Tyr Arg Glu Gln Trp Ser Gln
                125                 130                 135

Arg Phe Ser Pro Lys Glu His Pro Val Leu Ala Leu Pro Gly Ala
                140                 145                 150

Pro Ala Gln Phe Pro Val Leu Glu Glu His Arg Pro Leu Gln Lys
                155                 160                 165

Tyr Met Val Trp Ser Asp Glu Met Val Lys Thr Gly Glu Ala Gln
                170                 175                 180

Ile His Ala His Leu Val Arg Pro Tyr Val Gly Ile His Leu Arg
                185                 190                 195

Ile Gly Ser Asp Trp Lys Asn Ala Cys Ala Met Leu Lys Asp Gly
                200                 205                 210

Thr Ala Gly Ser His Phe Met Ala Ser Pro Gln Cys Val Gly Tyr
                215                 220                 225

Ser Arg Ser Thr Ala Ala Pro Leu Thr Met Thr Met Cys Leu Pro
                230                 235                 240

Asp Leu Lys Glu Ile Gln Arg Ala Val Lys Leu Trp Val Arg Ser
                245                 250                 255

Leu Asp Ala Gln Ser Val Tyr Val Ala Thr Asp Ser Glu Ser Tyr
                260                 265                 270

Val Pro Glu Leu Gln Gln Leu Phe Lys Gly Lys Val Lys Val Val
                275                 280                 285

Ser Leu Lys Pro Glu Val Ala Gln Val Asp Leu Tyr Ile Leu Gly
                290                 295                 300

Gln Ala Asp His Phe Ile Gly Asn Cys Val Ser Ser Phe Thr Ala
                305                 310                 315

Phe Val Lys Arg Glu Arg Asp Leu Gln Gly Arg Pro Ser Ser Phe
                320                 325                 330

Phe Gly Met Asp Arg Pro Pro Lys Leu Arg Asp Glu Phe
                335                 340             343
```